(12) United States Patent
Agulnick et al.

(10) Patent No.: US 10,695,380 B2
(45) Date of Patent: Jun. 30, 2020

(54) CRYOPRESERVATION OF ENCAPSULATED PANCREATIC ENDODERM CELLS

(71) Applicant: ViaCyte, Inc., San Diego, CA (US)

(72) Inventors: Alan Agulnick, San Diego, CA (US); Laura Martinson, San Diego, CA (US); Evert Kroon, San Diego, CA (US); Michael Scott, San Diego, CA (US); Chad Green, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 105 days.

(21) Appl. No.: 15/795,113

(22) Filed: Oct. 26, 2017

(65) Prior Publication Data

US 2018/0064763 A1 Mar. 8, 2018

Related U.S. Application Data

(63) Continuation of application No. 14/846,114, filed on Sep. 4, 2015, now abandoned, which is a continuation of application No. PCT/US2014/022065, filed on Mar. 7, 2014.

(60) Provisional application No. 61/775,480, filed on Mar. 8, 2013.

(51) Int. Cl.
| | | |
|---|---|---|
| *A61K 35/39* | (2015.01) | |
| *A01N 1/02* | (2006.01) | |
| *A61K 38/28* | (2006.01) | |
| *C12N 5/071* | (2010.01) | |

(52) U.S. Cl.
CPC .............. *A61K 35/39* (2013.01); *A01N 1/021* (2013.01); *A01N 1/0278* (2013.01); *A01N 1/0284* (2013.01); *A61K 38/28* (2013.01); *C12N 5/0678* (2013.01)

(58) Field of Classification Search
None
See application file for complete search history.

(56) References Cited

U.S. PATENT DOCUMENTS

| | | |
|---|---|---|
| 5,964,261 A | 10/1999 | Neuenfeldt et al. |
| 6,176,089 B1 | 1/2001 | Bouche |
| 2010/0124564 A1 | 5/2010 | Martinson et al. |
| 2013/0022986 A1 | 1/2013 | Hosoya |

FOREIGN PATENT DOCUMENTS

| | | |
|---|---|---|
| WO | 2010057039 A2 | 5/2010 |
| WO | 2012172354 A1 | 12/2012 |
| WO | 2014008432 A1 | 1/2014 |

OTHER PUBLICATIONS

M. E. Gonzalez-Benito et al; Biodiversity and Conservation, vol. 6, No. 4, Jan. 1, 1997, pp. 583-590; XP055130924. ISSN: 0960-3115; DOI:10.1023/A:1018337429589, p. 585.
Yakhnenko Ilya et al: Cryopreservation of Human Insulin Expressing Cells Macro-Encapsulated in a Durable Therapeutic Immuniosolating Device Theracyte (TM), Cryoletters, vol. 33, No. 6, Nov. 2012, pp. 518-531.

*Primary Examiner* — Michelle F. Paguio Frising
(74) *Attorney, Agent, or Firm* — Klarquist Sparkman, LLP

(57) ABSTRACT

Disclosed herein are methods for cryopreserving, hibernation and room temperature storage of PEC aggregates, implantable semipermeable devices and the VC combination product.

18 Claims, 14 Drawing Sheets

Specification includes a Sequence Listing.

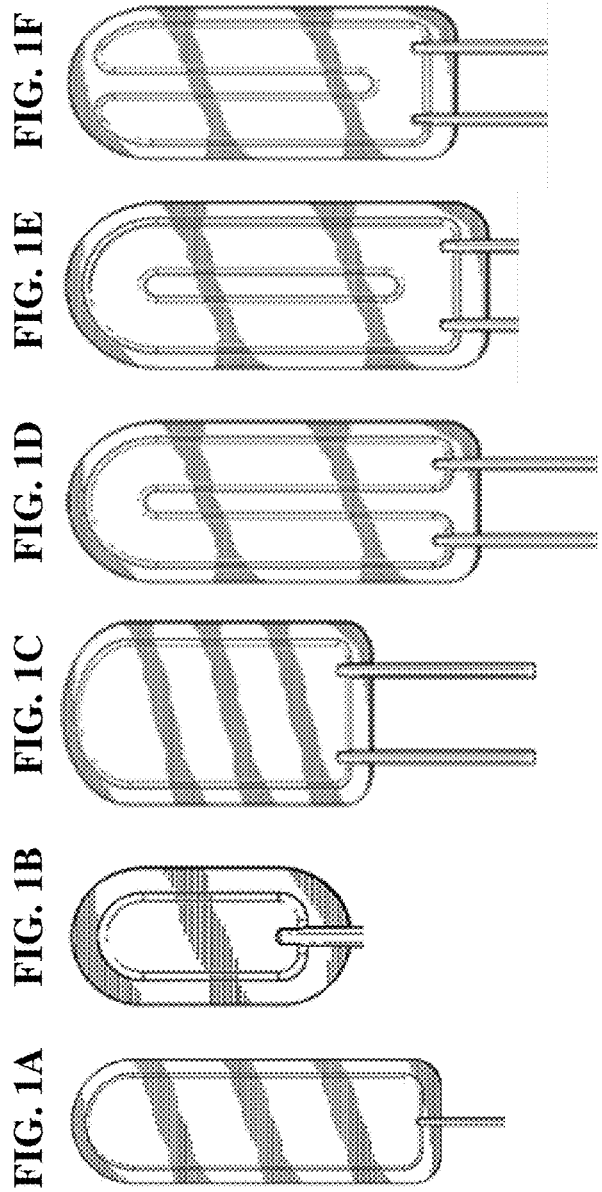
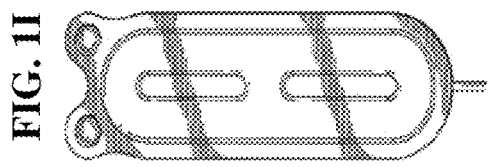
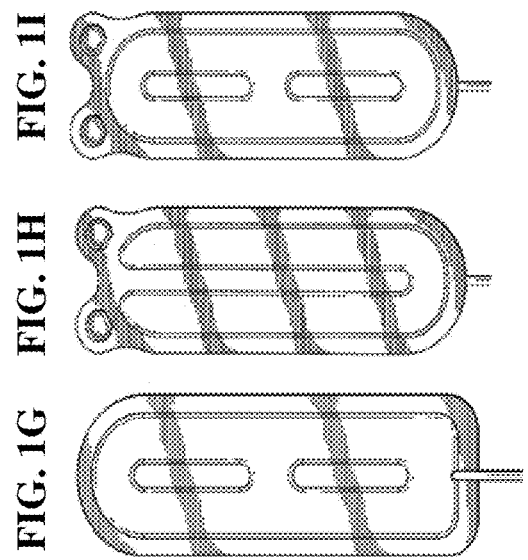

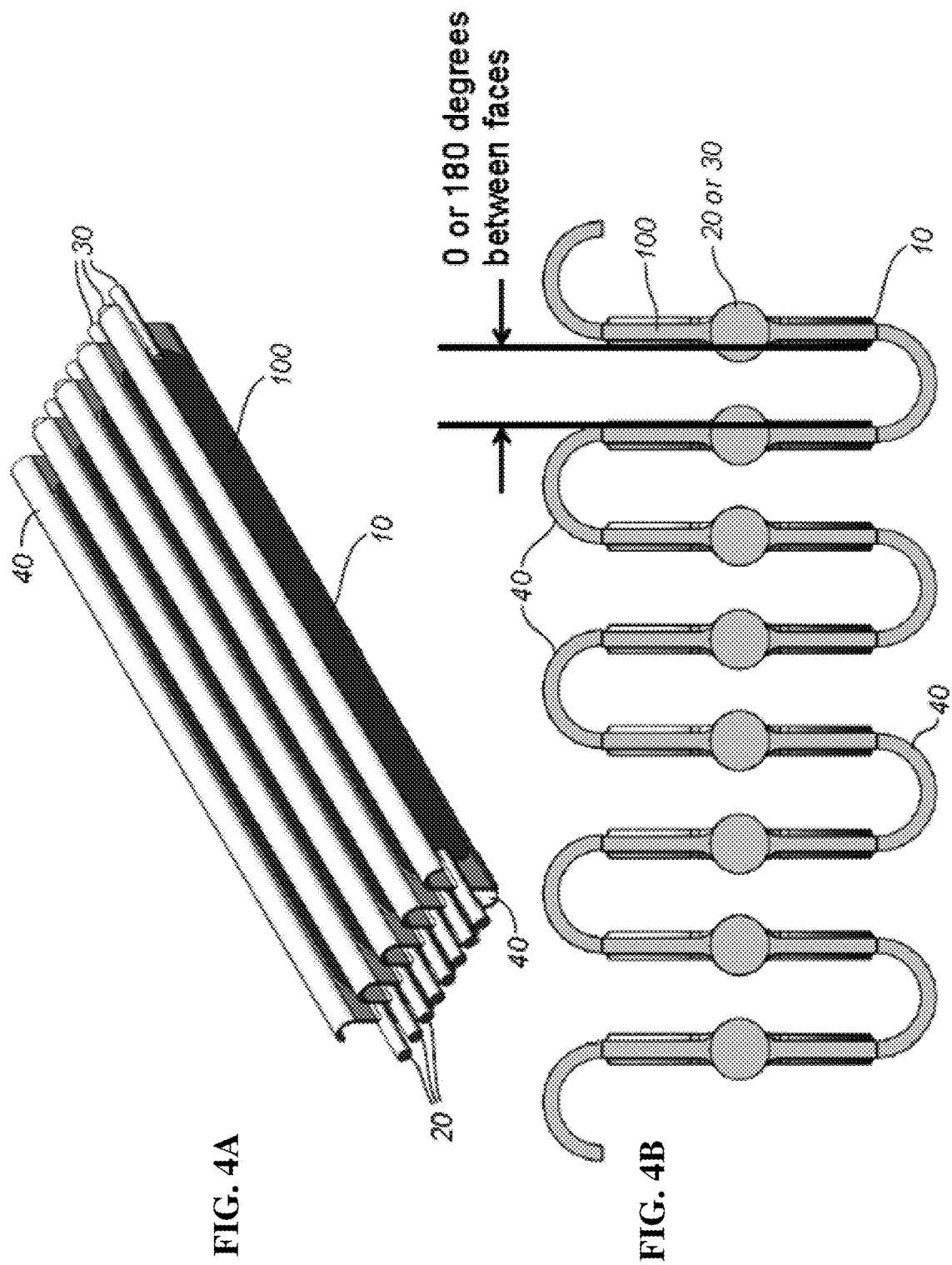

FIG. 6

Add cryopreservation media to PDX-1 positive pancreatic endoderm cell population
↓
Load the PDX-1 positive pancreatic endoderm cell population in an encapsulation device to form a cell-device combination product
↓
Cryopreserve the cell-device combination product at about -150°C.
↓
Implant the cell-device combination product into a mammalian host

SEQUENCE LISTING

<160> NUMBER OF SEQ ID NOS: 46

<210> SEQ ID NO 1

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 1
aagaggccat caagcagatc a                                                    21

<210> SEQ ID NO 2
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 2
caggaggcgc atccaca                                                         17

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
ctggcctgta cccctcatca                                                      20

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
cttcccgtct ttgtccaaca a                                                    21

<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 5
aagtctacca aagctcacgc g                                                    21

<210> SEQ ID NO 6
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 6
gtaggcgccg cctgc                                                           15

<210> SEQ ID NO 7
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 7
```
gctcatcgct ctctattctt ttgc                                          24

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
ggttgaggcg tcatcctttc t                                             21

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
gggagcggtg aagatgga                                                 18

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
tcatgttgct cacggaggag ta                                            22

<210> SEQ ID NO 11
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 11
aagcatttac tttgtggctg gatt                                          24

<210> SEQ ID NO 12
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 12
tgatctggat ttctcctctg tgtct                                         25

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 13
cgctccgctt agcagcat                                                 18

<210> SEQ ID NO 14
<211> LENGTH: 22
<212> TYPE: DNA

```
<213> ORGANISM: Artificial Sequence
<220> FEATURE:
<223> OTHER INFORMATION: Synthetic polynucleotide

<400> SEQUENCE: 14
gtgttgcctc tatccttccc at                                              22

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
gaagaaggaa gccgtccaga                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
gaccttcgag tgctgatccg                                                 20

<210> SEQ ID NO 17
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 17
ggcgcagcag aatccaga                                                   18

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: n is a, c, g, or t

<400> SEQUENCE: 18
nnnnnnnnnn nnnnnnnnnn                                                 20

<210> SEQ ID NO 19
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 19
caccgcgggc atgatc                                                     16

<210> SEQ ID NO 20
<211> LENGTH: 19
<212> TYPE: DNA
<213> ORGANISM: Artificial Sequence
<220> FEATURE:
<223> OTHER INFORMATION: Synthetic polynucleotide
```

<400> SEQUENCE: 20
acttccccag gaggttcga                                                    19

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
ggccttcagt actccctgca                                                   20

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 22
gggacttgga gcttgagtcc t                                                 21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
gaaggtcatc atctgccatc g                                                 21

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
ggccataatc agggtcgct                                                    19

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
ccccagactc cgtcagtttc                                                   20

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
tccgtctggt tgggttcag                                                    19

<210> SEQ ID NO 27

```
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 27
ccagaaagga tgcctcataa agg                                              23

<210> SEQ ID NO 28
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 28
tctgcgcgcc cctagtta                                                    18

<210> SEQ ID NO 29
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 29
tgggctcgag aaggatgtg                                                   19

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
gcatagtcgc tgcttgatcg                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
ccgagtccag gatccaggta                                                  20

<210> SEQ ID NO 32
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 32
ctctgacgcc gagacttgg                                                   19

<210> SEQ ID NO 33
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 33
```
cctcttgcaa tgcggaaag                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 34
cgggaggaag gctctcact                                    19

<210> SEQ ID NO 35
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 35
gaggagaaag tggaggtctg gtt                               23

<210> SEQ ID NO 36
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 36
ctctgatgag gaccgcttct g                                 21

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37
acagtgccct tcagccagac t                                 21

<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38
acaactactt tttcacagcc ttcgt                             25

<210> SEQ ID NO 39
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 39
gagaaaccca ctggagatga aca                               23

<210> SEQ ID NO 40
<211> LENGTH: 23
<212> TYPE: DNA

```
<213> ORGANISM: Artificial Sequence
<220> FEATURE:
<223> OTHER INFORMATION: Synthetic polynucleotide

<400> SEQUENCE: 40
ctcatggcaa agttcttcca gaa                                             23

<210> SEQ ID NO 41
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 41
atgcaccgct acgacatgg                                                  19

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
ctcatgtagc cctgcgagtt g                                               21

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
ctggctgtgg caaggtcttc                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
cagccctcaa actcgcactt                                                 20

<210> SEQ ID NO 45
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 45
atcgaggagc gccacaac                                                   18

<210> SEQ ID NO 46
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 46
tgctggatgg tgtcctggt                                                    19
```

CRYOPRESERVATION OF ENCAPSULATED PANCREATIC ENDODERM CELLS

CROSS-REFERENCE TO RELATED APPLICATIONS

This application is a continuation of U.S. patent application Ser. No. 14/846,114, filed on Sep. 4, 2015, which is a continuation of PCT Application No. PCT/US2014/022065, filed Mar. 7, 2014, which was published in English under PCT Article 21(2), which claims the benefit of U.S. Provisional Application No. 61/775,480, filed Mar. 8, 2013. The prior applications are incorporated herein by reference in their entirety.

STATEMENT OF GOVERNMENT SUPPORT

This research was made possible, in part, by an award from the California Institute for Regenerative Medicine (CIRM), Strategic Partnership Award (SPA) Number SP1-06513.

FIELD OF THE INVENTION

This application relates generally to cryopreservation, hibernation and room temperature storage of biological materials, medical devices and combinations of the two as well as uses thereof. More particularly, the application relates to methods for cryopreserving, hibernating and storing at room temperature encapsulated pancreatic endoderm cell (PEC) aggregates also referred to as ViaCyte's (VC) combination product

BACKGROUND

Cryopreservation has been an effective method for long-term storage of biological material. Long-term storage of cells and tissue for use in clinical transplantation is based on the inherent need to collect adequate cells or tissue and to have them available at times that are suitable for transplantation into a patient. For cell-based therapies to fully reach their clinical potential, isolated cell types including PEC aggregates, implantable, semipermeable devices and encapsulated PEC aggregates (VC combination product) need to be preserved for significant periods of time (months to preferably years) so that they can be appropriately banked and distributed for on-demand utilization. Cryopreservation represents one tenable option for long-term preservation. Cell cryopreservation, the process of exposing cells to extremely low temperatures (−80° C. to −196° C.), makes possible the long term storage of living cells. Hibernation and room temperature storage makes possible the short term storage of living cells while maintaining in vivo function.

SUMMARY OF THE INVENTION

The application provides methods to cryopreserve or freeze cells, an implantable, semi-permeable device or a combination product. Specifically, the application provides methods to cryopreserve or freeze: PEC aggregates, an implantable, semi-permeable cell-encapsulation device and a cell-device combination product. The embodiments disclosed herein overcome disadvantages of the prior art by providing a cell-device combination product that can be stored long term or transported to the clinician as a ready to use product when needed.

One embodiment provides a method for cryopreserving an encapsulated cell population, said method comprising: (a) obtaining a cell population to be cryopreserved; (b) loading the cell population into an implantable semi-permeable encapsulation device thereby making an encapsulated cell population; and (c) contacting the encapsulated cell population with a cryopreservative for at least 20 minutes; thereby cryopreserving the encapsulated cell population.

One embodiment provides a method for producing insulin in vivo in a mammal, said method comprising: (a) obtaining an in vitro human pancreatic cell aggregate population; (b) loading the pancreatic cell aggregate population into an cell encapsulation device thereby making an encapsulated pancreatic cell population; (c) contacting the pancreatic cell population with a cryopreservative for at least 20 minutes thereby cryopreserving the encapsulated pancreatic cell population; (d) thawing the encapsulated pancreatic cell population; (e) implanting the encapsulated pancreatic cell population into a mammalian host; and (f) maturing the encapsulated pancreatic cell population in vivo to form a mature cell population comprising of endocrine and acinar cells, wherein at least some of the endocrine cells are insulin secreting cells that produce insulin in response to glucose stimulation in vivo, thereby producing insulin in vivo to the mammal.

One embodiment provides a method for cryopreserving an encapsulated cell population, said method comprising: (a) obtaining a cell population to be cryopreserved; (b) loading the cell population into an implantable device thereby making encapsulated cell population; (c) contacting the encapsulated cell population with a cryopreservation solution; and (d) storing the encapsulated cell population at room temperature thereby cryopreserving an encapsulated cell population.

One embodiment provides a method for producing insulin in vivo in a mammal, said method comprising: (a) obtaining an in vitro human PDX1 positive pancreatic endoderm population; (b) loading the PDX1 positive pancreatic endoderm population into an implantable encapsulation device thereby making an encapsulated cell population; (c) contacting the encapsulated cell population with a cryopreservation solution; (d) storing the encapsulated cell population at room temperature; (e) implanting the encapsulated cell population into a mammalian host; and (f) maturing the encapsulated cell population in said device in vivo to become at least endocrine and acinar cells, wherein at least some of the endocrine cells are insulin secreting cells that produce insulin in response to glucose stimulation in vivo, thereby producing insulin in vivo to the mammal.

One embodiment provides a method for cryopreserving encapsulated cell population, said method comprising: (a) obtaining a cell population to be cryopreserved; (b) loading the cell population into an encapsulation device thereby making encapsulated cell population; (c) contacting the encapsulated cell population with a cryopreservation solution; and (d) storing the encapsulated cells at 4° C. thereby cryopreserving encapsulated cell population.

One embodiment provides a method for producing insulin in vivo in a mammal, said method comprising: (a) obtaining an in vitro human PDX1 positive pancreatic endoderm population; (b) loading the PDX1 positive pancreatic endoderm population into an encapsulation device to create an encapsulated cell population; (c) contacting the encapsulated cell population with a cryopreservation solution; (d) storing the encapsulated cell population at 4° C.; (e) implanting the encapsulated cell population into a mammalian host; and maturing the encapsulated cell population in in vivo such that the mature cell population comprises endocrine and acinar cells, wherein at least some of the endocrine cells are insulin secreting cells that produce insulin in response to glucose stimulation in vivo, thereby producing insulin in vivo to the mammal.

In one embodiment the cryopreserved cells are PDX1 positive pancreatic endoderm cells including but not limited to PEC or pancreatic endoderm, or pancreatic progenitor cells (stage 3 or stage 4), definitive endoderm lineage cells (stage 2), PDX1-negative foregut endoderm cells (stage 3), and endocrine precursor cells (stage 5-6), and immature endocrine cells or immature beta cells (stage 7) or any combination thereof.

In one embodiment the temperature of the cryopreserved cells, or the cell-device combination product is decreased to less than about 0° C., −10° C., −20° C., −30° C., −40° C., −50° C., −60° C., −70° C., −80° C., −90° C., −100° C., −110° C., −120° C., −130° C., −140° C., −150° C., −160° C., −170° C., −180° C., −190° C., −200° C., −210° C., −220° C., −230° C., −240° C., −250° C., or −260° C., or preferably from about −90° C. to −260° C.

In one embodiment the temperature of the stored cells, or cell-device combination product is room temperature, at about 0° C., −1° C., −2° C., −3° C., −4° C., −5° C., −6° C., −7° C., −8° C., −9° C., −10° C. and preferably is between −2° C. and −6 and is more preferably −4° C.

In one embodiment the cryopreserved cells, cell-encapsulation device or cell-device combination product are stored for about 1 hour, 2 hours, 5 hours, 10 hours, 15 hours, 20 hours, 24 hours, 2 days, 4 days, 5 days, 1 week, 2 weeks, 3 weeks, 4 weeks, 1 month, 2 months, 3 months, 4 months, 5 months, 6 months, 8 months, 10 months, 1 year, 2 years, 4 years or more.

Another embodiment relates to a method where the cryopreserved cells, cell-encapsulating device or cell-device combination product are cryopreserved and thawed at least 1, 2, 3, 4, 5, 6, 7, 8, 9, 10, 20 or more times. In embodiments where the PEC aggregates are cryopreserved and thawed multiple times, it is desirable to have the cells of interest survive the freeze thaw cycle. For example, in Example 1 below, there is increased cell numbers of non-endocrine cell populations (CHGA−/PDX1+/NKX6.1+) following cryopreservation and thaw as compared to cells that have not been cryopreserved. In another aspect, it is desirable to have fewer residual or endocrine cells (CHGA+) after cryopreservation and thaw as compared to cells that have not been cryopreserved.

In one embodiment 5%, 10%, 15%, 20%, 30%, 40%, 50%, 60%, 70%, 80%, 90%, 95%, 98% preferably 90%-95% of the cryopreserved cells survive thawing following cryopreservation. In one embodiment 5%, 10%, 15%, 20%, 30%, 40%, 50%, 60%, 70%, 80%, 90%, 95%, 98% preferably 90%-95% of the cryopreserved cells survive thawing following cryopreservation in DMSO. In one embodiment 5%, 10%, 15%, 20%, 30%, 40%, 50%, 60%, 70%, 80%, 90%, 95%, 98% preferably 90%-95% of the cells stored at room temperature or 4° C. in preservation solution survive.

Another embodiment provides a method for enriching the non-endocrine cells in a cell population comprising: (a) obtaining a PDX1 positive pancreatic endoderm cell population to be cryopreserved; (b) contacting the cell population with a cryopreservative for at least 20 minutes thereby cryopreserving the cell population; (c) thawing the cryopreserved cell population wherein a non-endocrine subpopulation is higher than an endocrine subpopulation thereby enriching for a non-endocrine cells in a cell population. In another embodiment, the transplanted cell population is capable of maturing into endocrine and acinar cells in the mammalian host, preferably capable of maturing into mature endocrine cells, and preferably into mature insulin secreting cells or beta cells.

The cell population of claim 16, wherein the PDX1 positive pancreatic endoderm population is capable of maturing into beta cells which are capable of secreting insulin in response to glucose stimulation.

Another embodiment relates to the time in post thaw culture. Cryopreserved cell aggregates may be used for transplantation following 1, 2, 3, 4, 5, 6, 7, 8, 9, 10 days preferably 3 or 4 days and most preferably 4 days post-thaw culturing.

Another embodiment relates to methods cryopreserving or storing cells wherein a cryopreservative or storing solution is added to the cells prior to encapsulating the cells into the device.

Another embodiment relates to methods wherein the encapsulated cell is shipped to the implantation site in a cryopreserved state.

Another embodiment relates to methods wherein encapsulated cells do not leak from the device.

Another embodiment relates to methods wherein the cell survival rate is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% after cryopreservation and thawing. In one embodiment, the cell survival rate is preferably, greater than about 40%, greater than about 50%, greater than about 60%, and greater than about 95%.

In one embodiment, the cell encapsulation device comprises no loading ports, one or two loading port, and preferably at least one loading port.

In one embodiment, the cell encapsulation device comprises at least 1, 2, 3, 4, 5, 6, 7, 8, 9, 10 or more internal welds in the cell chamber or lumen, wherein the welds restrict cell chamber expansion.

These and other embodiments will be apparent from the description that follows.

BRIEF DESCRIPTION OF THE DRAWINGS

FIGS. 1A-1I are perspective views of a single and dual ported encapsulation device with embodiments and without internal welds, with and without suture or ear tabs. FIG. 1A: single ported encapsulation device; FIG. 1B: single ported encapsulation device; FIG. 1C: dual ported encapsulation device; FIG. 1D: dual ported encapsulation device; FIG. 1E: dual ported encapsulation device; FIG. 1F: dual ported encapsulation device; FIG. 1G: dual ported encapsulation device; FIG. 1H: dual ported encapsulation device with ear tabs; FIG. 1I: dual ported encapsulation device with ear tabs.

FIG. 3A is a side view and FIG. 3B is a cross section taken through the center of the device along the internal weld or seal region.

FIGS. 4A-4B are perspective (FIG. 4A) and side (FIG. 4B) views of a large capacity encapsulating device embodiment.

FIG. 5B: front view; FIG. 5C: side view.

FIG. 6 is a schematic of a cryopreservation protocol.

SEQUENCE LISTING

Figure 2A:
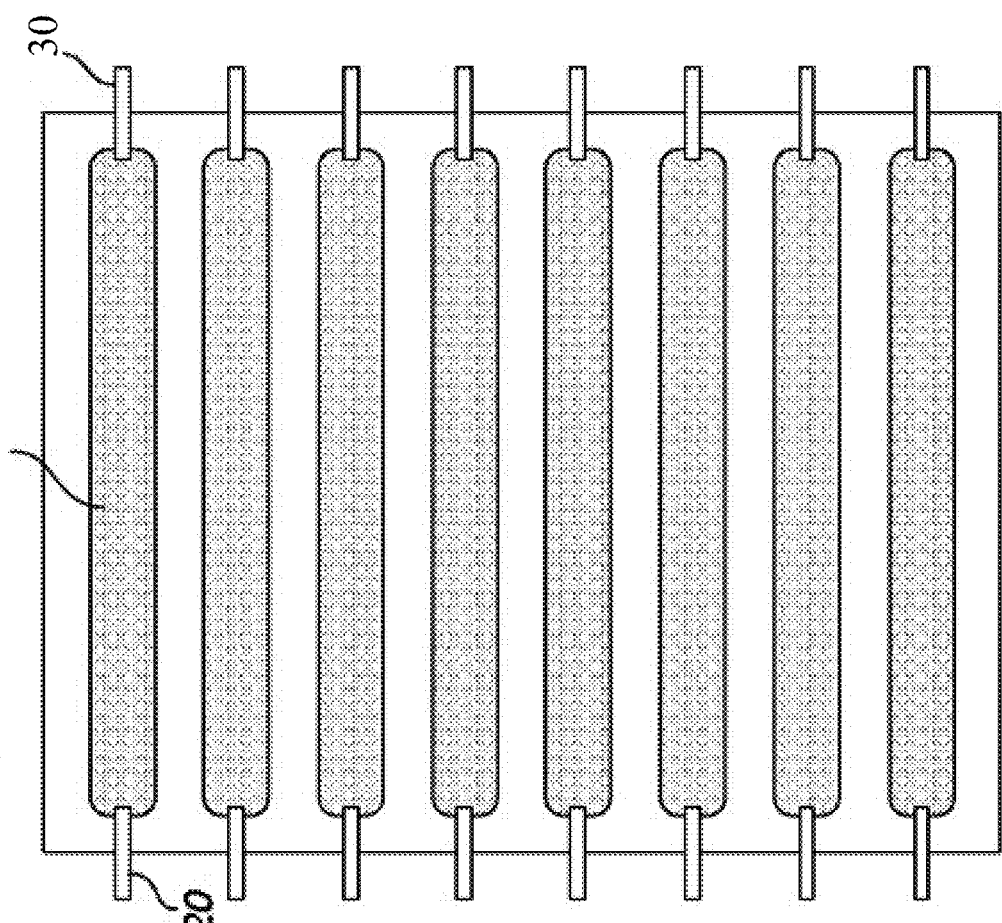
FIGS. 2A-2B are a top section view of single (FIG. 2A) and dual (FIG. 2B) ported encapsulation device embodiments.

The Sequence Listing is submitted as an ASCII text file [9511-96330-04_Sequence_Listing.txt, Oct. 26, 2017, 9.41 KB], which is incorporated by reference herein.

DETAILED DESCRIPTION OF THE INVENTION

The present invention may be understood more readily by reference to the following detailed description of the preferred embodiments of the invention and the Examples included herein. However, before the present compounds, compositions, and methods are disclosed and described, it is to be understood that this invention is not limited to specific cell types, specific feeder cell layers, specific conditions, or specific methods, etc., and, as such, may vary. Numerous modifications and variations therein will be apparent to those skilled in the art. It is also to be understood that the terminology used herein is for the purpose of describing specific embodiments only and is not intended to be limiting.

Unless otherwise noted, the terms used herein are to be understood according to conventional usage by those of ordinary skill in the relevant art. Throughout this application, various patent and non-patent publications are referenced. The disclosures of all of these publications and those references cited within those publications in their entireties are hereby incorporated by reference into this application in their entirety in order to more fully describe the state of the art to which this patent pertains.

Other suitable embodiments described herein are further described in detail in at least U.S. Pat. No. 8,211,699, METHODS FOR CULTURING PLURIPOTENT STEM CELLS IN SUSPENSION USING ERBB3 LIGANDS, issued Jul. 3, 2012; U.S. Pat. No. 7,958,585, PREPRIMITIVE STREAK AND MESENDODERM CELLS, issued Jul. 26, 2011; U.S. Pat. Nos. 7,510,876 and 8,216,836 DEFINITIVE ENDODERM, issued Mar. 31, 2009 and Jul. 10, 2012, respectively; U.S. Pat. No. 7,541,185, METHODS FOR IDENTIFYING FACTORS FOR DIFFERENTIATING DEFINITIVE ENDODERM, issued Jun. 2, 2009; U.S. Pat. No. 7,625,753, EXPANSION OF DEFINITIVE ENDODERM, issued Dec. 1, 2009; U.S. Pat. No. 7,695,963, METHODS FOR INCREASING DEFINITIVE ENDODERM PRODUCTION, issued Apr. 13, 2010; U.S. Pat. No. 7,704,738, DEFINITIVE ENDODERM, issued Apr. 27, 2010; U.S. Pat. No. 7,993,916, METHODS FOR INCREASING DEFINITIVE ENDODERM PRODUCTION, issued Aug. 9, 2011; U.S. Pat. No. 8,008,075, STEM CELL AGGREGATE SUSPENSION COMPOSITIONS AND METHODS OF DIFFERENTIATION THEREOF, issued Aug. 30, 2011; U.S. Pat. No. 8,178,878, COMPOSITIONS AND METHODS FOR SELF-RENEWAL AND DIFFERENTIATION IN HUMAN EMBRYONIC STEM CELLS, issued May 29, 2012; U.S. Pat. No. 8,216,836, METHODS FOR IDENTIFYING FACTORS FOR DIFFERENTIATING DEFINITIVE ENDODERM, issued Jul. 10, 2012; U.S. Pat. Nos. 7,534,608, 7,695,965, and 7,993,920 issued May 19, 2009, Apr. 13, 2010; and Aug. 9, 2011, respectively; U.S. Pat. No. 8,129,182, ENDOCRINE PRE- CURSOR CELLS, PANCREATIC HORMONEEXPRESSING CELLS AND METHODS OF PRODUCTION, issued Mar. 6, 2012; U.S. Pat. No. 8,338,170 METHODS FOR PURIFYING ENDODERM AND PANCREATIC ENDODERM CELLS DERIVED FROM HUMAN EMBRYONIC STEM CELLS, issued Dec. 25, 2012; U.S. Pat. No. 8,334,138, METHODS AND COMPOSITIONS FOR FEEDER-FREE PLURIPOTENT STEM CELL MEDIA CONTAINING HUMAN SERUM, issued Dec. 18, 2012; U.S. Pat. No. 8,278,106, ENCAPSULATION OF PANCREATIC CELLS DERIVED FROM HUMAN PLURIPOTENT STEM CELLS, issued Oct. 2, 2012; U.S. Pat. No. 8,338,170, titled METHOD FOR PURIFYING ENDODERM AND PANCREATIC ENDODERM CELLS DERIVED FROM HUMAN EMBRYONIC STEM CELLS (CYTHERA.063A), issued Dec. 25, 2012; U.S. application Ser. No. 13/761,078, CELL COMPOSITIONS DERIVED FROM DEDIFFERENTIATED REPROGRAMMED CELLS, filed Feb. 6, 2013; U.S. application Ser. No. 13/672,688, SCALABLE PRIMATE PLURIPOTENT STEM CELL AGGREGATE SUSPENSION CULTURE AND DIFFERENTIATION THEREOF, filed Nov. 8, 2012; U.S. application Ser. No. 14/106,330, IN VITRO DIFFERENTIATION OF PLURIPOTENT STEM CELLS TO PANCREATIC ENDODERM CELLS (PEC) AND ENDOCRINE CELLS, filed Dec. 13, 2013; and Design patent applications 29/408,366; 29/408,368 and 29/408,370 filed Dec. 12, 2001 and 29/423,365 May 31, 2012.

Definitions

It will be appreciated that the numerical ranges expressed herein include the endpoints set forth and describe all integers between the endpoints of the stated numerical range.

Unless otherwise noted, the terms used herein are to be understood according to conventional usage by those of ordinary skill in the relevant art. Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The practice of embodiments described herein employs, unless otherwise indicated, conventional techniques of cell biology, molecular biology, genetics, chemistry, microbiology, recombinant DNA, and immunology.

It is to be understood that as used herein and in the appended claims, the singular forms "a," "an," and "the," include plural referents unless the context clearly indicates otherwise. Thus, for example, reference to "a cell" includes one or more of such different cells and reference to "the method" includes reference to equivalent steps and methods known to those of ordinary skill in the art that could be modified or substituted for the methods described herein.

The term "cell" as used herein also refers to individual cells, cell lines, or cultures derived from such cells. A "culture" refers to a composition comprising isolated cells of the same or a different type.

As used herein, the phrase "totipotent stem cells" refer to cells having the ability to differentiate into all cells constituting an organism, such as cells that are produced from the fusion of an egg and sperm cell. Cells produced by the first few divisions of the fertilized egg can also be totipotent. These cells can differentiate into embryonic and extraembryonic cell types. Pluripotent stem cells, such as ES cells for example, can give rise to any fetal or adult cell type. However, alone they cannot develop into a fetal or adult animal because they lack the potential to develop extraembryonic tissue. Extraembryonic tissue is, in part, derived from extraembryonic endoderm and can be further classified into parietal endoderm (Reichert's membrane) and visceral endoderm (forms part of the yolk sac). Both parietal and visceral endoderm support developments of the embryo but do not themselves form embryonic structures. There also exist other extraembryonic tissue including extraembryonic mesoderm and extraembryonic ectoderm.

In some embodiments, a "pluripotent cell" is used as the starting material for differentiation to endoderm-lineage, or more particularly, to pancreatic endoderm type cells. As used herein, "pluripotency" or "pluripotent cells" or equivalents thereof refers to cells that are capable of both proliferation in cell culture and differentiation towards a variety of lineage-restricted cell populations that exhibit multipotent properties, for example, both pluripotent ES cells and induced pluripotent stem (iPS) cells can give rise to each of the three embryonic cell lineages. Pluripotent cells, however, may not be capable of producing an entire organism. That is, pluripotent cells are not totipotent.

In certain embodiments, the pluripotent cells used as starting material are stem cells, including hES cells, hEG cells, iPS cells, even parthenogenic cells and the like. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Still in another embodiment, pluripotent cells are not derived or are not immediately derived from embryos, for example, iPS cells are derived from a non-pluripotent cell, e.g., a multipotent cell or terminally differentiated cell.

Human pluripotent stem cells can also be defined or characterized by the presence of several transcription factors and cell surface proteins including transcription factors Oct-4, Nanog, and Sox-2, which form the core regulatory complex ensuring the suppression of genes that lead to differentiation and the maintenance of pluripotency; and cell surface antigens, such as the glycolipids SSEA3, SSEA4 and the keratan sulfate antigens, Tra-1-60 and Tra-1-81.

As used herein, the phrase "induced pluripotent stem cells," or "iPS cells" or "iPSCs", refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes or gene products, referred to as reprogramming factors. See Takahashi et al., Cell 131:861-872 (2007); Wernig et al., Nature 448:318-324 (2007); Park et al., Nature 451:141-146 (2008), which are herein incorporated by reference in their entireties. Induced pluripotent stem cells are substantially similar to natural human pluripotent stem cells, such as hES cells, in many respects including, the expression of certain stem cell genes and proteins, chromatin methylation patterns, doubling time, embryoid body formation, teratoma formation, viable chimera formation, and potency and differentiability. Human iPS cells provide a source of pluripotent stem cells without the associated use of embryos.

Various methods can be employed to produce iPS cells, which are well known in the art. However, all the methodologies employ certain reprogramming factors comprising expression cassettes encoding Sox-2, Oct-4, Nanog and optionally Lin-28, or expression cassettes encoding Sox-2, Oct-4, Klf4 and optionally c-myc, or expression cassettes encoding Sox-2, Oct-4, and optionally Esrrb. Nucleic acids encoding these reprogramming factors can be in the same expression cassette, different expression cassettes, the same reprogramming vector, or different reprogramming vectors. Oct-3/4 and certain members of the Sox gene family (Sox-1, Sox-2, Sox-3, and Sox-15) are crucial transcriptional regulators involved in the induction process whose absence makes induction impossible. Oct-3/4 (Pou5f1) is one of the family of octamer ("Oct") transcription factors, and plays an important role in maintaining pluripotency. For example, the absence of Oct-3/4 in normally Oct-3/4+ cells, such as blastomeres and embryonic stem cells, leads to spontaneous trophoblast differentiation; whereas the presence of Oct-3/4 gives rise to the pluripotency and differentiation potential of embryonic stem cells. Also, other genes in the "Oct" family, for example, Oct1 and Oct6, do not induce pluripotency, therefore this pluripotency induction process can be attributed to Oct-3/4. Another family of genes associated with maintaining pluripotency similar to Oct-3/4, is the Sox family. However, the Sox family is not exclusive to pluripotent cell types but is also associated with multipotent and unipotent stem cells. The Sox family has been found to work as well in the induction process. Initial studies by Takahashi et al., 2006 supra used Sox2. Since then, Sox1, Sox3, Sox15, and Sox18 genes have also generated iPS cells. Klf4 of the Klf family of genes (Klf-1, Klf2, Klf4, and Klf5) was initially identified by Yamanaka et al. 2006 supra as a factor for the generation of mouse iPS cells. Human iPS cells from S. Yamanaka were used herein to explore cell therapeutic applications of hIPS cells. However, Yu et al. 2007 supra reported that Klf4 was not required and in fact failed to produce human iPS cells. Other members of the Klf family are capable generating iPS cells, including Klf1, Klf2 and Klf5. Lastly, the Myc family (C-myc, L-myc, and N-myc), proto-oncogenes implicated in cancer; c-myc was a factor implicated in the generation of mouse and human iPS cells, but Yu et al. (2007 supra reported that c-myc was not required for generation of human iPS cells.

As used herein, "multipotency" or "multipotent cell" or equivalents thereof refers to a cell type that can give rise to a limited number of other particular cell types. That is, multipotent cells are committed to one or more embryonic cell fates, and thus, in contrast to pluripotent cells, cannot give rise to each of the three embryonic cell lineages as well as to extraembryonic cells. Multipotent somatic cells are more differentiated relative to pluripotent cells, but are not terminally differentiated. Pluripotent cells therefore have a higher potency than multipotent cells. Potency-determining factors that can reprogram somatic cells or used to generate iPS cells include, but are not limited to, factors such as Oct-4, Sox2, FoxD3, UTF1, Stella, Rex1, ZNF206, Sox15, Myb12, Lin28, Nanog, DPPA2, ESG1, Otx2 or combinations thereof.

Embodiments described herein are directed to methods of preserving cell aggregates or implantable, semipermeable devices or encapsulated cell aggregates.

Current cell cryopreservation protocols relate generally to single cells in suspension. The present application teaches, among other things, cryopreserving (1) hES derived cell aggregates, (2) implantable, semipermeable devices and (3) encapsulated hES derived cell aggregates. Specifically, the present application teaches, among other things, cryopreserving (1) PEC aggregates, (2) implantable, semipermeable devices and (3) encapsulated PEC aggregates ("VC combination product"). Cryopreserving cell aggregates has additional challenges not present when cryopreserving single cells. For example, the cell aggregates are not uniform in shape, size or density. When the cell aggregates are exposed to a cryopreservant, cells on the outside of the aggregate are exposed to more of the toxic cryopreservant than cells on the inside of the aggregate. If the aggregate is not exposed to enough cryopreservant, for sufficient time, the cells in the middle of the aggregate may not be exposed to enough cryopreservant resulting in cell death when exposed to extreme cold. Variations in the aggregate size and density make it difficult to utilize a single method effective for all cell aggregates. Problems associated with variations in cell aggregate shape, size or density could be alleviated if cell aggregates could be made more homogenous or by selecting aggregates of uniform shape, size or density, or by removing aggregates of non-uniform shape, size or density.

Cells can be inserted into implantable semipermeable devices at the point of manufacture or, alternatively, at the clinical site. If the cells are inserted at the point of manufacture or clinical site, the cells can be cryopreserved separately from the device. Then, the cryopreserved cells can be thawed when ready to be used either at the manufacturing or clinical site. Loading an encapsulation device directly at the clinical site has several drawbacks in both safety and cell viability. Cells can leak from the device when the syringe is removed from the port. The syringe's needle can also pierce the wall of the encapsulation device, allowing cells to escape. Such contamination is a safety hazard regulated by the U.S. Food and Drug Administration. Theoretically, even a single contaminating cell could expand and/or biodistribute. Thus, development of a procedure to deliver encapsulated cells to the clinical site is needed. As taught, this problem can be solved in several different ways: cells can be cryopreserved separate from the encapsulation device, thawed when needed, loaded into the encapsulation device and then shipped to the clinical site. Alternatively, encapsulated cells can be cryopreserved and then shipped to the clinical site when needed. The encapsulated cells can be shipped in a cryopreserved or frozen state and thawed prior to use by the medical professional. The encapsulated cells can also be thawed prior to shipment. It may also be useful to cryopreserve the implantable, semipermeable device itself for longer shelf life.

Cryopreserving encapsulated cell aggregates has additional challenges not present when cryopreserving single cells. For example, there can be significant cell death during thawing of cells subsequent to cryopreservation. Living cells have difficulty surviving in such an environment. One of skill in the art will recognize that if cell survival following cryopreservation is increased to greater than 50% or greater than 60%, 70%, 80% 90%, 95%, 98% or more preferably 90-95%, cell death during thawing does not pose as significant an issue.

Some embodiments of the methods of producing insulin described herein can include treating an animal having diabetes, or controlling glucose concentration in the blood of an animal, by providing the animal with pancreatic endoderm cells that can mature in vivo into insulin producing cells that secrete insulin in response to glucose stimulation.

One aspect described herein includes populations of pluripotent or precursor cells that are capable of selectively, and in some aspects selectively reversibly, developing into different cellular lineages when cultured under appropriate conditions. As used herein, the term "population" refers to cell culture of more than one cell having the same identifying characteristics. The term "cell lineage" refers to all of the stages of the development of a cell type, from the earliest precursor cell to a completely mature cell (i.e. a specialized cell). A "precursor cell" or "progenitor cell" can be any cell in a cell differentiation pathway that is capable of differentiating into a more mature cell. As such, a precursor cell can be a pluripotent cell, or it can be a partially differentiated multipotent cell, or reversibly differentiated cell. The term "precursor cell population" refers to a group of cells capable of developing into a more mature or differentiated cell type. A precursor cell population can comprise cells that are pluripotent, cells that are stem cell lineage restricted (i.e. cells capable of developing into less than all ectodermal lineages, or into, for example, only cells of neuronal lineage), and cells that are reversibly stem cell lineage restricted. Therefore, the term "progenitor cell" or "precursor cell" may be a "pluripotent cell" or "multipotent cell."

As used herein, the terms "develop from pluripotent cells", "differentiate from pluripotent cells", "mature from pluripotent cells" or "produced from pluripotent cells", "derived from pluripotent cells", "differentiated from pluripotent cells" and equivalent expressions refer to the production of a differentiated cell type from pluripotent cells in vitro or in vivo, e.g., in the case of endocrine cells matured from transplanted PDX1 pancreatic endoderm cells in vivo as described in International Patent Application No. PCT/US2007/015536, entitled METHODS OF PRODUCING PANCREATIC HORMONES. All such terms refer to the progression of a cell from the stage of having the potential to differentiate into at least two different cellular lineages to becoming a specialized and terminally differentiated cell. Such terms can be used interchangeably for the purposes of the present application. Embodiments described herein contemplate culture conditions that permit such differentiation to be reversible, such that pluripotency or at least the ability to differentiate into more than one cellular lineage can be selectively regained.

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells. In a preferred embodiment, the feeder cell comprises an adherent monolayer.

As used herein, the terms "cluster" and "clump" or "aggregate" can be used interchangeably, and generally refer to a group of cells that have not been dissociated into single cells. The clusters may be dissociated into smaller clusters. This dissociation is typically manual in nature (such as using a Pasteur pipette), but other means of dissociation are contemplated. Aggregate suspension pluripotent or multipotent cell cultures are substantially as described in International Publications PCT/US2007/062755, titled COMPOSITIONS AND METHODS FOR CULTURING DIFFERENTIAL CELLS and PCT/US2008/082356, titled STEM CELL AGGREGATE SUSPENSION COMPOSITIONS AND METHODS OF DIFFERENTIATION THEREOF, which are herein incorporated by reference in their entireties.

Similarly, embodiments in which pluripotent cell cultures or aggregate pluripotent suspension cultures are grown in defined conditions without the use of feeder cells, are "feeder-free". Feeder-free culture methods increase scalability and reproducibility of pluripotent cell culture and reduces the risk of contamination, for example, by infectious agents from the feeder cells or other animal-sourced culture components. Feeder-free methods are also described in U.S. Pat. No. 6,800,480 to Bodnar et al. (assigned to Geron Corporation, Menlo Park, Calif.). However, and in contrast to U.S. Pat. No. 6,800,480 patent, embodiments described herein, whether they be pluripotent, multipotent or differentiated cell cultures, are feeder-free and do not further contain an endogenous or exogenous extracellular-matrix; i.e. the cultures described herein are extracellular-matrix-free as well as being feeder free. For example, in the U.S. Pat. No. 6,800,480, extracellular matrix is prepared by culturing fibroblasts, lysing the fibroblasts in situ, and then washing what remains after lysis. Alternatively, in U.S. Pat. No. 6,800,480 extracellular matrix can also be prepared from an isolated matrix component or a combination of components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Embodiments described herein neither produce an extracellular-matrix by growth of a feeder or fibroblast layer and lysing the cells to produce the extracellular-matrix; nor does it require first coating the tissue culture vessel with extracellular matrix component or a combination of extracellular-matrix components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Hence, the aggregate suspension cultures described herein for pluripotent, multipotent and differentiated cells do not require a feeder layer, a lysed feeder or fibroblast cell to produce an extracellular matrix coating, an exogenously added extracellular matrix or matrix component; rather use of soluble human serum component as described in International Application PCT/US2008/080516, titled METHODS AND COMPOSITIONS FOR FEEDER-FREE PLURIPOTENT STEM CELL MEDIA CONTAINING HUMAN SERUM, which is herein incorporated by reference in its entirety, overcomes the need for either a feeder-cell or feeder monolayer, as well as overcoming the need for an endogenous extracellular-matrix from a feeder or fibroblast cell or from exogenously added extracellular-matrix components.

In preferred embodiments, culturing methods are free of animal-sourced products. In another preferred embodiment, the culturing methods are xeno-free. In even more preferred embodiments, one or more conditions or requirements for the commercial manufacture of human cell therapeutics met or exceeded by the culturing methods described herein.

General methods for production of endoderm lineage cells derived from hES cells are described in related U.S. applications as indicated above, and D'Amour et al. 2005 Nat Biotechnol. 23:1534-41 and D'Amour et al. 2006 Nat Biotechnol. 24(11):1392-401. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm or pancreatic endocrine progenitor production) and stage 5 (results in mostly hormone expressing endocrine cell production.

The term "trophectoderm" refers to a multipotent cell having the relative high expression of markers selected from the group consisting of HAND1, Eomes, MASH2, ESXL1, HCG, KRT18, PSG3, SFXN5, DLX3, PSX1, ETS2, and ERRB genes as compared to the expression levels of HAND1, Eomes, MASH2, ESXL1, HCG, KRT18, PSG3, SFXN5, DLX3, PSX1, ETS2, and ERRB in non-trophectoderm cells or cell populations.

"Extraembryonic endoderm" refers to a multipotent cell having relative high expression levels of markers selected from the group consisting of SOX7, SOX17, THBD, SPARC, DAB1, or AFP genes as compared to the expression levels of SOX7, SOX17, THBD, SPARC, DAB1, or AFP in non-extraembryonic endoderm cells or cell populations.

The term "Preprimitive streak cells" refers to a multipotent cell having relative high expression levels of the FGF8 and/or NODAL marker genes, as compared to BRACHURY low, FGF4 low, SNAI1 low, SOX17 low, FOXA2 low, SOX7 low and SOX1 low.

The term "Mesendoderm cell" refers to a multipotent cell having relative high expression levels of brachyury, FGF4, SNAI1 MIXL1 and/or WNT3 marker genes, as compared to SOX17 low, CXCR4 low, FOXA2 low, SOX7 low and SOX1 low.

The term "Definitive endoderm (DE)" refers to a multipotent endoderm lineage cell that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from SOX17, CXCR4, MIXL1, GATA4, HNF3β, GSC, FGF17, VWF, CALOR, FOXQ1, CMKOR1 and CRIP1 are expressed in definitive endoderm cells. In other embodiments, one or more markers selected from OCT4, alpha-fetoprotein (AFP), Thrombomodulin (TM), SPARC, SOX7 and HNF4alpha are not expressed or significantly expressed in definitive endoderm cells. Definitive endoderm cell populations and methods of production thereof are also described in U.S. application Ser. No. 11/021,618, entitled DEFINITIVE ENDODERM, filed Dec. 23, 2004.

Still other embodiments relate to cell cultures termed "PDX1-negative foregut endoderm cells" or "foregut endoderm cells" or equivalents thereof. In some embodiments, the foregut endoderm cells express SOX17, HNF1β (HNF1B), HNF4alpha (HNF4A) and FOXA1 markers but do not substantially express PDX1, AFP, SOX7, or SOX1. PDX1-negative foregut endoderm cell populations and methods of production thereof are also described in U.S. application Ser. No. 11/588,693, entitled PDX1-expressing dorsal and ventral foregut endoderm, filed Oct. 27, 2006.

Other embodiments described herein relate to cell cultures of "PDX1-positive, dorsally-biased, foregut endoderm cells" (dorsal PDX1-positive foregut endoderm cells) or just "PDX1-positive endoderm." In some embodiments, the PDX1-positive endoderm cells express one or more markers selected from Table 1 and/or one or more markers selected from Table 2, also described in related U.S. application Ser. No. 11/588,693 entitled PDX1 EXPRESSING DOSAL AND VENTRAL FOREGUT ENDODERM, filed Oct. 27, 2006, and also U.S. application Ser. No. 11/115,868, entitled PDX1-expressing endoderm, filed Apr. 26, 2005.

The PDX1-positive foregut endoderm cells, such as those produced according to the methods described herein, are progenitors which can be used to produce fully differentiated pancreatic hormone secreting or endocrine cells, e.g., insulin-producing (3-cells. In some embodiments of the present invention, PDX1-positive foregut endoderm cells are produced by differentiating definitive endoderm cells that do not substantially express PDX1 (PDX1-negative definitive endoderm cells; also referred to herein as definitive endoderm) so as to form PDX1-positive foregut endoderm cells.

As used herein, "pancreatic endoderm," "pancreatic epithelial," "pancreatic epithelium" (all can be abbreviated "PE") "pancreatic progenitor," "PDX-1 positive pancreatic endoderm or equivalents thereof, such as pancreatic endoderm cells ("PEC"), are all precursor or progenitor pancreatic cells. PEC as described herein is a progenitor cell population after stage 4 differentiation (about day 12-14) and includes at least two major distinct populations: i) pancreatic progenitor cells that express NKX6.1 but do not express CHGA (or CHGA negative, CHGA−); and ii) polyhormonal endocrine cells that express CHGA (CHGA positive, CHGA+). Without being bound by theory, the cell population that expresses NKX6.1 but not CHGA is hypothesized to be the more active or therapeutic component of PEC, whereas the population of CHGA− positive polyhormonal endocrine cells is hypothesized to further differentiate and mature in vivo into glucagon-expressing islet cells. See Kelly et al. (2011) Cell-surface markers for the isolation of pancreatic cell types derived from human embryonic stem cells, *Nat Biotechnol.* 29(8):750-756, published online 31 Jul. 2011 and Schulz et al. (2012), A Scalable System for Production of Functional Pancreatic Progenitors from Human Embryonic Stem Cells, PLosOne 7(5): 1-17, e37004.

Still, sometimes, pancreatic endoderm cells are used without reference to PEC as described just above, but to refer to at least stages 3 and 4 type cells in general. The use and meaning will be clear from the context. Pancreatic endoderm derived from pluripotent stem cells, and at least hES and hIPS cells, in this manner are distinguished from other endodermal lineage cell types based on differential or high levels of expression of markers selected from PDX1, NKX6.1, PTF1A, CPA1, cMYC, NGN3, PAX4, ARX and NKX2.2 markers, but do not substantially express genes which are hallmark of pancreatic endocrine cells, for example, CHGA, INS, GCG, GHRL, SST, MAFA, PCSK1 and GLUT1. Additionally, some "endocrine progenitor cells" expressing NGN3 can differentiate into other non-pancreatic structures (e.g., duodenum). In one embodiment, the NGN3 expressing endocrine progenitor described herein differentiates into mature pancreatic lineage cells, e.g., pancreatic endocrine cells. Pancreatic endoderm or endocrine progenitor cell populations and methods thereof are also described in U.S. patent application Ser. No. 11/773,944, entitled Methods of producing pancreatic hormones, filed Jul. 5, 2007, and U.S. patent application Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008.

As used herein, "endocrine precursor cell" refers to a multipotent cell of the definitive endoderm lineage that expresses neurogenin 3 (NEUROG3) and which can further differentiate into cells of the endocrine system including, but not limited to, pancreatic islet hormone-expressing cells.

Endocrine precursor cells cannot differentiate into as many different cell, tissue and/or organ types as compared to less specifically differentiated definitive endoderm lineage cells, such as PDX1-positive pancreatic endoderm cell.

As used herein, "pancreatic islet hormone-expressing cell," "pancreatic endocrine cell," or equivalents thereof refer to a cell, which has been derived from a pluripotent cell in vitro, which can be polyhormonal or singly-hormonal. The endocrine cells can therefore express one or more pancreatic hormones, which have at least some of the functions of a human pancreatic islet cell. Pancreatic islet hormone-expressing cells can be mature or immature. Immature pancreatic islet hormone-expressing cells can be distinguished from mature pancreatic islet hormone-expressing cells based on the differential expression of certain markers, or based on their functional capabilities, e.g., glucose responsiveness.

As used herein, "immature beta cells" or "immature endocrine cells" or "immature beta cells" or equivalents thereof refers to endocrine cell populations made in vitro which are capable of functioning in vivo, i.e., when transplanted secrete insulin in response to blood glucose. Properly specified endocrine cells or stage 7 cultures may have additional characteristics including the following: When transplanted, properly specified endocrine cells may develop and mature to functional pancreatic islet cells. Properly specified endocrine cells may be enriched for endocrine cells (or depleted of non-endocrine cells). In a preferred embodiment greater than about 50% of the cells in the properly specified endocrine cell population are CHGA+. In a more preferred embodiment greater than about 60% or 70% or 80% or 90% or 95% or 98% or 100% of the cells in the properly specified endocrine cell population are CHGA+. In a preferred embodiment less than about 50% of the cells in the properly specified endocrine cell population are CHGA−. In a more preferred embodiment less than about 15% of the cells in the properly specified endocrine cell population are CHGA−. In a more preferred embodiment less than about 10% or 5% or 3% or 2% or 1% or 0.5% or 0% of the cells in the properly specified endocrine cell population are CHGA−. Further, expression of certain markers may be suppressed in properly specified endocrine cells such as NGN3 expression during stage 3. Properly specified endocrine cells may have increased expression of NGN3 at stage 5. Properly specified endocrine cells may be singly-hormonal (e.g. INS only, GCG only or SST only). Properly specified endocrine cells may co-express other immature endocrine cell markers including NKX6.1 and PDX1. Properly specified endocrine cells may be both singly-hormonal and co-express other immature endocrine cell markers including NKX6.1 and PDX1. Properly specified endocrine cells may have more singly hormone expressing INS cells as a percentage of the total INS population. In a preferred embodiment properly specified endocrine cells have at least 50% singly hormone expressing INS cells as a percentage of the total INS population. Properly specified endocrine cells may be CHGA+/INS+/NKX6.1+ (triple positive). In a preferred embodiment greater than about 25% of the cells in the cell population are CHGA+/INS+/NKX6.1+ (triple positive). In a preferred embodiment greater than about 30% or 40% or 50% or 60% or 70% or 80% or 90% or 95% 100% of the cells in the cell population are CHGA+/INS+/NKX6.1+ (triple positive).

The term "immature endocrine cell,", specifically an "immature beta-cell," or equivalents thereof refer to a cell derived from any other endocrine cell precursor including an endocrine progenitor/precursor cell, a pancreatic endoderm (PE) cell, a pancreatic foregut cell, a definitive endoderm cell, a mesendoderm cell or any earlier derived cell later described, that expresses at least a marker selected from the group consisting of INS, NKX6.1, PDX1, NEUROD, MNX1, NKX2.2, MAFA, PAX4, SNAIL2, FOXA1 or FOXA2. Preferably, an immature beta-cell described herein expresses, INS, NKX6.1 and PDX1, and more preferably it co-expresses INS and NKX6.1. The terms "immature endocrine cell," "immature pancreatic hormone-expressing cell," or "immature pancreatic islet" or equivalents thereof refer to a unipotent immature beta cell, or pre-beta cell, and do not include other immature cells, for example, the terms do not include an immature alpha (glucagon) cell, or an immature delta (somatostatin) cell, or an immature epsilon (ghrelin) cell, or an immature pancreatic polypeptide (PP). Immature endocrine and immature beta cells are described in more detail in Applicants U.S. application No., ENCAPSULATION OF PANCREATIC CELLS DERIVED FROM HUMAN PLURIPOTENT STEM CELLS, filed Dec. 13, 2013.

The term "essentially" or "substantially" means either a de minimus or a reduced amount of a component or cell present in any cell aggregate suspension type, e.g., cell aggregates in suspension described herein are "essentially or substantially homogenous", "essentially or substantially homo-cellular" or are comprised of "essentially hES cells", "essentially or substantially definitive endoderm cells", "essentially or substantially foregut endoderm cells", "essentially or substantially PDX1-negative foregut endoderm cells", "essentially or substantially PDX1-positive pre-pancreatic endoderm cells", "essentially or substantially PDX1-positive pancreatic endoderm or progenitor cells", "essentially or substantially PDX1-positive pancreatic endoderm tip cells", "essentially or substantially pancreatic endocrine precursor cells", "essentially or substantially pancreatic endocrine cells" and the like.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

Cell cultures can be grown in medium containing reduced serum or substantially free of serum or no serum. Under certain culture conditions, serum concentrations can range from about 0% (v/v) to about 10% (v/v). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v) or less than about 10% (v/v). In some processes, preprimitive streak cells are grown without serum or without serum replacement. In still other processes, preprimitive streak cells are grown in the presence of B27. In such processes, the concentration of B27 supplement can range from about 0.1% (v/v) to about 20% (v/v).

As used herein, "exogenously added," compounds such as growth factors, differentiation factors, and the like, in the context of cultures or conditioned media, refers to growth factors that are added to the cultures or media to supplement any compounds or growth factors that may already be present in the culture or media. For example, in some embodiments, cells cultures and or cell populations do not include an exogenously-added retinoid.

As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 amu).

The progression of pluripotent cells to various multipotent and/or differentiated cells can be monitored by determining the relative expression of genes, or gene markers, characteristic of a specific cell, as compared to the expression of a second or control gene, e.g., housekeeping genes. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest.

The terms fibroblast growth factor 7 (FGF7) and keratinocyte growth factor (KGF) are synonymous.

Methods for Production of Induced Pluripotent Stem (iPS) Cells

Embodiments described herein are not limited to any one type of iPS cell or any one method of producing the iPS cell. Embodiments are not limited or dependent on levels of efficiency of production of the iPS cells, because various methods exist. Embodiments described herein apply to differentiation of iPS cells into endoderm-lineage cells and uses thereof.

Embodiments of the compositions and methods described herein contemplate the use of various differentiable primate pluripotent stem cells including human pluripotent stem cells such as hESC, including but not limited to, CyT49, CyT212, CyT203, CyT25, (commercially available at least at the time of filing of this instant application from ViaCyte Inc. located at 3550 General Atomics Court, San Diego Calif. 92121) BGO1, BG02 and MEL1, and induced pluripotent stem (iPS) cells such as iPSC-482c7 and iPSC-603 (Cellular Dynamics International, Inc., Madison, Wis.) and iPSC-G4 (hereinafter "G4") and iPSC-B7 (hereinafter, "B7") (Shinya Yamanaka, Center for iPS Cell Research, Kyoto University); studies using G4 and B7 are described in detail herein. Certain of these human pluripotent stem cells are registered with national registries such as the National Institutes of Health (NIH) and listed in the NIH Human Stem Cell Registry (e.g., CyT49 Registration No. #0041). Information on CyT49, other available cell lines can also be found on the worldwide web at stemcells.nih.gov/research/registry. Still other cell lines, e.g., BG01 and BG01v, are sold and distributed to third parties by WiCell®, an affiliate of the Wisconsin International Stem Cell (WISC) Bank (Catalog name, BG01) and ATCC (Catalog No. SCRC-2002), respectively. While other cell lines described herein may not be registered or distributed by a biological repository, such as WiCell® or ATCC, such cell lines are available to the public directly or indirectly from the principle investigators, laboratories and/or institutions. Public requests for cell lines and reagents, for example, are customary for those skilled in the art in the life sciences. Typically, transfer of these cells or materials is by way of a standard material transfer agreement between the proprietor of the cell line or material and the recipient. These types of material transfers occur frequently in a research environment, particularly in the life sciences. In fact, Applicant has routinely transferred cells since the time they were derived and characterized, including CyT49 (2006), CyT203 (2005), Cyt212 (2009), CyT25 (2002), BG01 (2001), BGO02 (2001), BG03 (2001) and BG01v (2004), through such agreements with commercial and non-profit industry partners and collaborators. The year in parenthesis next to each cell line in the previous list indicates the year when the cell lines or materials became publically available and immortal (e.g. cell banks were made) and thus destruction of another embryo has not been performed or required since the establishment of these cell lines in order to make the compositions and practice the methods described herein.

In August 2006, Klimanskaya et al. demonstrated that hESC can be derived from single blastomeres, hence keeping the embryo intact and not causing their destruction. Biopsies were performed from each embryo using micromanipulation techniques and nineteen (19) ES-cell-like outgrowths and two (2) stable hESC lines were obtained. These hESC lines were able to be maintained in an undifferentiated state for over six (6) months, and showed normal karyotype and expression of markers of pluripotency, including Oct-4, SSEA-3, SSEA-4, TRA-1-60, TRA-1-81, Nanog and Alkaline Phosphatase. These hESC can differentiate and form derivatives of all three (3) embryonic germ layers both in vitro and form in teratomas in vivo. These methods to create new stem cell lines without destruction of embryos addresses the ethical concerns of using human embryos. See Klimanskaya et al. (2006) Nature 444:481-5, Epub 2006 Aug. 23. However, Klimanskaya et al. co-cultured the derived hESC line with other hESC. Later, in 2008, Chung Y. et al., were able to obtain hES cell lines again from a single blastomere but without co-culture with hESC. See Chung Y. et al., *Cell Stem Cell* 2008, 2(2), 113-117. Thus the compositions and methods described herein, and in particular, the such compositions and methods as related to induced pluripotent stem cells or genetically dedifferentiated pluripotent stem cells, do not require the destruction of a human embryo.

Tables 3 and 4 are non-exhaustive lists of certain iPSC and hESCs, respectively, which are available worldwide for research and/or commercial purposes, and are suitable for use in the methods and compositions of the present invention. The information in Tables 3 and 4 were derived from the literature and publically available databases including, for example, the National Institutes of Health (NIH) Human Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

Human iPSC described herein (at least iPSC-603 and iPSC-482-c7) were provided by Cellular Dynamics International, Inc. (Madison, Wis., USA).

TABLE 3

| Listing of human induced pluripotent stem (hIPS) cell lines | |
|---|---|
| University of Wisconsin - Madison (USA) | 1. IPS(FORESKIN)-1 (Normal; 46XY; Yu, J., et al. [Thomson] Science. 2007 Induced pluripotent stem cell lines derived from human somatic cells 318(5858): 1917-20.)<br>2. IPS(FORESKIN)-2 (Normal; 46XY; Yu, J., et al. [Thomson] Science. 2007 Induced pluripotent stem cell lines derived from human somatic cells 318(5858): 1917-20.)<br>3. IPS(FORESKIN)-3 (Normal; 46XY; Yu, J., et al. [Thomson] Science. 2007 Induced pluripotent stem cell lines derived from human somatic cells 318(5858): 1917-20.)<br>4. IPS(FORESKIN)-4 (Normal; 46XY; Yu, J., et al. [Thomson] Science. 2007 Induced pluripotent stem cell lines derived from human somatic cells 318(5858): 1917-20.)<br>5. IPS(IMR90)-1 (Normal; 46XX; Yu, J., et al. [Thomson] Science. 2007 Induced pluripotent stem cell lines derived from human somatic cells 318(5858): 1917-20.)<br>6. IPS(IMR90)-2 (Normal; 46XX; Yu, J., et al. [Thomson] Science. 2007 Induced pluripotent stem cell lines derived from human somatic cells 318(5858): 1917-20.)<br>7. IPS(IMR90)-3 (Normal; 46XX; Yu, J., et al. [Thomson] Science. 2007 Induced pluripotent stem cell lines derived from human somatic cells 318(5858): 1917-20.)<br>8. IPS(IMR90)-4 (Normal; 46XX; Yu, J., et al. [Thomson] Science. 2007 Induced pluripotent stem cell lines derived from human somatic cells 318(5858): 1917-20.)<br>9. IPS-SMA-3.5 (Normal; 46XY; Type 1 Spinal Muscular Atrophy; Ebert, A. D., et al. 2009. Induced pluripotent stem cells from a spinal muscular atrophy patient Nature. 457: 277-80)<br>10. IPS-SMA-3.6 (Normal; 46XY; Type 1 Spinal Muscular Atrophy; Ebert, A. D., et al. 2009. Induced pluripotent stem cells from a spinal muscular atrophy patient Nature. 457: 277-80)<br>11. IPS-WT (Normal; 46XX; Type 1 Spinal Muscular Atrophy; Ebert, A. D., et al. 2009. Induced pluripotent stem cells from a spinal muscular atrophy patient Nature. 457: 277-80) |
| University of California, Los Angeles (USA) | 1. IPS-1 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblasts Proc Natl Acad Sci USA. 105: 2883-8)<br>2. IPS-2 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblastsProc Natl Acad Sci USA. 105: 2883-8)<br>3. IPS-5 (Lowry, W. E., et al. 2008. Generation of human induced pluripotent stem cells from dermal fibroblasts Proc Natl Acad Sci USA. 105: 2883-8)<br>4. IPS-7 (Lowry, W. E., et al. 2008. Generation of human induced pluripotent stem cells from dermal fibroblasts Proc Natl Acad Sci USA. 105: 2883-8)<br>5. IPS-18 (Karumbayaram, S. et al. 2009. Directed Differentiation of Human-Induced Pluripotent Stem Cells Generates Active Motor NeuronsStem Cells. 27: 806-811; Lowry, W. E., et al. 2008. Generation of human induced pluripotent stem cells from dermal fibroblastsProc Natl Acad Sci USA. 105: 2883-8)<br>6. IPS-24 (Lowry, W. E., et al. 2008. Generation of human induced pluripotent stem cells from dermal fibroblasts Proc Natl Acad Sci USA. 105: 2883-8)<br>7. IPS-29 (Lowry, W. E., et al. 2008. Generation of human induced pluripotent stem cells from dermal fibroblasts Proc Natl Acad Sci USA. 105: 2883-8) |
| Mt. Sinai Hospital (Samuel Lunenfeld Research Institute; USA) | 1. 60 (Woltjen, K. et al. 2009. PiggyBac transposition reprograms fibroblasts to induced pluripotent stem cells Nature. 458(7239): 766-70)<br>2. 61 (Woltjen, K. et al. 2009. PiggyBac transposition reprograms fibroblasts to induced pluripotent stem cells Nature. 458(7239): 766-70)<br>3. 66 (Woltjen, K. et al. 2009. PiggyBac transposition reprograms fibroblasts to induced pluripotent stem cells Nature 458(7239): 766-70)<br>4. 67 (Woltjen, K. et al. 2009. PiggyBac transposition reprograms fibroblasts to induced pluripotent stem cells Nature 458(7239): 766-70) |

TABLE 3-continued

Listing of human induced pluripotent stem (hIPS) cell lines

|  |  |
|---|---|
|  | 5. HIPSC117 (Kaji K, et al. 2009 Virus-free induction of pluripotency and subsequent excision of reprogramming factors Nature 458(7239): 771-5) |
|  | 6. HIPSC121 (Kaji K, et al. 2009 Virus-free induction of pluripotency and subsequent excision of reprogramming factors Nature 458(7239): 771-5) |
|  | 7. HIPSC122 (Kaji K, et al. 2009 Virus-free induction of pluripotency and subsequent excision of reprogramming factors Nature 458(7239): 771-5) |
| Children's Hospital - Boston (USA) | 1. 551-IPS8 (Park IH, et al. 2008. Reprogramming of human somatic cells to pluripotency with defined factors Nature 451: 141-6). |
|  | 2. ADA-IPS2 ((ADA-SCID) Adenosine Deaminase Deficiency-related Severe Combined Immunodeficiency (GGG>AGG, exon 7, ADA gene); Park, I. H. et al. 2008. Disease-Specific Induced Pluripotent Stem Cells Cell 134(5): 877-86) |
|  | 3. ADA-IPS3 ((ADA-SCID) Adenosine Deaminase Deficiency-related Severe Combined Immunodeficiency (GGG>AGG, exon 7, ADA gene); Park, I. H. et al. 2008. Disease-Specific Induced Pluripotent Stem Cells Cell 134(5): 877-86) |
|  | 4. BJ1-IPS1 (Park, I. H. et al. 2008. Disease-Specific Induced Pluripotent Stem Cells Cell 134(5): 877-86) |
|  | 5. BMD-IPS1 (Male; (BMD) Becker Muscular Dystrophy (Unidentified mutation in dystrophin); Park, I. H. et al. 2008. Disease-Specific Induced Pluripotent Stem Cells Cell 134(5): 877-86) |
|  | 6. BMD-IPS4 (Normal; 46XY; (BMD) Becker Muscular Dystrophy (Unidentified mutation in dystrophin); Park, I. H. et al. 2008. Disease-Specific Induced Pluripotent Stem Cells Cell 134(5): 877-86) |
|  | 7. DH1CF16-IPS1 (Normal; 46XY; Park, I. H. et al. 2008. Disease-Specific Induced Pluripotent Stem Cells Cell 134(5): 877-86) |
|  | 8. DH1CF32-IPS2 (Male; Park, I. H. et al. 2008. Disease-Specific Induced Pluripotent Stem Cells Cell 134(5): 877-86) |
|  | 9. DH1F-IPS3-3(Normal; 46XY; Park, I. H. et al. 2008. Disease-Specific Induced Pluripotent Stem Cells Cell 134(5): 877-86) |
|  | 10. DMD-IPS1 ((Normal; 46XY; DMD) Duchenne Muscular Dystrophy (Deletion of exon 45-52, dystrophin gene; Park, I. H. et al. 2008. Disease-Specific Induced Pluripotent Stem Cells Cell 134(5): 877-86) |
|  | 11. DMD-IPS2 (Male; (DMD) Duchenne Muscular Dystrophy (Deletion of exon 45-52, dystrophin gene; Park, I. H. et al. 2008. Disease-Specific Induced Pluripotent Stem Cells Cell 134(5): 877-86) |
|  | 12. DS1-IPS4 (Male; Down syndrome (Trisomy 21); Park, I. H. et al. 2008. Disease-Specific Induced Pluripotent Stem Cells Cell 134(5): 877-86) |
|  | 13. DS2-IPS1 (Male; Down syndrome (Trisomy 21); Park, I. H. et al. 2008. Disease-Specific Induced Pluripotent Stem Cells Cell 134(5): 877-86) |
|  | 14. DS2-IPS10 (Male; Down syndrome (Trisomy 21); Park, I. H. et al. 2008. Disease-Specific Induced Pluripotent Stem Cells Cell 134(5): 877-86) |
|  | 15. GD-IPS1(Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5): 877-86) |
|  | 16. GD-IPS3 (Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5): 877-86) |
|  | 17. HFIB2-IPS2 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 18. HFIB2-IPS4 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 19. HFIB2-IPS5 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature 451: 141-6) |
|  | 20. JDM-IPS1 (Normal, 46XX; Juvenile diabetes mellitus (multifactorial); Park, I. H. et al. 2008. Disease-Specific Induced Pluripotent Stem Cells Cell 134(5): 877-86) |
|  | 21. JDM-IPS1 (Normal, 46XX; Juvenile diabetes mellitus (multifactorial); Park, I. H. et al. 2008. Disease-Specific Induced Pluripotent Stem Cells Cell 134(5): 877-86) |

TABLE 3-continued

Listing of human induced pluripotent stem (hIPS) cell lines

|  |  |
|---|---|
|  | 22. JDM-IPS2 (Female; Juvenile diabetes mellitus (multifactorial); Park, I. H. et al. 2008. Disease-Specific Induced Pluripotent Stem Cells Cell 134(5): 877-86)
23. JDM-IPS3 (Female; Juvenile diabetes mellitus (multifactorial); Park, I. H. et al. 2008. Disease-Specific Induced Pluripotent Stem Cells Cell 134(5): 877-86)
24. LNSC-IPS2 (Female; Lesch-Nyhan syndrome (carrier, heterozygosity of HPRT1; Park, I. H. et al. 2008. Disease-Specific Induced Pluripotent Stem Cells Cell 134(5): 877-86)
25. MRC5-IPS7 (Male; Park, I. H. et al. 2008. Disease-Specific Induced Pluripotent Stem Cells Cell 134(5): 877-86)
26. MRC5-IPS12 (Normal; 46XY; Park, I. H. et al. 2008. Disease-Specific Induced Pluripotent Stem Cells Cell 134(5): 877-86)
27. MRC5-IPS1 (Male; Park, I. H. et al. 2008. Disease-Specific Induced Pluripotent Stem Cells Cell 134(5): 877-86)
28. PD-IPS1 (Male; Parkinson disease (multifactorial); Park, I. H. et al. 2008. Disease-Specific Induced Pluripotent Stem Cells Cell 134(5): 877-86)
29. SBDS-IPS1 (Male; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5): 877-86)
30. SBDS-IPS2
31. SBDS-IPS3 (Normal; 46XY; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5): 877-86) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21)
2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21)
3. A29c (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science 321: 1218-21) |
| Salk Institute (USA) | 1. HAIR-IPS1 (Aasen, T., et al [Belmonte, J. C.] 2008. Efficient and rapid generation of induced pluripotent stem cells from human keratinocytes Nat Biotechnol 26: 1276-84)
2. HAIR-IPS2 (Aasen, T., et al [Belmonte, J. C.] 2008. Efficient and rapid generation of induced pluripotent stem cells from human keratinocytes Nat Biotechnol 26: 1276-84) |
| Royan Institute (Iran) | 1. R.1.H.iPSC.1(OCT4, Sox2, KLF4, c-Myc; Human fibroblasts)
2. BOM.1.H.iPSC.1 (OCT4, Sox2, KLF4, c-Myc; Human fibroblasts)
3. FHC.1.H.iPSC.3 (OCT4, Sox2, KLF4, c-Myc; Human fibroblasts)
4. GSD.1.H.iPSC.7 (OCT4, Sox2, KLF4, c-Myc; Human fibroblasts)
5. TYR.1.H.iPSC.1 (OCT4, Sox2, KLF4, c-Myc; Human fibroblasts)
6. HER.1.H.iPSC.1 (OCT4, Sox2, KLF4, c-Myc; Human fibroblasts)
7. R.1.H.iPSC.4 (OCT4, Sox2, KLF4, c-Myc; Human fibroblasts)
8. R.1.H.iPSC.9 (OCT4, Sox2, KLF4, c-Myc; Human fibroblasts)
9. RP2.H.iPSC.3 (OCT4, Sox2, KLF4, c-Myc; iPS cells)
10. LCA.1.H.iPSC.1 (OCT4, Sox2, KLF4, c-Myc; iPS cells)
11. USH.1.H.iPSC.6 (OCT4, Sox2, KLF4, c-Myc; Human fibroblasts)
12. RP.1.H.iPSC.2 (OCT4, Sox2, KLF4, c-Myc; Human fibroblasts)
13. ARMD.1.H.iPSC.2 (OCT4, Sox2, KLF4, c-Myc; Human fibroblasts)
14. LHON.1.H.iPSC.5 (OCT4, Sox2, KLF4, c-Myc; iPS cells)
15. CNS.1.H.iPSC.10 (OCT4, Sox2, KLF4, c-Myc; iPS cells)
16. CNS.2.H.iPSC.7 (OCT4, Sox2, KLF4, c-Myc; iPS cells) |
| Centre of Regenerative Medicine in Barcelona (Spain) | 1. KiPS4F-1 (OCT4, Sox2, KLF4, c-Myc; human foreskin keratinocytes; 46XY)
2. KiPS3F-7 (OCT4, Sox2, KLF4); human foreskin keratinocytes)
3. KiPS4F-8 (OCT4, Sox2, KLF4, c-Myc human foreskin keratinocytes; 46XY)
4. cFA404-KiPS4F-1 (OCT4, Sox2, KLF4, c-Myc; Epidermal keratinocytes; 46XY) |

TABLE 3-continued

Listing of human induced pluripotent stem (hIPS) cell lines

|  |  |
|---|---|
| | 5. cFA404-KiPS4F-3 (OCT4, Sox2, KLF4, c-Myc; Epidermal keratinocytes; 46XY) |
| Universite Paris-Sud 11 (France) | 1. PB03 (Oct4, Sox2, Lin28, Nanog; Primary Amniocytes; 46XX; Lentivirus) |
| | 2. PB04 (Oct4, Sox2, Lin28, Nanog; Primary Amniocytes; B-Thalassemia affected; 46XY; Lentivirus) |
| | 3. PB05-1 (Oct4, Sox2, Lin28, Nanog; Primary Amniocytes; B-Thalassemia affected; 46XY; Lentivirus) |
| | 4. PB05 (Oct4, Sox2, Lin28, Nanog; Primary Amniocytes; B-Thalassemia affected; 46XY; Lentivirus) |
| | 5. PB06 (Oct4, Sox2, Lin28, Nanog; Primary Amniocytes; Down Syndrome; 47XY, +21; Lentivirus) |
| | 6. PB06-1 (Oct4, Sox2, Lin28, Nanog; Primary Amniocytes; Down Syndrome; 47XY, +21; Lentivirus) |
| | 7. PB07 (OCT4, Sox2, KLF4, c-Myc; Primary Amniocytes; 46XY; Retrotivirus) |
| | 8. PB08 (OCT4, Sox2, KLF4, c-Myc; Primary Amniocytes; 46XY; Retrotivirus) |
| | 9. PB09 (Oct4, Sox2, Lin28, Nanog; Primary Amniocytes; 46XY; Lentivirus) |
| | 10. PB10 (Oct4, Sox2; Primary Amniocytes46XY, Lentivirus) |
| Kyoto University (Japan) | 1. 201B1 (human fibroblast; 46XX) |
| | 2. 201B2 (human fibroblast; 46XX) |
| | 3. 201B3 (human fibroblast; 46XX) |
| | 4. 201B6 (human fibroblast; 46XX) |
| | 5. 201B7 (human fibroblast; 46XX) |
| | 6. 243H1 (human fibroblast) |
| | 7. 243H7 (human fibroblast) |
| | 8. 246B1 (Normal, 46XX) |
| | 9. 246B2 (Normal, 46XX) |
| | 10. 246B3 (Normal, 46XX) |
| | 11. 246B4 (Normal, 46XX) |
| | 12. 246B5 (Normal, 46XX) |
| | 13. 246B6 (Normal, 46XX) |
| | 14. 246G1 (human fibroblast; Takahashi, K., et al. 2007. Induction of pluripotent stem cells from adult human fibroblasts by defined factors Cell. 131: 861-72) |
| | 15. 246G3 (human fibroblast; Takahashi, K., et al. 2007. Induction of pluripotent stem cells from adult human fibroblasts by defined factors Cell. 131: 861-72) |
| | 16. 246G4 (human fibroblast; Takahashi, K., et al. 2007. Induction of pluripotent stem cells from adult human fibroblasts by defined factors Cell. 131: 861-72) |
| | 17. 246G5 (human fibroblast; Takahashi, K., et al. 2007. Induction of pluripotent stem cells from adult human fibroblasts by defined factors Cell. 131: 861-72) |
| | 18. 246G6 (human fibroblast; Takahashi, K., et al. 2007. Induction of pluripotent stem cells from adult human fibroblasts by defined factors Cell. 131: 861-72) |
| | 19. 253F1 (Normal, 46XX; Takahashi, K., et al. 2007. Induction of pluripotent stem cells from adult human fibroblasts by defined factors Cell. 131: 861-72) |
| | 20. 253F2 (Normal, 46XX; Takahashi, K., et al. 2007. Induction of pluripotent stem cells from adult human fibroblasts by defined factors Cell. 131: 861-72) |
| | 21. 253F3 (Normal, 46XX; Takahashi, K., et al. 2007. Induction of pluripotent stem cells from adult human fibroblasts by defined factors Cell. 131: 861-72) |
| | 22. 253F4 (Normal, 46XX; Takahashi, K., et al. 2007. Induction of pluripotent stem cells from adult human fibroblasts by defined factors Cell. 131: 861-72) |
| | 23. 253F5 (Normal, 46XX; Takahashi, K., et al. 2007. Induction of pluripotent stem cells from adult human fibroblasts by defined factors Cell. 131: 861-72) |
| Shanghai Institutes for Biological Sciences (China) | 1. HAFDC-IPS-6 (Li C., et al. 2009 Pluripotency can be rapidly and efficiently induced in human amniotic fluid-derived cells Hum Mol Genet. 2009 Nov 15; 18(22): 4340-9) |
| | 2. IPS-S (Liao, J., et al. 2008. Enhanced efficiency of generating induced pluripotent stem (iPS) cells from human somatic cells by a combination of six transcription factors Cell Res. 18: 600-3) |

Another advantage is that such MPS cells would be an immunologically matched autologous cell population; and patient-specific cells would allow for studying origin and progression of the disease. Thus, it is possible to understand the root causes of a disease, which can provide insights leading to development of prophylactic and therapeutic treatments for the disease.

Pluripotent Human Embryonic Stem (hES) Cells

The invention described herein is useful with all hES cell lines, and at least those listed in Table 4. This information was derived from the literature and publically available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained. As of the filing date of this application there were 254 iPSC lines listed with the International Stem Cell Registry and 1211 hESC lines. Table 4 below is not inclusive of all hESC and iPSC that are listed, but rather, are examples of the pluripotent stem cells potentially available.

TABLE 4

Listing of human embryonic stem (hES) cell lines

Institution (Country)

U.S.A.

| Institution | Cell Lines |
|---|---|
| BresaGen, Inc., Athens, Georgia (USA) | BG01, BG02, BG03; BG04; BG01v |
| Invitrogen (USA) | BG01v/hOG |
| CyThera, Inc., San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES25, HUES26, HUES27; HUES28; HUES48; HUES49; HUES53; HUES55 & HUES 56 |
| Mt Sinai Hospital-Samuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46, XY; RG-153; DYSTROPHIA MYOTONICA 1 (DM1), affected, 46, XX; RG-170; MUSCULAR DYSTROPHY, BECKER TYPE (BMD), affected, 46, XY; RG-186; HUNTINGTON DISEASE (HD), affected, 46, XX; RG-194; HUNTINGTON DISEASE (HD), affected, 46, XY; RG-233; HEMOGLOBIN B LOCUS (HBB), affected (HbS/HbS - sickle cell anemia), 46, XX; RG-245; EMERY-DREIFUSS MUSCULAR DYSTROPHY, X-LINKED (EDMD), carrier, 47, XXY; RG-246; EMERY-DREIFUSS MUSCULAR |

TABLE 4-continued

Listing of human embryonic stem (hES) cell lines

| Institution (Country) | |
|---|---|
| | DYSTROPHY, X-LINKED (EDMD), affected, 46, XY; |
| | RG-271; TORSION DYSTONIA 1 (DYT1), AUTOSOMAL DOMINANT, affected (N/GAG del), 46, XY; |
| | RG-283; MUSCULAR DYSTROPHY, DUCHENNE TYPE (DMD), affected, 46, XY; |
| | RG-288; CYSTIC FIBROSIS (CF), affected (deltaF508/deltaF508), 46, XY; |
| | RG-289; CYSTIC FIBROSIS (CF), affected (deltaF508/deltaF508), 46, XX; |
| | RG-301; MUSCULAR DYSTROPHY, DUCHENNE TYPE(DMD) affected, 46, XY; |
| | RG-302; MUSCULAR DYSTROPHY, DUCHENNE TYPE (DMD), carrier, 46, XX; |
| | RG-315; NEUROFIBROMATOSIS, TYPE I (NF1), affected (R19 47X/N), 46, XY; |
| | RG-316; TUBEROUS SCLEROSIS, TYPE 1(TSC1), affected (N/IVS7 + 1 G-A); |
| | RG-316; TUBEROUS SCLEROSIS, TYPE 1(TSC1), affected (N/IVS7 + 1 G-A); |
| | RG-320; TUBEROUS SCLEROSIS, TYPE 1(TSC1), affected (N/IVS7 + 1 G-A); |
| | RG-326; POPLITEAL PTERYGIUM SYNDROME (PPS), affected (R84H/N), 46, XY; |
| | RG-328; FACIOSCAPULOHUMERAL MUSCULAR DYSTROPHY 1A(FSHD), affected, 46, XY; |
| | RG-330; FACIOSCAPULOHUMERAL MUSCULAR DYSTROPHY 1A (FSHD), affected, 46, XY; |
| | RG-333; FACIOSCAPULOHUMERAL MUSCULAR DYSTROPHY 1A (FSHD), affected, 46, XX; |
| | RG-356; HEMOGLOBIN ALPHA LOCUS (HBA), affected (-alpha/--), 46, XX; |
| | RG-357; EMERY-DREIFUSS MUSCULAR DYSTROPHY, X-LINKED (EDMD), affected, 46, XY; |
| | RG-358; EMERY-DREIFUSS MUSCULAR DYSTROPHY, X-LINKED (EDMD), affected, 46, XY; |
| | RG-399; FACIOSCAPULOHUMERAL MUSCULAR DYSTROPHY 1A (FSHD), affected, 46, XX; |
| | RG-401; FACIOSCAPULOHUMERAL MUSCULAR DYSTROPHY 1A (FSHD), affected, 46, XX; |
| | RG-402; FACIOSCAPULOHUMERAL MUSCULAR DYSTROPHY 1A (FSHD), affected, 46, XX; |
| | RG-403; FACIOSCAPULOHUMERAL MUSCULAR DYSTROPHY 1A (FSHD), affected; |
| | RG-404; SPINAL MUSCULAR ATROPHY, TYPE I (SMA1), affected, 46, XY; |
| | RG-406; TORSION DYSTONIA 1, AUTOSOMAL DOMINANT (DYT1), affected (N/GAG del); |
| | RG-413; BREAST CANCER, FAMILIAL (BRCA2), affected (N/IVS7 GT del) & MULTIPLE ENDOCRINE NEOPLASIA, TYPE I (MEN1), affected (N/3036 4 bp del); |
| | RG-414; MULTIPLE ENDOCRINE NEOPLASIA, TYPE I (MEN1), affected (N/3036 4 bp del); |
| | RG-415; HUNTINGTON DISEASE (HD), affected; |
| | RG-416; CYSTIC FIBROSIS (CF), affected (deltaF508/1717-1 G-A); |
| | RG-417; CYSTIC FIBROSIS (CF), affected (deltaF508/1717-1 G-A); |
| | RG-418; HEMOGLOBIN B LOCUS (HBB), affected (cd8 + G/619del); |

TABLE 4-continued

Listing of human embryonic stem (hES) cell lines

| Institution (Country) | |
|---|---|
| | RG-420; HEMOGLOBIN B LOCUS (HBB), affected (cd8 + G/619del); RG-422; CYSTIC FIBROSIS (CF), affected (N1303K/deltaF508); RG-423; CYSTIC FIBROSIS (CF), carrier (N/deltaF508); RG-424; MULTIPLE ENDOCRINE NEOPLASIA, TYPE 2 (MEN2B), affected (M918T/N); RG-426; PELIZAEUS-MERZBACHER DISEASE (PMLD), affected; RG-428; TUBEROUS SCLEROSIS, TYPE 1 (TSC1), affected (N/IVS7 + 1 G-A); |
| South American | |
| Institute de Biociencias, São Paulo (Brazil) | BR-1 |
| Middle East | |
| Technion-Israel Institute of Technology, Haifa (Israel) | TE03, TE04, TE06 (I 3, I 4, I 6) |
| Hadassah University Hospital (Israel) | HAD 1; HAD 2; HAD 3; HAD 4; HAD 5; HAD 6 |
| Hebrew University of Jerusalem | HEFX1 |
| Technion - Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |
| Europe | |
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-l; Edi-2; Edi-3; Edi-4 |
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/ Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (ASCC) | MEL-1; MEL-2; MEL-3; MEL-4 |

TABLE 4-continued

Listing of human embryonic stem (hES) cell lines

| Institution (Country) | |
|---|---|
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centro de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |
| Vrije Universiteit Brussel (Belgium) | VUB01; VUB02; VUB06; VUB07; VUB03_DM1; VUB04_CF; VUB05_HD; VUB08_MFS; VUB09_FSHD; VUB10_SCA7; VUB11_FXS; VUB13_FXS; VUB14; VUB19_DM1; VUB20_CMT1A; VUB22_CF; VUB23_OI; VUB24_DM1; VUB26; VUB27; VUB28_HD_MFS |
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |
| Australia | |
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |
| Asia | |
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |
| ES Cell International Pte Ld (Singapore) | ES01, ES02, ES03, ES04, ES05, ES06 (HES-1, HES-2, HES-3, HES-4, HES-5, HES-6 |
| Maria Biotech Co. Ltd. - Maria Infertility Hospital Medical Institute, Seoul (Korea) | MB01; MB02; MB03; MB04; MB05; MB06; MB07; MB08; MB09 |
| MizMedi Hospital-Seoul National University, Seoul (Korea) | MI01 (Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhES1; SNUhES2; SNUhES3; SNUhES4; SNUhES11; SNUhES16 |

TABLE 4-continued

Listing of human embryonic stem (hES) cell lines

| Institution (Country) | |
|---|---|
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10, |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1 + H9 |
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10;; FY-hES-11 |

Aggregate Suspension of Pluripotent Stem Cells

In contrast to previously known methods of tissue engineering which are based on seeding individual cells into polymer scaffolds, matrices and/or gels, embodiments described herein can use cell aggregate suspensions formed from pluripotent stem cell, single cell suspensions or differentiated single cell suspensions derived therefrom.

Embodiments described herein relate to methods for generating a pluripotent cell aggregate in suspension from a pluripotent adherent culture, by culturing a pluripotent cell in an adherent growth culture condition which allows for expansion in an undifferentiated state; disassociating the adherent pluripotent cell culture into a single cell suspension culture; contacting the single cell suspension culture with a first differentiating culture condition which allows for formation of hES-derived cell aggregates in suspension by agitating the single cell suspension culture until such a period of time when the single cell suspension culture forms a pluripotent-derived cell aggregate in suspension, and thereby generating a pluripotent-derived cell aggregate in suspension. In preferred embodiments, agitation of the single cell suspension culture is performed by rotation at about 80 rpm to 160 rpm. In certain other embodiments described herein, a rho-kinase inhibitor is used to facilitate pluripotent stem cell aggregation, growth, proliferation, expansion and/or cell mass.

Methods of processing and/or manufacturing of stem cell aggregate suspension and differentiation of cells thereof is described in in at least Applicants U.S. Pat. Nos. 8,153,429; 8,211,699; 8,145,158; and 8,658,352.

Although the exact number of cells per aggregate is not critical, it will be recognized by those skilled in the art that the size of each aggregate (and thus the number of cells per aggregate) is limited by the capacity of oxygen and nutrients to diffuse to the central cells, and that this number may also vary depending on cell type and the nutritive requirements of that cell type. Cell aggregates may comprise a minimal number of cells (e.g., two or three cells) per aggregate, or may comprise many hundreds or thousands of cells per aggregate. Typically, cell aggregates comprise hundreds to thousands of cells per aggregate. For purposes of the present invention, the cell aggregates are typically from about 50 microns to about 600 microns in size, although, depending on cell type, the size may be less or greater than this range. In one embodiment, the cell aggregates are from about 50 microns to about 250 microns in size, or about 75 to 200 microns in size, and preferably they are about 100 to 150 microns in size.

Still other methods describe making embryoid bodies (EBs). As used herein, the term "embryoid bodies", "aggregate bodies" or equivalents thereof, refer to aggregates of differentiated and undifferentiated cells that appear when ES cells overgrow in monolayer cultures, or are maintained in suspension cultures in undefined media or are differentiated via non-directed protocols towards multiple germ layer tissues. That is, EBs are not formed from a single cell suspension of pluripotent stem cells as described herein; nor are EBs formed from adherent cultures of pluripotent-derived multipotent cells. These features alone make the present invention clearly distinguished from an embryoid body.

In contrast to embryoid bodies, which are a mixture of differentiated and undifferentiated cells and typically consist of cells from several germ layers and go through random differentiation, the cell aggregates described herein are essentially or substantially homo-cellular, existing as aggregates of pluripotent, multipotent, bipotent, or unipotent type cells, e.g., embryonic cells, definitive endoderm, foregut endoderm, PDX1 positive pancreatic endoderm, pancreatic endocrine cells and the like.

Embodiments described herein address the above problems by providing a cost efficient manufacturing process or methods capable of reproducibly producing cell aggregates that are substantially uniform in size and shape using a process that can easily be applied to large-scale manufacturing. In one particular embodiment, the differentiable cells are expanded in a suspension culture, using the cell media of the present invention. In another particular embodiment, the differentiable cells can be maintained and expanded in suspension, i.e., they remain undifferentiated or are prevented from further differentiating. The term "expand" in the context of cell culture is used as it is in the art, and refers to cellular proliferation and increase the number of cells, preferably increase in number of viable cells. In a specific embodiment, the cells are expanded in a culture suspension by culturing for more than about one day, i.e., about 24 hours. In a more specific embodiment, the cells are expanded in a suspension culture by culturing for at least 1, 2, 3, 4, 5, 6, 7 days, or at least 2, 3, 4, 5, 6, 7, 8 weeks.

Still other embodiments of the invention provide for methods of producing cell aggregate suspensions formed from differentiated pluripotent stem cell cultures e.g., cells produced from the pluripotent cells described herein, and including cells from stages 1, 2, 3, 4 and 5 as described in d'Amour 2005 and 2006, supra. Hence, methods for making the cell aggregates described herein are not limited to any one pluripotent or multipotent cell or cell stage, rather the manner of use and need for cell type optimization will dictate which methods are preferred.

The methods described herein for producing aggregate suspension cultures of pluripotent cells, e.g., hES or iPS cells, and cells derived from other pluripotent cell sources, for example, embryonic germ or parthenote cells, are substantially as described in PCT/US2007/062755, filed Feb. 23, 2007, and titled Compositions and methods for culturing differential cells and PCT/US2008/080516, filed Oct. 20, 2008, and titled Methods and compositions for feeder-free pluripotent stem cell media containing human serum, which are herein incorporated by reference in their entireties.

The methods described herein in no way require first coating the culturing vessels with an extracellular matrix, e.g., as described in U.S. Pat. No. 6,800,480 to Bodnar et al. and assigned to Geron Corporation. In some embodiments described herein, iPS cells can be cultured in the same way that other pluripotent stem cells, e.g., hES and iPS cells, are cultured using soluble human serum as substantially described in U.S. Application, PCT/US2008/080516, filed Oct. 20, 2008, and titled Methods and compositions for feeder-free pluripotent stem cell media containing human serum, which is herein incorporated by reference in its entirety.

The methods described herein in no way require exogenously added fibroblast growth factor (FGF) supplied from a source other than just a fibroblast feeder layer as described in U.S. Pat. No. 7,005,252 to Thomson, J. and assigned to the Wisconsin Alumni Research Foundation (WARF), which is herein incorporated by reference in its entirety.

Multipotent and Differentiated Cell Compositions

Cell compositions produced by the methods described herein include cell cultures comprising pluripotent stem cells, preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells, wherein at least about 5-90% of the cells in culture are the preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells produced.

Some embodiments described herein relate to compositions, such as cell populations and cell cultures that comprise both pluripotent cells, such as stem cells and iPS cells, and multipotent cells, such as preprimitive streak, mesendoderm or definitive endoderm, as well as more differentiated, but still potentially multipotent, cells, such as PDX1-positive foregut endoderm, PDX1-positive pancreatic endoderm or PDX1/NKX6.1 co-positive pancreatic endoderm, endocrine precursor or NGN3/NKX2.2 co-positive endocrine precursor, and hormone secreting endocrine cells or INS, GCG, GHRL, SST, PP singly-positive endocrine cells. For example, using the methods described herein, compositions comprising mixtures of pluripotent stem cells and other multipotent or differentiated cells can be produced. In some embodiments, compositions comprising at least about 5 multipotent or differentiated cells for about every 95 pluripotent cells are produced. In other embodiments, compositions comprising at least about 95 multipotent or differentiated cells for about every 5 pluripotent cells are produced. Additionally, compositions comprising other ratios of multipotent or differentiated cells to pluripotent cells are contemplated. For example, compositions comprising at least about 1 multipotent or differentiated cell for about every 1,000,000 pluripotent cells, at least about 1 multipotent or differentiated cell for about every 100,000 pluripotent cells, at least about 1 multipotent or differentiated cell for about every 10,000 pluripotent cells, at least about 1 multipotent or differentiated cell for about every 1000 pluripotent cells, at least about 1 multipotent or differentiated cell for about every 500 pluripotent cells, at least about 1 multipotent or differentiated cell for about every 100 pluripotent cells, at least about 1 multipotent or differentiated cell for about every 10 pluripotent cells, at least about 1 multipotent or differentiated cell for about every 5 pluripotent cells, and up to about every 1 pluripotent cell and at least about 1,000,000 multipotent or differentiated cell for about every 1 pluripotent cell are contemplated.

Some embodiments described herein relate to cell cultures or cell populations comprising from at least about 5% multipotent or differentiated cell to at least about 99% multipotent or differentiated cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are multipotent or differentiated cell. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are multipotent or differentiated cells. In embodiments where the cell cultures or cell populations comprise human feeder cells, the above percentages are calculated without respect to the human feeder cells in the cell cultures.

Monitoring the Production of Multipotent or Differentiated Cells

The progression of pluripotent cells to multipotent cells to further multipotent cells or differentiated cells, such as pancreatic progenitors or hormone endocrine secreting cells, can be monitored by determining the expression of markers characteristic of the specific cells, including genetic markers and phenotypic markers such as, the expression of islet hormones and the processing of proinsulin into insulin and C peptide in endocrine cells. In some processes, the expression of certain markers is determined by detecting the presence or absence of the marker. Alternatively, the expression of certain markers can be determined by measuring the level at which the marker is present in the cells of the cell culture or cell population. For example, in certain processes, the expression of markers characteristic of immature pancreatic islet hormone-expressing cells as well as the lack of significant expression of markers characteristic of pluripotent cells, definitive endoderm, foregut endoderm, PDX1-positive foregut endoderm, endocrine precursor, extraembryonic endoderm, mesoderm, ectoderm, mature pancreatic islet hormone-expressing cells and/or other cell types is determined.

As described in connection with monitoring the production of other less differentiated cell types of the definitive endoderm lineage, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

For example, in one embodiment, PDX1 is a marker gene that is associated with PDX1-positive foregut endoderm. As such, in some embodiments of the present invention, the expression of PDX1 is determined. In other embodiments, the expression of other markers, which are expressed in PDX1-positive foregut endoderm, including, but not limited to, SOX17, HNF6, SOX9 and PROX1 is also determined. Since PDX1 can also be expressed by certain other cell types (that is, visceral endoderm and certain neural ectoderm), some embodiments of the present invention relate to demonstrating the absence or substantial absence of marker gene expression that is associated with visceral endoderm and/or neural ectoderm. For example, in some embodiments, the expression of markers, which are expressed in visceral endoderm and/or neural cells, including, but not limited to, SOX7, AFP, SOX1, ZIC1 and/or NFM is determined.

In some embodiments, PDX1-positive foregut endoderm cell cultures produced by the methods described herein are substantially free of cells expressing the SOX7, AFP, SOX1, ZIC1 or NFM marker genes. In certain embodiments, the PDX1-positive foregut endoderm cell cultures produced by the processes described herein are substantially free of visceral endoderm, parietal endoderm and/or neural cells.

The developmental progression of the pluripotent cells described herein (e.g., cells produced as a result of Stages or Steps 1-5 as described in D'Amour et al. 2006, supra) can be monitored by determining the expression of markers characteristic of each hES-derived or iPS-derived cell type along the developmental pathway. In some processes, the identification and characterization of a hES-derived or iPS-derived cell type is by expression of a certain marker or different expression levels and patterns of more than one marker. That is, the presence or absence, the high or low expression, of one or more the marker(s) typifies and identifies a cell-type. Also, certain markers can have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantitating the expression of markers that are produced by marker genes is through the use of quantitative PCR (Q-PCR). Methods of performing Q-PCR are well known in the art.

In some embodiments of the present invention, the presence, absence and/or level of expression of a marker is determined by quantitative PCR (Q-PCR). For example, the amount of transcript produced by certain genetic markers, such as SOX17, CXCR4, OCT4, AFP, TM, SPARC, SOX7, CDX2, MIXL1, GATA4, HNF3f3, HNF4alpha, GSC, FGF17, VWF, CALOR, FOXQ1, CMKOR1, CRIP1 and other markers described herein is determined by quantitative Q-PCR.

In other embodiments, immunohistochemistry is used to detect the proteins expressed by the above-mentioned genes. In still other embodiments, Q-PCR can be used in conjunction with immunohistochemical techniques or flow cytometry techniques to effectively and accurately characterize and identify cell types and determine both the amount and relative proportions of such markers in a subject cell type. In one embodiment, Q-PCR can quantify levels of RNA expression in a cell culture containing a mixed population of cells. However, Q-PCR cannot provide or qualify whether the subject markers or proteins are co-expressed on the same cell. In another embodiment, Q-PCR is used in conjunction with flow cytometry methods to characterize and identify cell types. Thus, by using a combination of the methods described herein, and such as those described above, complete characterization and identification of various cell types, including endoderm lineage type cells, can be accomplished and demonstrated.

For example, in one preferred embodiment, pancreatic progenitors or pancreatic endoderm or PDX-1 positive pancreatic endoderm, expresses at least PDX1, Nkx6.1, PTF1A, CPA and/or cMYC as demonstrated by Q-PCR and/or ICC, but such a cell at least co-expresses PDX1 and Nkx6.1 as demonstrated by ICC and does not express other markers including SOX17 CXCR4, or CER, to be identified as a PDX1-positive expressing cell. Similarly, for proper identification of a mature hormone secreting pancreatic cell, in vitro or in vivo, for example, there is demonstrated that C-peptide (a product of proper processing of pro-insulin in a mature and functioning β cell) and insulin are co-expressed by ICC in the insulin secreting cell.

Still, other methods which are known in the art can also be used to quantitate marker gene expression. For example, the expression of a marker gene product can be detected by using antibodies specific for the marker gene product of interest (e.g., e.g. Western blot, flow cytometry analysis, and the like). In certain processes, the expression of marker genes characteristic of hES-derived cells as well as the lack of significant expression of marker genes characteristic of hES-derived cells. Still further methods for characterizing and identifying hES-derived cells types are described in related applications as indicated above, which are herein incorporated by reference in their entirety.

Amplification probe/primer combinations suitable for use in amplification assays include the following: Insulin (INS) (GenBank NM_000207): primers AAGAGGCCAT-CAAGCAGATCA (SEQ ID NO: 1); CAGGAGGCGCATC-CACA (SEQ ID NO: 2); Nkx6.1 (NM_006168): primers CTGGCCTGTACCCCTCATCA (SEQ ID NO: 3); CTTC-CCGTCTTTGTCCAACAA (SEQ ID NO: 4); Pdx1 (NM_000209): primers AAGTCTACCAAAGCTCACGCG (SEQ ID NO: 5); GTAGGCGCCGCCTGC (SEQ ID NO: 6); Ngn3 (NM_020999): primers GCTCATCGCTCTCTAT-TCTTTTGC (SEQ ID NO: 7); GGTTGAGGCGTCATC- CTTTCT (SEQ ID NO: 8); FOXA2 (HNF3B) (NM_021784): primers GGGAGCGGTGAAGATGGA (SEQ ID NO: 9); TCATGTTGCTCACGGAGGAGTA (SEQ ID NO: 10); Glucagon (GCG) (NM_002054): primers AAGCATTTACTTTGTGGCTGGATT (SEQ ID NO: 11); TGATCTGGATTTCTCCTCTGTGTCT (SEQ ID NO: 12); HNF6 (NM_030712): primers CGCTCCGCTTAGCAG-CAT (SEQ ID NO: 13); GTGTTGCCTCTATCCTTCCCAT (SEQ ID NO: 14); HNF4Alpha (NM_000457): primers GAAGAAGGAAGCCGTCCAGA (SEQ ID NO: 15); GACCTTCGAGTGCTGATCCG (SEQ ID NO: 16); Sox17 (NM_022454): primers GGCGCAGCAGAATCCAGA (SEQ ID NO: 17); NNNNNNNNNNNNNNN NNNNN (SEQ ID NO: 18); HLxB9 (NM_005515): primers CAC-CGCGGGCATGATC (SEQ ID NO: 19); ACTTCCCCAG-GAGGTTCGA (SEQ ID NO: 20); Nkx2.2 (NM_002509): primers GGCCTTCAGTACTCCCTGCA (SEQ ID NO: 21); GGGACTTGGAGCTTGAGTCCT (SEQ ID NO: 22); PTF1a (NM_178161): primers GAAGGTCATCATCTGC-CATCG (SEQ ID NO: 23) GGCCATAATCAGGGTCGCT (SEQ ID NO: 24); SST (NM_001048): primers CCCCA-GACTCCGTCAGTTTC (SEQ ID NO: 25); TCCGTCTG-GTTGGGTTCAG (SEQ ID NO: 26); PAX6 (NM_000280): primers CCAGAAAGGATGCCTCATAAAGG (SEQ ID NO: 27); TCTGCGCGCCCCTAGTTA (SEQ ID NO: 28); Oct4 primers: TGGGCTCGAGAAGGATGTG (SEQ ID NO: 29) GCATAGTCGCTGCTTGATCG (SEQ ID NO: 30); MIXL1 primers CCGAGTCCAGGATCCAGGTA (SEQ ID NO: 31) CTCTGACGCCGAGACTTGG (SEQ ID NO: 32); GATA4 primers CCTCTTGCAATGCGGAAAG (SEQ ID NO: 33) CGGGAGGAAGGCTCTCACT (SEQ ID NO: 34); GSC primers GAGGAGAAAGTGGAGGTCTG-GTT (SEQ ID NO: 35) CTCTGATGAGGACCGCTTCTG (SEQ ID NO: 36); CER primers ACAGTGCCCTTCAGC-CAGACT (SEQ ID NO: 37) ACAACTACTTTTTCACA-GCCTTCGT (SEQ ID NO: 38); AFP primers GAGAAAC-CCACTGGAGATGAACA (SEQ ID NO: 39) CTCATGGCAAAGTTCTTCCAGAA (SEQ ID NO: 40); SOX1 primers ATGCACCGCTACGACATGG (SEQ ID NO: 41) CTCATGTAGCCCTGCGAGTTG (SEQ ID NO: 42); ZIC1 primers CTGGCTGTGGCAAGGTCTTC (SEQ ID NO: 43) CAGCCCTCAAACTCGCACTT (SEQ ID NO: 44); NFM primers ATCGAGGAGCGCCACAAC (SEQ ID NO: 45) TGCTGGATGGTGTCCTGGT (SEQ ID NO: 46). Other primers are available through ABI Taqman including FGF17 (Hs00182599_m1), VWF (Hs00169795_m1), CMKOR1 (Hs00604567_m1), CRIP1 (Hs00832816_g1), FOXQ1 (Hs00536425_s1), CALCR (Hs00156229_m1) and CHGA (Hs00154441_m1).

Summary of the Production of PDX1-Positive Pancreatic Endoderm (Stages 1 to 4) and Insulin Production In Vivo The methods for production of certain endoderm-lineage and pancreatic endoderm-lineage cells are provided herein, and discussed elsewhere in related applications such as U.S. application Ser. No. 11/773,944, entitled METHODS OF PRODUCING PANCREATIC HORMONES, filed Jul. 5, 2007, which is a continuation-in-part of U.S. patent application Ser. No. 11/681,687, entitled ENDOCRINE PRE-CURSOR CELLS, PANCREATIC HORMONE-EXPRESS-ING CELLS AND METHODS OF PRODUCTION, filed Mar. 2, 2007.

Briefly, the directed differentiation methods herein for pluripotent stem cells, for example, hES and iPS cells, can be described into at least four or five stages. Stage 1 is the production of definitive endoderm from pluripotent stem cells and takes about 2 to 5 days, preferably 2 or 3 days. Pluripotent stem cells are suspended in media comprising RPMI, a TGFβ superfamily member growth factor, such as Activin A, Activin B, GDF-8 or GDF-11 (100 ng/mL), a Wnt family member or Wnt pathway activator, such as Wnt3a (25 ng/mL), and alternatively a rho-kinase or ROCK inhibitor, such as Y-27632 (10 µM) to enhance growth, survival and proliferation as well as promoting cell-cell adhesion. After about 24 hours, the media is exchanged for media comprising RPMI with serum, such as 0.2% FBS, and a TGFβ superfamily member growth factor, such as Activin A, Activin B, GDF-8 or GDF-11 (100 ng/mL), and alternatively a rho-kinase or ROCK inhibitor for another 24 (day 1) to 48 hours (day 2). Alternatively, after about 24 hours in a medium comprising Activin/Wnt3a, the cells are cultured during the subsequent 24 hours in a medium comprising Activin alone (i.e., the medium does not include Wnt3a). Importantly, production of definitive endoderm requires cell culture conditions low in serum content and thereby low in insulin or insulin-like growth factor content. See McLean et al. (2007) Stem Cells 25: 29-38, which is herein incorporated in its entirety. McLean et al. also show that contacting hES cells with insulin in concentrations as little as 0.2 µg/mL at Stage 1 can be detrimental to the production of definitive endoderm. Still others skilled in the art have modified the Stage 1 differentiation of pluripotent cells to definitive endoderm substantially as described here and in D'Amour et al. (2005), for example, at least, Agarwal et al., Efficient Differentiation of Functional Hepatocytes from Human Embryonic Stem Cells, Stem Cells (2008) 26:1117-1127; Borowiak et al., Small Molecules Efficiently Direct Endo-dermal Differentiation of Mouse and Human Embryonic Stem Cells, (2009) Cell Stem Cell 4:348-358; and Brunner et al., Distinct DNA methylation patterns characterize differentiated human embryonic stem cells and developing human fetal liver, (2009) Genome Res. 19:1044-1056. Proper differentiation, specification, characterization and identification of definitive are necessary in order to derive other endoderm-lineage cells. Definitive endoderm cells at this stage co-express SOX17 and HNF3β (FOXA2) and do not appreciably express at least HNF4alpha, HNF6, PDX1, SOX6, PROX1, PTF1A, CPA, cMYC, NKX6.1, NGN3, PAX3, ARX, NKX2.2, INS, GSC, GHRL, SST, or PP.

Stage 2 takes the definitive endoderm cell culture from Stage 1 and produces foregut endoderm or PDX1-negative foregut endoderm by incubating the suspension cultures with RPMI with low serum levels, such as 0.2% FBS, in a 1:1000 dilution of ITS, 25 ng KGF (or FGF7), and alternatively a ROCK inhibitor for 24 hours (day 2 to day 3) to enhance growth, survival, proliferation and promote cell-cell adhesion. After 24 hours (day 3 to day 4), the media is exchanged for the same media minus a TGFβ inhibitor, but alternatively still a ROCK inhibitor to enhance growth, survival and proliferation of the cells, for another 24 (day 4 to day 5) to 48 hours (day 6). A critical step for proper specification of foregut endoderm is removal of TGFβ family growth factors. Hence, a TGFβ inhibitor can be added to Stage 2 cell cultures, such as 2.504 TGFβ inhibitor no. 4 or 5 µM SB431542, a specific inhibitor of activin receptor-like kinase (ALK), which is a TGFβ type I receptor. Foregut endoderm or PDX1-negative foregut endoderm cells produced from Stage 2 co-express SOX17, HNF1β and HNF4alpha and do not appreciably co-express at least SOX17 and HNF3β (FOXA2), nor HNF6, PDX1, SOX6, PROX1, PTF1A, CPA, cMYC, NKX6.1, NGN3, PAX3, ARX, NKX2.2, INS, GSC, GHRL, SST, or PP, which are hallmark of definitive endoderm, PDX1-positive pancreatic endoderm or pancreatic progenitor cells or endocrine pre-cursors as well as singly or poly hormonal type cells.

Stage 3 (days 5-8) takes the foregut endoderm cell culture from Stage 2 and produces a PDX1-positive foregut endoderm cell by DMEM or RPMI in 1% B27, 0.2504 KAAD cyclopamine, a retinoid, such as 0.2 µM retinoic acid (RA) or a retinoic acid analog such as 3 nM of TTNPB, and 50 ng/mL of Noggin for about 24 (day 7) to 48 hours (day 8). Specifically, Applicants have used DMEM-high glucose since about 2003 and all patent and non-patent disclosures as of that time employed DMEM-high glucose, even if not mentioned as "DMEM-high glucose" and the like. This is, in part, because manufacturers such as Gibco did not name their DMEM as such, e.g. DMEM (Cat. No 11960) and Knockout DMEM (Cat. No 10829). It is noteworthy, that as of the filing date of this application, Gibco offers more DMEM products but still does not put "high glucose" in certain of their DMEM products that contain high glucose e.g. Knockout DMEM (Cat. No. 10829-018). Thus, it can be assumed that in each instance DMEM is described, it is meant DMEM with high glucose and this was apparent by others doing research and development in this field. Again, a ROCK inhibitor or rho-kinase inhibitor such as Y-27632 can be used to enhance growth, survival, proliferation and promote cell-cell adhesion. PDX1-positive foregut cells produced from Stage 3 co-express PDX1 and HNF6 as well as SOX9 and PROX, and do not appreciably co-express markers indicative of definitive endoderm or foregut endoderm (PDX1-negative foregut endoderm) cells or PDX1-positive foregut endoderm cells as described above in Stages 1 and 2.

Stage 4 (days 8-14) takes the media from Stage 3 and exchanges it for media containing DMEM in 1% vol/vol B27 supplement, plus 50 ng/mL KGF and 50 ng/mL of EGF and sometimes also 50 ng/mL Noggin. Again, a ROCK inhibitor such as Y-27632 can be used to enhance growth, survival, proliferation and promote cell-cell adhesion. PDX1-positive pancreatic endoderm cells produced from Stage 4 co-express at least PDX1 and Nkx6.1 as well as PTF1A, and do not appreciably express markers indicative of definitive endoderm or foregut endoderm (PDX1-negative foregut endoderm) cells as described above in Stages 1, 2 and 3.

Alternatively, the cells from Stage 4 can be further differentiated in Stage 5 to produce endocrine precursor or progenitor type cells and/or singly and poly-hormonal pancreatic endocrine type cells from Stage 4 cells in a medium containing DMEM in 1% vol/vol B27 supplement for about 1 to 6 days (days 15-20). Endocrine precursors produced from Stage 5 co-express at least NGN3 and PAX4 as well as Nkx2.2, and do not appreciably express markers indicative of definitive endoderm or foregut endoderm (PDX1-negative foregut endoderm) or PDX1-positive pancreatic endoderm or progenitor cells as described above in Stages 1, 2, 3 and 4.

PDX1-positive pancreatic endoderm produced from Stage 4 are loaded and wholly contained in a macro-encapsulation device and transplanted in a patient, and the PDX1-positive pancreatic endoderm cells mature into pancreatic hormone secreting cells, e.g., insulin secreting cells, in vivo. Encapsulation of the PDX1-positive pancreatic endoderm cells and production of insulin in vivo is described in detail in U.S. application Ser. No. 12/618,659 (the '659 application"), entitled ENCAPSULATION OF PANCREATIC LINEAGE CELLS DERIVED FROM HUMAN PLURIPOTENT STEM CELLS, filed Nov. 13, 2009. The '659 application claims the benefit of priority to Provisional Patent Application No. 61/114,857, entitled ENCAPSULATION OF PANCREATIC PROGENITORS DERIVED FROM HES CELLS, filed Nov. 14, 2008; and U.S. Provisional Patent Application No. 61/121,084, entitled ENCAPSULATION OF PANCREATIC ENDODERM CELLS, filed Dec. 9, 2008.

In still another embodiment, methods for producing further differentiated pancreatic-lineage cells, preferably, endocrine precursors of stage 5, 6 and immature beta cells of stage 7 are described herein in Table 5 and described in more detail in Applicants U.S. application No., ENCAPSULATION OF PANCREATIC CELLS DERIVED FROM HUMAN PLURIPOTENT STEM CELLS, filed Dec. 13, 2013. To make endocrine precursor and immature beta cells as described herein, stages 1-2 cells are substantially made as described in Applicant's standard stage 1-4 protocol (Protocol No. 1 of Table 5), but during stage 3 and 4, a combination of activin, heregulin and wnt (A, H, W) are added which suppresses NGN3 (endocrine) expression while at the same time maintaining good cell growth and differentiation. Proper suppression of NGN3 during stages 3 and 4, permits for its proper induction later in stage 5 with a gamma-secretase inhibitor (RO1), and then further differentiation during stages 6 and 7 to immature beta cells using at least nicotinamide (NC10), matrigel (MG0.05), Rho-kinase inhibitor and retinoic acid (Y10). See Protocol No. 3 in Table 5.

Method of Producing Insulin In Vivo

In some embodiments, in vitro-derived pancreatic progenitor cells or PDX-1-positive pancreatic endoderm type cells or equivalents thereof described-above are transplanted into a mammalian subject. These methods are described in detail in Applicants U.S. Pat. Nos. 7,534,608; 7,695,965; and 7,993,920, titled METHODS OF PRODUCING PANCREATIC HORMONES. In a preferred embodiment, the mammalian subject is a human subject. Particularly preferred subjects are those that have been identified as having a condition which limits the ability of the subject to produce sufficient levels of insulin in response to physiologically high blood glucose concentrations. A range of blood glucose levels that constitutes a physiologically high blood glucose level for any particular mammalian species can be readily determined by those of ordinary skill in the art. Any persistent blood glucose level that results in a recognized disease or condition is considered to be a physiologically high blood glucose level.

Additional embodiments of the present invention relate to an in vivo insulin secreting cell that is derived from an in vitro pluripotent stem cell or progeny thereof, e.g., multipotent cells, such as PDX-1 positive foregut endoderm cell, a PDX-1 positive pancreatic endoderm or pancreatic progenitor cell, an endocrine precursor, such as an NGN3 positive endocrine precursor, or a functional differentiated hormone secreting cell, such as an insulin, glucagon, somatistatin, ghrelin, or pancreatic polypeptide secreting cell. Any of the above-described terminally differentiated or multipotent cells can be transplanted into the host, or mammal, and mature into physiologically functional hormone secreting cells, such as insulin secreting cells, in response to host blood glucose levels. In preferred embodiments the cell does not form a teratoma in vivo, and if so formed, remains localized to the area of transplant and can be easily excised or removed. In especially preferred embodiments, the cell does not contain any karyotypic abnormality during the in vitro differentiation process, or when transplanted into the mammal in vivo, or when maturing and developing into functional islets in vivo.

Further, although embodiments described herein relate to an engineered or genetically recombinant pluripotent cell, multipotent or differentiated cell derived from the pluripotent cell, such as a human iPS cell, based on the description provided herein, it is anticipated that because iPS cells demonstrate similar physiology and gene marker expression profiles to that of hES cells and hES-derived cells, they will have similar physiological characteristics in vivo.

Method of Encapsulating Pancreatic Progenitors

In some embodiments, the pluripotent, multipotent and differentiated cell composition described herein can be encapsulated in a biological and/or non-biological mechanical device, where the encapsulated device separates and/or isolates the cell compositions from the host.

Methods of encapsulation are described in detail in U.S. Pat. No. 8,278,106, titled ENCAPSULATION OF PANCREATIC CELLS DERIVED FROM HUMAN PLURIPOTENT STEM CELLS; U.S. Application No. 61/121,086 filed Dec. 12, 2008, titled ENCAPSULATION OF PANCREATIC ENDODERM CELLS, which describes encapsulation of pancreatic endoderm cells using a semi-permeable membrane, e.g., a Theracyte™ or Gore device; Applicant's U.S. Design applications 29/408,366, 29/408,368, 29/408,370, 29/423,365, and 29/447,944, which describe other device embodiments.

In one embodiment, the encapsulation device contains the pluripotent derived cells, for example, PDX-1 positive foregut endoderm cell, a PDX-1 positive pancreatic endoderm or progenitor cell, an endocrine precursor, such as an NGN3 positive endocrine precursor, or a functional differentiated hormone secreting cell, such as an insulin, glucagon, somatistatin, ghrelin, or pancreatic polypeptide secreting cell, in a semipermeable membrane that prevents passage of the transplanted cell population, retaining them in the device, while at the same time permitting passage of certain secreted polypeptides, e.g., insulin, glucagon, somatistatin, ghrelin, pancreatic polypeptide and the like. Alternatively, the device has a plurality of membranes, including a vascularizing membrane.

In one embodiment, the implantable, semipermeable device is a TheraCyte device (Irvine, Calif.). TheraCyte cell encapsulation devices are further described in U.S. Pat. Nos. 6,773,458; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are all herein incorporated in their entireties by reference in their entireties.

Storing Cells for Encapsulation and Transplantation

Some embodiments relate to methods for cryopreserving cells which have been cultured and/or differentiated in vitro. Such storage would allow banking, quality control, and other desired procedures and manipulations, either in connection with in vitro analysis or implantation in vivo. Methods for cell storage prior to transplantation include preserving the tissue by freezing cells (cryopreservation); or by refrigerating the cells at above freezing temperatures (hibernation) or by storing cells at room temperature (storage). See Chanaud et al. 1987 Neurosci Lett 82: 127-133; Collier et al. (1987) 436: 363-366; and Sauer et al. 1991 Neurology and Neuroscience 2: 123-135; Gage et al. 1985 Neurosci Lett 60: 133-137, the disclosures of which are herein incorporated by reference in their entireties. Although hibernation has been reported to increase rates of graft survival and function as compared to cryopreserved tissue, cells may not be capable of long term maintenance under such conditions without jeopardizing cell viability during the hibernation period.

As used herein, a "cell suspension" or equivalents thereof refers to cell aggregates and/or clusters and/or spheres that are contacted with a medium. Such cell suspensions are described in detail in U.S. application Ser. No. 12/264,760, entitled Stem cell Aggregate Suspension Compositions and Methods of Differentiation Thereof, filed on Nov. 8, 2008, the disclosure of which is herein incorporated by reference in its entirety.

As used herein, "adapted cell suspension" or cell suspension cultures or equivalents thereof includes a cell suspension that has been stored above freezing, preferably at 4° C., in hibernation medium for about 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days.

As used herein, a cell suitable for transplantation refers to a cell or a population of cells sufficiently viable and/or functional for in vivo treatment of a metabolic disorder. For example, diabetes, or one or more symptoms thereof, can be ameliorated or reduced for a period of time following implantation of a cell suitable for transplantation into a subject suffering from diabetes. In one preferred embodiment, a cell or cell population suitable for transplantation is a pancreatic progenitor cell or population, or a PDX1-positive pancreatic progenitor cell or population, or an endocrine precursor cell or population, or a poly or singly-hormonal endocrine cell and/or any combination of cell or populations of cells, or even purified or enriched cells or populations of cells thereof. Cells suitable for the embodiments described herein are further described in detail in U.S. Pat. No. 7,534,608 the disclosure of which is herein incorporated by reference in its entirety.

As used herein the term "storing" or equivalents thereof refers to holding or maintaining cells either above or below freezing. The term is also meant to include maintaining cells prior to use in transplantation in a subject.

As used herein the term "cryopreservation" or equivalents thereof refers to preservation of cells at temperatures below freezing.

As used herein the term "hibernation" or equivalents thereof refers to preservation of cells at temperatures above freezing and sufficiently below normal physiological temperature such that one or more normal cellular physiological processes are decreased or halted. In one embodiment, preferred hibernation temperatures range between 0 and 4° C., preferably about 4° C. Hibernation medium as used herein includes any medium which lacks a cryopreservative and is physiologically compatible for storage of a cell at above freezing temperatures, preferably about 4° C. Hibernation includes short term storage.

As used herein the term "room temperature storage" or equivalents thereof refers to preservation of cells at normal physiological temperature. In one embodiment, preferred storage temperatures range between 4 and 37° C., preferably about 37° C. storage medium as used herein includes any medium which lacks a cryopreservative and is physiologically compatible for storage of a cell at normal physiological temperature, preferably about 37° C. Storage includes short term storage.

As used herein the term "preservation solution" or equivalents thereof refers to cryopreservation solutions, hibernation solutions or room temperature storage solutions. These preservation solutions are known in the art and specific examples are described throughout this specification. For example room temperature preservation solutions are described in Example 6 and include as a specific example DB media. Hibernation preservation solutions are also described in Example 6 and include as a specific example SPS-1 media.

Hibernation Conditions

Hibernation temperatures typically range from between 0 and 5° C., preferably about 4° C. Numerous types of media can be used as hibernation media in conjunction with the instant methods. Prior art methods for freezing and hibernating cells utilize complex media comprising buffers and added protein, sometimes including entirely undefined components, such as serum. However, to minimize toxicity and immunogenicity such additives are not desirable for transplantation into humans. In preferred embodiments, hibernation media is free of added Ca.sup.++. In certain embodiments, medium for hibernating cells is free of added protein and/or free of a buffer. A preferred hibernation medium includes or consists of minimal amounts of glucose or moderate amounts of glucose in a saline solution, e.g., either no additional glucose or between about 0.1%-0.9% glucose in saline. In preferred embodiments, the hibernation medium includes or consists of about 0.1-0.5% glucose. In a more preferred embodiment, the medium includes or consists of about 0.2% glucose. In preferred embodiments, the hibernation medium includes or consists of a very small percentage (vol/vol) of NaCl, e.g., about 0.1-1% NaCl, preferably about 0.5-0.9% NaCl. In certain embodiments, more complex media can be used, e.g., Hank's balanced salt solution, Dulbecco's minimal essential medium, or Eagle's modified minimal essential medium. In certain embodiments it may be desirable to supplement the chosen hibernation medium with additives, for example, added protein (e.g., mammalian serum protein or whole serum (preferably heat inactivated)) buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2-3 mM), sorbitol (e.g., at about 300 mM) or other additives as are well known in the art.

In certain embodiments, the cells are hibernated at about 0-5° C., preferably about 4° C. In certain embodiments, cells are maintained at about 4° C. in hibernation medium prior to freezing or use. In other embodiments, the cells are maintained at about 4° C. in hibernation medium post freezing. In still other embodiments, the cells are maintained at about 4° C. in hibernation medium without freezing. In certain embodiments, the cells are maintained in hibernation medium at about 4° C. for at least about 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days prior to freezing, post freezing or prior to use in transplantation. In other embodiments, the cells are maintained in hibernation medium at about 4° C. for at least about 12-72 hours prior to freezing, post freezing or prior to use in transplantation. In certain embodiments the cells are maintained at 4° C. in hibernation medium for at least about 24 hours prior to freezing, post freezing or prior to use in transplantation. In a more preferred embodiment, the cells are maintained in hibernation medium from at least about 36-48 hours at about 4° C. prior to freezing, post freezing or prior to use.

Cyropreservation Conditions

In some embodiments cells are cryopreserved using a cryopreservation solution. A cryopreservation solution or medium includes a solution which contains a cryopreservative, i.e., a compound which protects cells against intracellular and/or cell membrane damage as the cells are frozen or thawed. A cryopreservative is identified by enhanced viability and/or functionality of cells in contact with the cryopreservative when compared with cells which are similarly frozen or thawed in the absence of the cryopreservative. Any cryopreservative can be used in conjunction with the instant methods and the term is meant to encompass both intracellular and extracellular cryopreservatives.

Any cryopreservative known in the art can be used in a cryopreservative solution. In certain embodiments, cryopreservation solutions include intracellular cryopreservatives including but not limited to dimethylsulfoxide (DMSO), various diols and triols (e.g., ethylene glycol, propylene glycol, butanediol and triol and glycerol), as well as various amides (e.g., formamide and acetamide); and extracellular cryopreservatives including but not limited to phosphomono and phosphodiester catabolites of phosphoglycerides, polyvinylpyrrolidone, or methylcellulose (e.g., at least 0.1%) can also be used alone or in combination with any of the intracellular cryopreservatives.

In preferred embodiments, DMSO is used as the cryopreservative. DMSO can be used at a wide range of concentrations, e.g., about 1%, about 2%, about 3%, about 4%, about 5%, about 6%, about 7%, about 8%, about 9%, about 10%, about 11%, about 12%, about 13%, about 14%, about 15% or more. In more preferred embodiments the concentration of DMSO ranges from about 6% to about 12%. In particularly preferred embodiments the concentration of DMSO is about 10%.

In certain embodiments, the cryopreservative is added to the cells in a stepwise manner in order to gradually increase the concentration of the cryopreservative until the desired final concentration of cryopreservative is achieved. In certain embodiments, the cells are contacted with a cryopreservation solution containing the cryopreservative at the desired final concentration or the cryopreservative is added directly to the base medium without a gradual increase in concentration.

The cryopreservation solution includes the cryopreservative in an appropriate base medium. Any type of media can be used for this purpose. In preferred embodiments, the base medium to which the cryopreservative is added is free of added Ca.sup.++. In certain embodiments the medium to which the cryopreservative is added is free of added protein and/or free of a buffer. In other embodiments, the base medium (e.g. DMEM or DMEM/F12) to which the cryopreservative is added includes or consists of about 0.1-0.5% glucose or no or low glucose. In some aspects of this embodiment, the base medium (e.g. DMEM or DMEM/F12) to which the cryopreservative is added includes or consists of about 0.5-0.9% NaCl. In preferred embodiments, the base medium to which the cryopreservative is added includes or consists of very low to no glucose and about 0.5-0.9% NaCl. In another preferred embodiment, the base medium to which the cryopreservative is added includes or consists of about 0.1 to 0.2% glucose. In some aspects of this embodiment, the base medium to which the cryopreservative is added includes or consists of about 0.5-0.9% NaCl.

In certain embodiments the cryopreservation solution can also contain added protein, for example, serum, e.g., fetal calf serum or human serum, or a serum protein, e.g., albumin or knockout serum replacement. In other embodiments, the cryopreservative can also contain other additives, such as those described above for inclusion in hibernation media, for example, antioxidants, growth factors, KCl (e.g., at about 30 mM), lactate (e.g., at about 20 mM), pyruvate, $MgCl_2$ (e.g., at about 2-3 mM), sorbitol (e.g., to an osmolarity of about 300 mM) or other additives as are well known in the art.

Once the cells are suspended in cryopreservation solution, the temperature of the cells is reduced in a controlled manner. In cooling the cells to below freezing, the reduction in temperature preferably occurs slowly to allow the cells to establish an equilibrium between the intracellular and extracellular concentration of cryopreservative such that intracellular ice crystal formation is inhibited. In some embodiments, the rate of cooling is preferably fast enough to protect the cells from excess water loss and the toxic effects of cryopreservatives. The cells can then be cryopreserved at a temperature of between −20° C. and about −250° C. Preferably, the cells are stored below −90° C. to minimize the risk of ice recrystallization. In particularly preferred embodiments, the cells are cryopreserved in liquid nitrogen at about −196° C. Alternatively, controlled freezing may be accomplished with the aid of commercially available electronically controlled freezer equipment.

Thawing Conditions

After cryopreservation, the cells can be thawed through any available method. In a preferred embodiment, the cells are thawed rapidly, e.g., by quick immersion in liquid at 37° C. Once the cells are thawed, dilution of the cryopreservative is accomplished by addition of a dilution medium.

Any media can be used for diluting the cryopreservation solution which is in contact with the thawed cells. For example, any of the media listed above for use in hibernating cells, or for growth and differentiation of cells, can be used for diluting the cryopreservation solution. Other media are also appropriate, for example, Hank's balanced salt solution (preferably without Ca++), DMEM containing media with no glucose or minimal to low amounts of glucose. Additives, e.g., as listed above for inclusion in hibernation or freezing media can also be used in media for dilution. Exemplary additives include, for example, buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2-3 mM), sorbitol (e.g., to an osmolarity of about 300 mM) or others additives as are well known in the art. Another suitable additive includes DNase (e.g., commercially available from Genentech, Incorporated as PULMOZYMEOR). The medium which is used for diluting the cryopreservation solution can, optionally, contain added protein, e.g., added protein (e.g., mammalian serum (preferably heat inactivated) or a serum protein such as albumin. In other embodiments, the medium contains no added protein and/or no added buffer.

After dilution of the cryopreservative, the cells can then be allowed to settle or a pellet of cells can be formed under centrifugal force in order to remove as much of the cryopreservation solution from the cells as possible. The cells can then be washed in medium which does not contain a cryopreservative. It may be preferable for the cells to remain at room temperature after the addition of the wash media and prior to letting the cells settle or form a pellet under centrifugal force. In preferred embodiments, the cells remain at room temperature for about 10, 15, 20, 30 minutes prior to the second centrifugation. Any medium known in the art can be used to wash the cells, for example, any of the hibernation or dilution media set forth above can be used.

After thawing and washing, cells are cultured at 37° C. for varying lengths of time to allow recovery prior to transplantation. Cells can be cultured in any culture medium, preferably in medium appropriate to their stage of differentiation. During this time some cell may death occur.

For use in transplantation, cells should be suspended in a final medium which is suitable for administration to a subject. Transplantation of cells is substantially similar to that described in U.S. Pat. No. 7,534,608, which is herein incorporated by reference in its entirety.

In addition, the thawed cells may be maintained in hibernation medium as described above at between 0 and 37° C., preferably about 4° C. for up to 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days prior to use in transplantation without a significant loss in viability. In some embodiments, no statistically significant loss in cell viability occurs.

Determining Viability of Recovered Cells

After storage, it may be desirable to assay the viability and/or functionality of the cells prior to transplantation to confirm their suitability for use, e.g., in transplantation. This can be accomplished using a variety of methods known in the art. For example, the cells can be stained using vital stains, such as, e.g., trypan blue or ethidium bromide or acridine orange. In certain embodiments, a population of cells suitable for transplantation is at least between about 50-100% viable. In preferred embodiments, a population of cells suitable for transplantation is at least about 50%, is at least about 55%, is at least about 60%, is at least about 65%, is at least about 70%, is at least about 75%, is at least about 80%, is at least about 85%, is at least about 90%, is at least about 95%, is at least about 96%, is at least about 97%, is at least about 98%, is at least about 99%, viable. In particularly preferred embodiments, such a population of cells is at least about 85% viable.

In other embodiments, the morphometric characteristics of the cells can be determined as a measure of the suitability of cells for use in transplantation. In preferred embodiments, the morphology of cells which have been stored using the instant methods and are suitable for transplantation does not differ (e.g., statistically significant) from that of fresh cells. In preferred embodiments, the in vivo morphology of cells which have been stored using the instant methods and are suitable for transplantation does not differ (e.g., statistically significant) from that of fresh cells.

In the case of cell clusters, cell mass can be quantitated before and after cell freeze/thaw and recovery. In one embodiment, cell clusters cultured in suspension can be manipulated to pack in closely. The area occupied by the clusters can then be photographed and measured. By comparing the areas occupied by cells before and after freeze/thaw and recovery, a value for percent recovery can be determined.

Cells which have been stored can also be assayed for the presence of certain hES and/or pancreatic progenitor or hormone secreting cell markers to determine if they are suitable for use in transplantation. This method has been described in detail in the above in Kroon et al. 2008, supra or in U.S. Pat. No. 7,534,608, which are herein incorporated by reference in its entireties.

Additionally, or alternatively, the cells can be tested for their functionality, e.g. as discussed in Kroon et al. 2008, supra or in U.S. Pat. No. 7,534,608, which are herein incorporated by reference in its entireties.

Encapsulation Devices

One embodiment described herein relates to encapsulation devices. Such devices can be implanted into a mammal to treat a variety of diseases and disorders. In preferred embodiments, the device comprises a biocompatible, immuno-isolating device that is capable of wholly encapsulating a therapeutically biologically active agent and/or cells therein. For example, such devices can house therapeutically effective quantities of cells within a semi-permeable membrane having a pore size such that oxygen and other molecules important to cell survival and function can move through the semi-permeable membrane but the cells of the immune system cannot permeate or traverse through the pores. Similarly, such devices can contain therapeutically effective quantities of a biologically active agent, e.g., an angiogenic factor, a growth factor, a hormone and the like.

The devices described herein can be employed for treating pathologies requiring a continuous supply of biologically active substances to the organism. Such devices are, for example, can also be referred to as, bioartificial organs, which contain homogenous or heterogenous mixtures of biologically active agents and/or cells, or cells producing one or more biologically active substances of interest. Ideally, the biologically active agents and/or cells are wholly encapsulated or enclosed in at least one internal space or are encapsulation chambers, which are bounded by at least one or more semi-permeable membranes. Such a semi-permeable membrane should allow the encapsulated biologically active substance of interest to pass (e.g., insulin, glucagon, pancreatic polypeptide and the like), making the active substance available to the target cells outside the device and in the patient's body. In a preferred embodiment, the semi-permeable membrane allows nutrients naturally present in the subject to pass through the membrane to provide essential nutrients to the encapsulated cells. At the same time, such a semi-permeable membrane prohibits or prevents the patient's cells, more particularly to the immune system cells, from passing through and into the device and harming the encapsulated cells in the device. For example, in the case of diabetes, this approach can allow glucose and oxygen to stimulate insulin-producing cells to release insulin as required by the body in real time while preventing immune system cells from recognizing and destroying the implanted cells. In a preferred embodiment, the semi-permeable membrane prohibits the implanted cells from escaping encapsulation.

Preferred devices may have certain characteristics which are desirable but are not limited to one or a combination of the following: i) comprised of a biocompatible material that functions under physiologic conditions, including pH and temperature; examples include, but are not limited to, anisotropic materials, polysulfone (PSF), nano-fiber mats, polyimide, tetrafluoroethylene/polytetrafluoroethylene (PTFE; also known as TEFLON®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes; ii) releases no toxic compounds harming the biologically active agent and/or cells encapsulated inside the device; iii) promotes secretion or release of a biologically active agent or macromolecule across the device; iv) promotes rapid kinetics of macromolecule diffusion; v) promotes long-term stability of the encapsulated cells; vi) promotes vascularization; vii) comprised of membranes or housing structure that is chemically inert; viii) provides stable mechanical properties; ix) maintains structure/housing integrity (e.g., prevents unintended leakage of toxic or harmful agents and/or cells); x) is refillable and/or flushable; xi) is mechanically expandable; xii) contains no ports or at least one, two, three or more ports; xiii) provides a means for immuno-isolating the transplanted cells from the host tissue; xiv) is easy to fabricate and manufacture; and xv) can be sterilized.

The embodiments of the encapsulation devices described herein are in not intended to be limited to certain device size, shape, design, volume capacity, and/or materials used to make the encapsulation devices, so long as one or more of the above elements are achieved.

Device Designs

In one embodiment, the encapsulated device is improved by creating one or more compartments in the device, other than that created by sealing or welding the device around the periphery or edges to prevent leakage of the cells and/or biologically active agents. FIGS. 1A-1I are examples of a schematic of one embodiment of the device, but the device is not intended to be bound to just this design. Rather, the design can include variations such as those routine in the art. In some embodiments, device design can be modified depending on the type of biologically active agents and/or cells encapsulated and to meet the needs and function of the study. A device of any size or shape reasonable can be further compartmentalized into having at least 1, at least 2, at least 3, at least 4, at least 5, at least 6, at least 7, at least 8, at least 9, at least 10, at least 11, at least 12, at least 13, a least 14, at least 15, at least 16, least 17, at least 18, at least 19, at least 20, at least 21, at least 22, at least 23, at least 24 or more chambers or compartments. One purpose for creating a plurality of compartments is that it limits cell aggregates or clusters or agglomerations such that cells packed in the center of the large clusters/agglomerations are denied, or receive less, nutrients and oxygen and therefore potentially do not survive. see FIGS. 1A-1I, 2A-2B, 3A-3B, 4A-4B, 5A-5C, and 6-11 for example. Devices containing a plurality of chambers or compartments therefore are better capable to disperse the cells throughout the chamber/compartment or chambers/compartments. In this way, there is more opportunity for each cell to receive nutrients and oxygen, thereby promoting cell survival and not cell death.

One embodiment relates to a substantially elliptical to rectangular shape device; see FIGS. 1A-1I, 2A-2B and 5A-5C. These devices are further compartmentalized or reconfigured so that instead of a slightly flattened device there is a weld or seam running through the center of the device, either sealing off each half of the device, thus forming two separate reservoirs, lumens, chambers, void spaces, containers or compartments; or the weld or seam creates one U-shaped chamber which is separated or divided in the middle due to the weld but such a weld in this instance does not completely seal off the chambers; see FIGS. 1C-1F and FIG. 2B also illustrate two ports, which provides for ease of filling and flushing cells into and through the chambers.

Figure 5A:
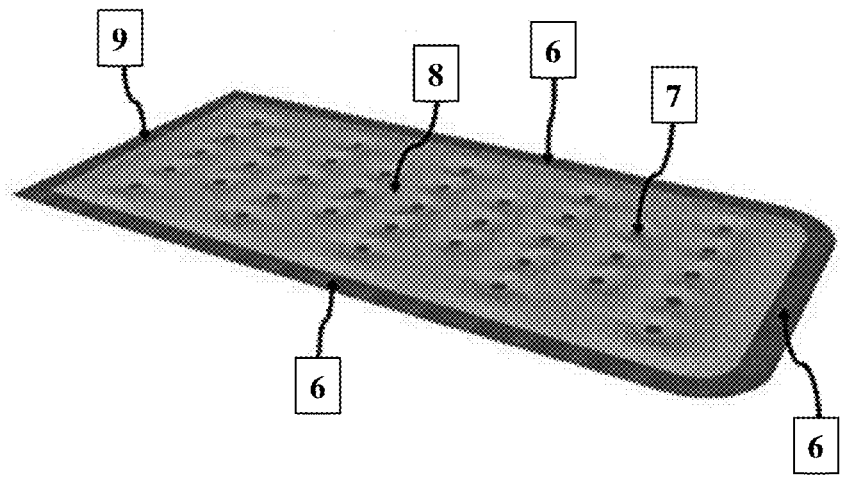
FIG. 5A is a cross-section of dual ported encapsulation device embodiment with an internal weld or seal.
Figure 5B:
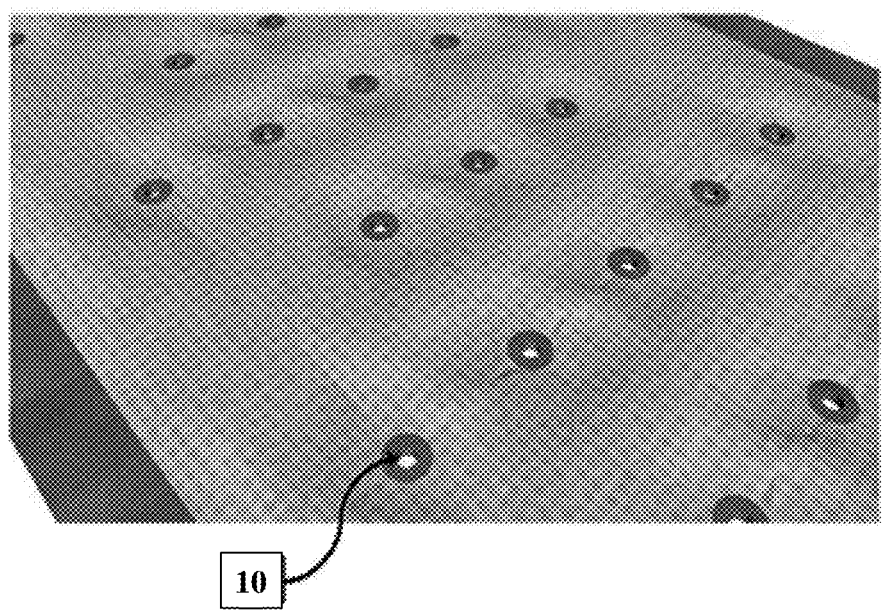
FIGS. 5B-5C are perspective views of an encapsulation device embodiment without loading ports and containing periodic ultrasonic spot-welds to compartmentalize the internal lumen.
Figure 5C:
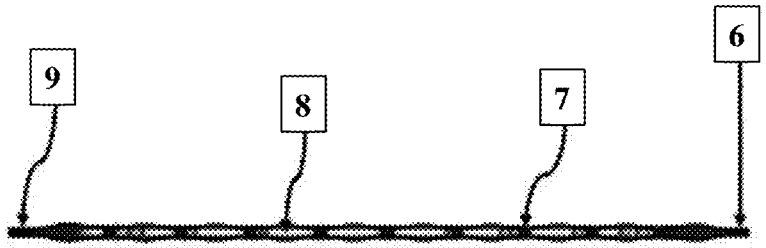

Another embodiment relates to a similar elliptical or rectangular shape device having 2, 3, 4, 5, 6, 7, 8, 9, 10 or more welds across the plane of the device; see FIGS. 5A-5C. In some aspects the welds are across the horizontal aspect or plane of the device. In other aspects the welds are across the vertical aspect or plane of the device. In still other aspects, intersecting welds are present across both the horizontal and vertical aspects of the plane. In some aspects the welds are parallel and equidistant to each other. In other aspects the welds are perpendicular. In still other aspects the welds are parallel but not equidistant. As in the above example, such a design can effectively form up to 2, 3, 4, 5, 6, 7, 8, 9, 10 or more chambers, wholly separated if the weld runs traverses and connects both boundaries of the device, or it can create one continuous chamber but interdigitated. Further, although certain exemplary devices are described in FIGS. 1A-1I, 2A-2B, 3A-3B, 4A-4B and 5A-5C with welds being parallel or parallel and equidistant, still other devices can be customized or made with welds in any direction or orientation, including long welds which have regions interrupted by no welds; and with device assemblies having one or more cell chambers. The type and number of welds and cell chambers used can depend on the cell population or agent employed and for what treatment or purpose. In some embodiments, welds can be arranged to modify the look of the device.

Figure 2B:
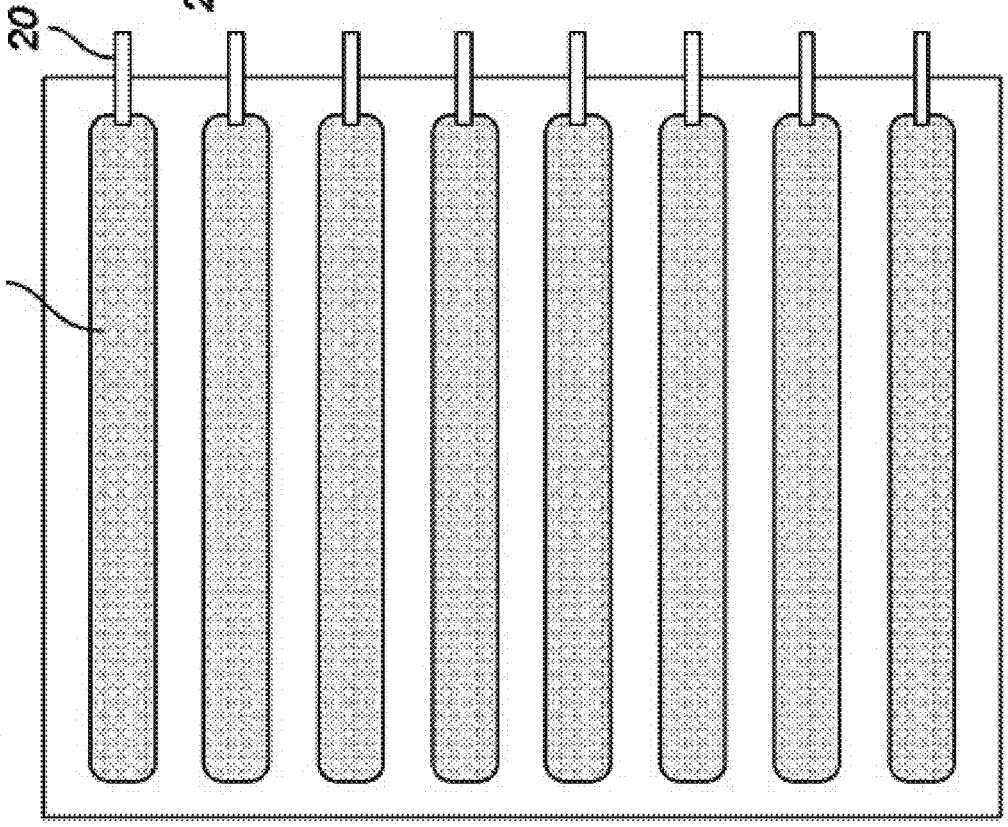

FIGS. 1A-1I show encapsulation device embodiments described herein, but as described above, these are preferred embodiments and one of ordinary skill in the art can envisage that by forming different configurations using welds or seams in any such device, one can customize the number of compartments suitable for the purpose. FIGS. 2A-2B, 3A-3B, 4A-4B and 5A-5C show top, side and end cross sections of the other device embodiments. The device can be ultrasonically welded around the entire perimeter 1 to create a completely enclosed internal lumen; see FIGS. 1A-1C and FIGS. 2A-2B. Other means of sealing or walling off membranes to form the pouch like device can be used. The lumen is further compartmentalized by an internal weld 2 that is centrally located and extends down the long axis of the device; see FIGS. 1D-1I. This weld extends to a point 3 that effectively limits the thickness or depth of each compartment yet does not completely segregate the internal lumen. By this approach, the width and depth of the compartments are controlled and can be varied as is required to enable cell product survival and performance. Moreover, all dimensions of the device, which include but are not limited to, the overall length, overall width, perimeter weld thickness, perimeter weld width, compartment length, compartment width, compartment depth, internal weld length, internal weld width and port position are design specifications that can be modified to optimize the device for unique cell products and/or biologically active agents, e.g. see modular device assembly as shown in FIGS. 2A-2B.

Referring to FIGS. 1A-1I, the compartment is loaded with a cell product or biologically active agent through two individual ports that are incorporated into the device during ultrasonic welding of the perimeter. These ports extend into the lumen or compartments and allow access to the compartment for the purpose of evenly distributing cells and/or agents during loading. Further, as the ports are connected via the U-shaped internal lumen as in FIGS. 1C-1F, gas is allowed to vent through each port while the adjacent port is being loaded, thus preventing the accumulation of pressure in the device.

Figure 3A:
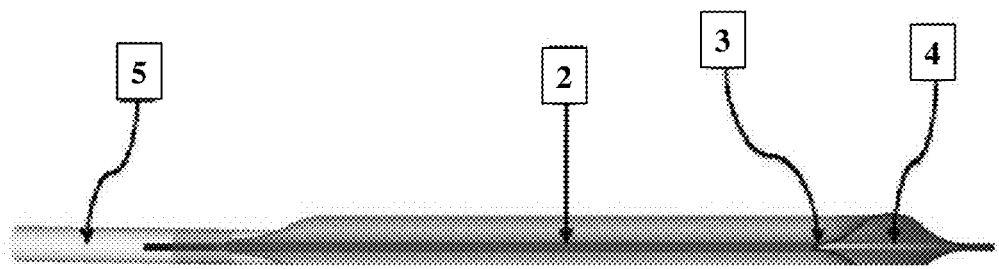
FIGS. 3A-3B are perspective views of a ported encapsulation device embodiment.
Figure 3B:
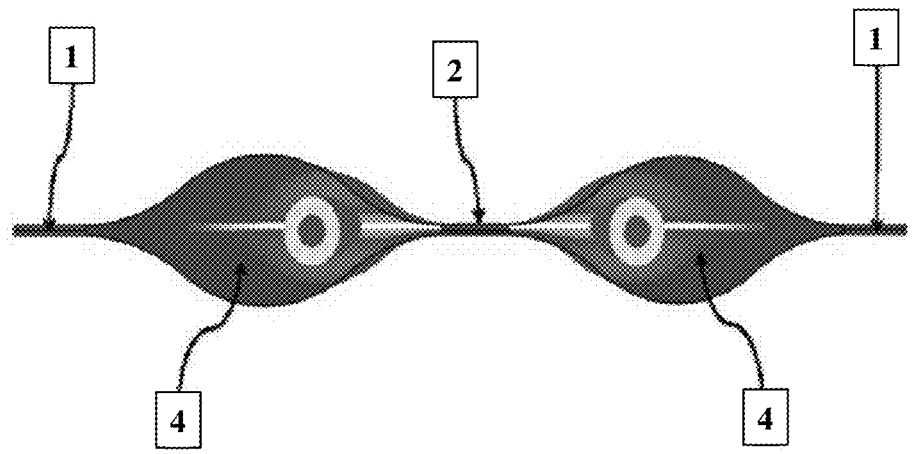

Alternatively, in another embodiment, the devices provided herein contain no ports of entry or exit, i.e. the devices are said to be port-less. Such an embodiment is shown in FIGS. 5A-5C. FIGS. 3A-3B show side (FIG. 3A) and end cross section (FIG. 3B) views of a device embodiments with a single (FIG. 3A) or dual (FIG. 3B) port and both having an internal weld down the long axis of the device. A two, three or more stage welding process may be necessary to create a port-less device as that shown in FIGS. 5A-5C. For example, in one aspect, the elliptical/rectangular outer perimeter 6 and the compartmentalization spot welds 7 are first created by ultrasonic welding. The spot welds 7 in FIGS. 5A and 5C function similarly to the internal weld 2 of FIGS. 1A-1I. The spot welds 7 of FIG. 5C are placed is a manner across the device to periodically limit the expansion of the lumen or compartment 8 at any given point. Again, the lumen or compartments 8 created by spot welding, therefore interconnecting the compartments 8, and not isolating or wholly separating any one lumen or compartment. Moreover, the total number, diameter and distribution of the spot welds 7 are design parameters that can be optimized to accommodate the loading dynamics and growth rates of any cell product or agent.

Once cells are loaded into the device, the outer perimeter is completely and aseptically sealed by a second ultrasonic weld across the edge 9 (FIGS. 5A and 5C) of the device. The result of the multi-step sealing process is that finished devices are totally enclosed and have no ports extending from the perimeter. This approach simplifies the loading process and improves the overall integrity and safety of the device, as the ports can be an area of the perimeter where breaches can occur as a result of suboptimal ultrasonic welding.

Further, although the above process was described in two sequential steps, the means for encapsulating the cells and/or agents is not limited to the described two steps but to any number of steps, in any order, necessary to encapsulate the cells and at the same time prevent or reduce the level of breach of the device.

In another embodiment, FIG. 5B shows an encapsulation device substantially similar to the device shown in FIG. 5A, but the spot welds 10 have been modified during the welding process to have the centers removed. One of ordinary skill in the art can accomplish this in various ways, e.g., by using an ultrasonic sonotrode that has an internal sharpened edge, which can cut the material immediately after welding. These cut-out welds 10 have an advantage in that they are more readily integrated with the host tissue because the cut-out welds 10 promote vascularization of the device, thus improving the survival and performance of oxygen-dependent cell products and/or agents. As a consequence of facilitating and promoting new vasculature through the device, there is improved diffusive transport of oxygen in the X-Y direction, which is normally limited towards the center of planar sheet devices.

In other embodiments, the device design can be different shapes, e.g. the cell encapsulation device can be in the shape of a tube or flattened tube or any other such shape which satisfies one of the above requirements for a device of the invention.

Device Materials

Cell permeable and impermeable membranes comprising of have been described in the art including those patents previously described above by Baxter or otherwise previously referred to as TheraCyte cell encapsulation devices including, U.S. Pat. Nos. 6,773,458; 6,520,997; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are herein incorporated by reference in their entireties.

In one embodiment, the encapsulating devices are comprised of a biocompatible material including, but are not limited to, anisotropic materials, polysulfone (PSF), nanofiber mats, polyimide, tetrafluoroethylene/polytetrafluoroethylene (PTFE; also known as TEFLON®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes. These and substantially similar membrane types and components are manufactured by at least GORE®, PHILLIPS SCIENTIFIC®, ZEUS®, PALL® and DEWAL® to name a few.

Immobilized Device

Also provided is an implantable device, which is immobilized at an implantation site to maintain the encapsulated cell and/or biological active agent at the implantation site and permit diffusion of, for example, an expressed and secreted therapeutic polypeptide from the implantation site. In one aspect, the implantation site is at, or close in proximity to, the tissue or organ which is focus of the treatment.

In other aspects, where delivery of the secreted agent from the device is not location dependent and biodistribution of the agent is dependent on the vasculature, the device can be implanted in a remote location. For example, in a preferred embodiment, the biocompatible device is implanted subcutaneously under the skin on the forearm, or flank, or back, or buttocks, or leg and the like, where it substantially remains until such time as it is required for it to be removed.

Expandable Devices

Devices described herein have inner and outer surfaces wherein the device contains at least one void (or reservoir, or lumen, or container or compartment) and wherein at least one void is open to the inner surface of the device. Conventional implantable devices are commonly made of rigid, non-expandable biocompatible materials. One embodiment of the device described herein is made of an expandable material. Other embodiments are directed to non-expandable materials. Whether the device is capable of expanding may be an inherent part of the materials employed to make the device, e.g., a polymer sheath which is expandable, or can be designed such that they are expandable or have expandable capabilities. For example, a device which expands in size to house additional cells or to refill an existing device is provided.

In another embodiment, the implantable device is contained in a housing or holder, which is slightly more rigid, and non-expandable but allowing sufficient means to increase cell or agent capacity by increasing the number of or implant devices. For example, means for inserting an additional reservoir, lumen, container, compartment or cassette each having pre-loaded cells or agent. Alternatively, the housing contains a plurality of devices only some of which are loaded with cells or have cells encapsulated therein, while others are empty, which can be loaded and filled with cells or agents at a later period in time or any time subsequent the initial implantation. Such an expandable housing is comprised of inert materials suitable for implantation in the body, e.g., metal, titanium, titanium alloy or a stainless steel alloy, plastic, and ceramic appropriate for implantation in the mammal, more specifically, the human body.

Still in another embodiment, such a housing or implant device holder includes an outer sleeve having a longitudinal axis, at least one passage along the longitudinal axis, and a distal end and a device engagement area adapted to cooperatively engage the device. As an analogy, the device holder functions similarly to a disk or cassette holder capable of housing more than one disk or cassette at any one time or for a long period of time. In still another embodiment, the device holder contains an expander adapted to increase the height of the holder Refillable Cell Encapsulation Devices Another embodiment relates to an encapsulation device with a refillable reservoir, lumen, container or compartment, which can be periodically filled or flushed with appropriate therapeutic or biologically active agents and/or cells. Such filling may be accomplished by injecting a therapeutically effective amount of the appropriate therapeutic or biologically active agents and/or cells into an implanted reservoir, lumen, container or compartment, e.g., subdermally or subcutaneously using a syringe or other standard means in the art for filling like reservoirs, lumens, containers or compartments in vivo.

Large Capacity Cell Encapsulation Devices

FIGS. 4A-4B are an illustration of one embodiment, providing for devices or assemblies containing a plurality or multiplicity of cell chambers interconnected by cell-free zones, e.g. folds and bends. For example, one embodiment comprises multiple porous cell chambers that are laterally connected to each other. In one such embodiment, the multiple porous cell chambers are formed, for example, by ultrasonically welding the top and bottom surfaces of a porous material along a line substantially parallel to a longitudinal axis of the device and houses any of 2, 3, 4, 5, 6, 7, 8, 9, 10, 11, 12, 13, 14, 15, 16, 17, 18 or more cell chambers. Each cell chamber has a fixed volume capacity, e.g. 100 µL, with one or more ports and an internal matrix scaffold or foam, and, if desirable an internal weld or welds to periodically limit the expansion of the lumen or compartment. In one aspect, the cell encapsulation device described herein comprises at least 2 porous chambers or sufficient chambers to house an adequate human dosage of islets derived from pluripotent stem cells to treat and ameliorate a subject with diabetes once implanted. In a preferred embodiment, each chamber has a substantially same inner diameter and can hold about the same number of cells. The availability of multiple chambers allows the use of any number or combination of chambers depending on the volume of cellular preparation required, the disease treatment regimen prescribed, which is within the knowledge and skill of persons skilled in the art to determine.

In one embodiment of the invention, adjacent cell chambers in a multiple chamber device or assembly may take on different designs, volume capacity, cross-sectional dimensions and surface areas. In one aspect, multiple porous cell chambers are formed by ultrasonically welding the polymer mesh from a proximal end to a distal end creating cell-free zones at each weld. The top and bottom surfaces of cell chambers are continuous across the one or more cell chambers except where they are interrupted by ultrasonic weld lines or other forms of creating cell-free zones. The core or center of each cell chamber may contain a seal or a weld in the cell chamber interior to create a "cell free" zone in the center of the chamber, for the purpose of partitioning the chamber and reducing the possibility of a necrotic core of cells in the center of the device; which can occur when the diameter of the cell chambers becomes too big or too wide. Such cell-free zones or welds are also described in Applicant's U.S. Pat. No. 8,278,106, specifically FIGS. 2-7 and Applicant's device Design applications previously mentioned. These cell-free zones or welds can be bent or folded at an angle e.g. at 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, and 180 degrees, which provides a configuration to increase cell volume by adding more cell chambers to the device assembly while at the same time constrains or even at times reduces or decreases the footprint of the entire multiple chamber device assembly.

In a preferred embodiment of the invention, the devices are laterally connected to each other and separated by cell-free zones and/or welds. In one such embodiment, the multiple porous cell chambers are formed by ultrasonically welding the top and bottom surfaces of a porous material along a line substantially parallel to a longitudinal axis of the device and houses at least 2, 3, 4, 5, 6, 7, 8, 9, 10, 11, 12, 13, 14, 15, 16 or more cell chambers. Each chamber can house one or more ports on the same side or on opposing sides. Further each chamber can have an internal matrix scaffold and/or contain an internal weld.

Alternatively, individual cell chambers in any device or assembly need not have the same configuration or design. Each chamber can take on different characteristic designs including but not limited to cell chambers can contain an elastomeric foam, cell chambers with interior weld partitions as described previously in Applicant's U.S. Pat. No. 8,278,106, cell chambers with different outer mesh layers, cell chambers with different porous membranes, cell chambers with additional porous membranes (e.g. vascularizing membrane, or membrane that elutes certain factors to promote vascularization), cell chambers of different size to customize the cell dosage and the like. Multiple cell chamber devices or assemblies are important for the purpose of delivering high therapeutic effective doses to a patient while at the same time providing flexibility in the dosing scheme and not increasing the footprint of the device.

Encapsulated Cells

In some embodiments, the system comprises a cell density between about $1 \times 10^5$, $1 \times 10^6$ cells/mL to about $1 \times 10^{10}$ cells/mL or more. In some embodiments, the cell survives under culture conditions or in vivo in the system for at least a month, two months, three months, four months, five months, six months, seven months, eight months, nine months, ten months, eleven months, twelve months or a year or more with a functionality that represents at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more of the function expressed at the time the cells are/were introduced into the system or at the time the cells fully develop and/or mature in the system, e.g. implantation of progenitor cells which need to further develop or mature to functional cells in vivo. In some embodiments, the cell in the system expands in said system to increase in cell density and/or cell function upon implantation of the system in vivo.

In one embodiment, cells encapsulated in the 3-dimensional large capacity device assemblies include but are not limited to mesendoderm, definitive endoderm lineage type cells including but not limited to PDX-1 negative foregut, PDX-1 positive foregut, pancreatic endoderm (PE or PEC), pancreatic progenitors, endocrine precursors or progenitors, endocrine cells such as immature beta cells and the like. In general, definitive endoderm lineage cells may also include any cells derived from definitive endoderm and their derivatives and progeny including but not limited to the organs which derive from the gut tube such as the lungs, liver, thymus, parathyroid and thyroid glands, gall bladder and pancreas. See Grapin-Botton and Melton, 2000; Kimelman and Griffin, 2000; Tremblay et al., 2000; Wells and Melton, 1999; Wells and Melton, 2000. These and other definitive endoderm-lineage type cells have been described in detail by Applicant, at least in Other suitable embodiments described herein are further described in detail in at least U.S. Pat. No. 7,958,585, PREPRIMITIVE STREAK AND MESENDODERM CELLS; U.S. Pat. Nos. 7,510,876, 8,216,836, 8,623,645 DEFINITIVE ENDODERM; U.S. Pat. No. 8,129,182, ENDOCRINE PRECURSOR CELLS, PANCREATIC HORMONEEXPRESSING CELLS AND METHODS OF PRODUCTION; U.S. Pat. No. 8,278,106, ENCAPSULATION OF PANCREATIC CELLS DERIVED FROM HUMAN PLURIPOTENT STEM CELLS; and U.S. application Ser. No. 14/106,330, SEMIPERMEABLE MACRO IMPLANTABLE CELLULAR ENCAPSULATION DEVICES, filed Dec. 13, 2013.

Methods for Increasing Cell Viability

One obstacle to the field of cell and tissue encapsulation/immuno-isolation has been the lack of sufficient oxygen and nutrient transport across the polymer membranes used to encapsulate cells and tissues. The result of this insufficient gas and nutrient exchange is lowered metabolic activity and cell death. Embodiments described herein relate to an implantable cell encapsulation device addressing this drawback of the prior art.

Oxygen partial pressures have been measured within islets, in their native environment, after isolation, and post-transplant in various polymer devices as well as naked or free, for example, under the kidney capsule. Oxygen partial pressures in pancreatic islets are the highest of any organ in the body (37-46 mmHg). However, upon isolation, these values fall drastically (14-19 mm Hg). Upon transplantation of pancreatic islets into normo-glycemic animals the values decrease slightly (9-15 mmHg) as compare to their isolated values. See Dionne et al., Trans. Am. Soc. Artf. Intern. Organs. 1989; 35: 739-741; and Carlsson et al., Diabetes July 1998 47(7):1027-32, the disclosure of which is herein expressly incorporated by reference. These studies demonstrate that when tissues are immuno-isolated and transplanted, even in a vascularized region such as the kidney capsule, the oxygen partial pressures drop as compared to their native states (37-46 mmHg). Hence, these nearly anoxic conditions can result in cell death, particularly the nearer the cell to the core of a cell cluster or core of an encapsulating device.

In order to achieve better oxygen availability and delivery to the encapsulated cells or tissues and/or biologically active agents, embodiments described herein relate to the use of, for example, perfluorinated substances in the device design and/or formulation, e.g., in the membranes or materials employed for assembly of the device. In particular, perfluoro organic compounds, e.g., perfluorocarbons (PFCs), are good solvents because they have several fold higher solubility for oxygen than water. For example, under normal conditions, liquid PFCs dissolve between 40 and 55% by volume of oxygen and between 100 and 150% by volume of $CO_2$. PFCs are largely used as blood substitutes and tissue preservation. Additionally, PFC derivatives are dense, chemically inert, and water insoluble compounds that cannot be metabolized.

In another aspect of the embodiments, enhanced $O_2$ delivery is performed by a PFC-emulsion or mixture of PFC with some matrix. The device components or cells for example could be suspended or soaked or incubated in the emulsion/matrix to form a coating. Still certain PFC emulsions with higher weight/volume concentrations have been known to have improved oxygen delivery and retention properties. And because of the higher oxygen partial pressure created by the $O_2$ carrying capabilities of PFCs, an $O_2$ pressure gradient is created that drives diffusion of dissolved oxygen into the tissue, thereby enhancing $O_2$ delivery to the cells.

The PFC substance includes but is not limited to perfluorotributylamine (FC-43), perfluorodecalin, perfluorooctyl bromide, bis-perfluorobutyl-ethene, or other suitable PFCs. Preferred PFCs typically contain about 60 to about 76 weight percent carbon-bonded fluorine. The perfluorinated fluids can be single compounds, but usually will be a mixture of such compounds. U.S. Pat. No. 2,500,388 (Simons); U.S. Pat. No. 2,519,983 (Simons); U.S. Pat. No. 2,594,272 (Kauck et al.); U.S. Pat. No. 2,616,927 (Kauck et al.); and U.S. Pat. No. 4,788,339 (Moore et al.), the disclosures of which are herein incorporated by reference in their entireties. PFCs useful in the embodiments described herein also include those described in Encyclopedia of Chemical Technology, Kirk-Othmer, Third Ed., Vol. 10, pages 874-81, John Wiley & Sons (1980). For example, useful PFCs include perfluoro-4-methylmorpholine, perfluorotriethylamine, perfluoro-2-ethyltetrahydrofuran, perfluoro-2-butyltetrahydrofuran, perfluoropentane, perfluoro-2-methylpentane, perfluorohexane, perfluoro-4-isopropylmorpholine, perfluorodibutyl ether, perfluoroheptane, perfluorooctane, and mixtures thereof. Preferred inert fluorochemical liquids include perfluorohexane, perfluoro-2-butyltetrahydrofuran, perfluoroheptane, perfluorooctane, and mixtures thereof. Commercially available PFCs useful in the embodiments described herein include FLUORINERT™ fluids, e.g., FC-72, FC-75, FC-77 and FC-84, described in the 1990 product bulletin #98-0211-5347-7(101.5) NPI, FLUORINERT™ fluids, (available from Minnesota Mining and Manufacturing Company, St. Paul, Minn.), and mixtures thereof.

In Vivo Imaging Capability

In one embodiment, there is provided a means for imaging or detecting the cells inside the encapsulating devices in vivo. Imaging serves important roles in stem cell therapies. For example, noninvasive forms of imaging can be used to: (1) determine the presence, severity or phenotype of the cell and/or disease to be treated; (2) monitor engrafted cell therapies for the appearance of deleterious or non-target cell types and structures, such as cysts or microcysts; (3) guide the delivery of therapy; (4) follow the time-course of disease and evaluate the effects or efficacy of therapy; (5) provide labels and define mechanisms of therapy; (6) analyze and evaluate survival and function of engrafted cells; and (7) generally facilitate the process of any cell therapy, e.g. by determining the engraftment, survival, and local function of cell therapy, including cell therapies described herein for treatment of diabetes by substitution and/or implanting pancreatic progenitor cells. In addition, although cell therapies aim to decrease morbidity/mortality, noninvasive imaging techniques as described herein and in more detail below can serve as a useful surrogate endpoint, for example, in preliminary trials or preclinical studies.

Any in vivo imaging technology is ideally: i) non-invasive; ii) reliably repetitive; iii) capable of tissue penetration up to a depth of at least 3 mm; iv) resolution capabilities of no greater than 100 μM and ideally no greater than 50 μM; v) imaging is not attenuated by device materials, e.g., can image through PTFE; vi) clinically compatible and not technically cumbersome or complicated; vii) commercially available; viii) FDA approved for human use; ix) reasonably cost-effective; and x) can image cells in a reasonable period of time (e.g., seconds or minutes), or any combination of the above.

To date, current methods include but are not limited to confocal microscopy, 2-photon microscopy, high frequency ultrasound, optical coherence tomography (OCT), photoacoustic tomography (PAT), computed tomography (CT), magnetic resonance imaging (MRI), single photon emission computed tomography (SPECT) and positron emission tomography (PET). These alone or combined can provide useful means to monitor the transplanted cells. Also, it is expected that such technologies will improve over time but that the essential tenets of how each technology functions or its utility is substantially similar. That said, in vivo imaging described herein is not intended to be limited to technologies described below but to technologies later discovered and described which would serve the same utility as that described herein.

In one embodiment, the imaging technique employed would be non-invasive and provide for a 3-dimensional tomographic data, have high temporal and spatial resolution, allow molecular imaging, and would be inexpensive and portable. While at present no single modality is ideal (discussed in more detail below), each has different attributes and these modalities together can provide complimentary information.

Confocal microscopy is an optical imaging technique that increases micrograph contrast and is capable of reconstructing three-dimensional images by using a spatial pinhole to eliminate out-of-focus light in specimens that are thicker than the focal plane. Since only one point in the sample is illuminated at a time, 2D or 3D imaging requires scanning over a regular raster (i.e. a rectangular pattern of parallel scanning lines) in the specimen. Three principal scanning variations are commonly employed to produce confocal microscope images. Fundamentally equivalent confocal operation can be achieved by employing a laterally translating specimen stage coupled to a stationary illuminating light beam (stage scanning), a scanned light beam with a stationary stage (beam scanning), or by maintaining both the stage and light source stationary while scanning the specimen with an array of light points transmitted through apertures in a spinning Nipkow or Nipkov disk. Each technique has performance features that make it advantageous for specific confocal applications, but that limits the usefulness of that feature for other applications.

All confocal microscopes rely on the ability of the technique to produce high-resolution images, termed optical sections, in sequence through relatively thick sections or whole-mount specimens. Based on the optical section as the basic image unit, data can be collected from fixed and stained specimens in single, double, triple, or multiple-wavelength illumination modes, and the images collected with the various illumination and labeling strategies will be in register with each other. Live cell imaging and time-lapse sequences are possible, and digital image processing methods applied to sequences of images allow z-series and three-dimensional representation of specimens, as well as the time-sequence presentation of 3D data as four-dimensional imaging. The use of above confocal microscopes is not limiting as other confocal microscopes now or later discovered are also encompassed in the embodiments described herein.

A large number of fluorescent probes are available that, when incorporated in relatively simple protocols, can stain certain cellular surface markers and/or proteins and intracellular organelles and structures, e.g., Celltracker, DiI, nuclear vital dyes, and the like. Fluorescent markers which specifically bind directly or indirectly to certain cell surface markers can be especially useful for identification of for example unwanted cell types. In one preferred embodiment, real time in vivo imaging for the presence of encapsulated pluripotent cells provides a means to detect, and therefore the potential to prevent, teratoma formation caused from pluripotent stem cells, such as hES or human embryonic gonadal cells or induced pluripotent stem (IPS) cells or parthenote cells and the like. The same means of detection can also identify pluripotent Stem cells which have escaped or leaked out of the device (or become un-encapsulated). Identification of such cells can also be performed using fluorescently labeled promoter genes OCT4 and NANOG that are up-regulated in expression in pluripotent stem cells. Similarly, certain intracellular fluorescent markers that label nuclei, the Golgi apparatus, the endoplasmic reticulum, and mitochondria, and even dyes such as fluorescently labeled phalloidins that target polymerized actin in cells, are also commercially available and can provide critical information about the fate of a cell.

In another embodiment, two-photon excited fluorescence (TPEF) microscopy is a noninvasive means to monitor differentiation or, stated in the reverse, to identify pluripotent stem cells (e.g., hESCs or IPS cells or parthenote cells) which did not differentiate and were inadvertently implanted as a very small percentage of the product cells that were encapsulated in the device described herein. Two-photon excited fluorescence microscopy relies substantially on endogenous sources of contrast, but can also detect, for example, fibrillar matrix molecules via second harmonic generation. In brief, two-photon microscopy relies on fluorescence emission similar to that employed by confocal microscopy. Rice et al. (2007) described that TPEF can be used to reveal quantitative differences in the biochemical status and the shape of differentiating and nondifferentiating stem cells in two-dimensional (2-D). See Rice et al. (2007) J Biomed Opt. 2007 November-December; 12(6), the disclosure of which is expressly incorporated by reference herein. In one embodiment, pluripotent stem cells can be genetically modified to express a fluorescent protein, e.g., enhanced green fluorescent protein, and driven by a pluripotent stem cell promoter (e.g., OCT4 or NANOG or any other pluripotent stem cell promoter later identified). For those implantable devices that are deeper than subcutaneous implants, i.e. deep below the skin surface, two-photon provides for a non-invasive deeper imaging than confocal microscopy. Further, the infrared light used is less harmful to living cells than visible or ultraviolet exposure, as the photon energy required for fluorescence excitation only occurs at the plane of focus and is not experienced by cells or tissues in the out-of-focus planes.

In still another embodiment, ultrasound is portable, essentially harmless, versatile, and can be done in real-time at the time of implantation of the encapsulated cell product and/or encapsulated biologically active agent or as a monitoring tool over the course of implantation. In particular, conventional low and/or corresponding high-frequency ultrasound can be used to provide qualitative as well as quantitative spectroscopic data. Although high-frequency ultrasound is capable of increased imaging resolution (30-80 μm over 20-50 MHz) as compared to clinical low-frequency ultrasounds (80 μm-1.5 mm over 1-20 MHz), it suffers from limited tissue penetration depth and limiting its use to superficial tissue sites. High-resolution imaging enables in vivo assessment of anatomical structures and hemodynamic function in longitudinal studies of a mammal. For example, Vevo by VisualSonics offers: (1) ability to perform longitudinal studies of disease progression and regression in individual subjects; (2) image resolution of anatomical and physiological structures of down to 30 microns; (3) ability to visualize image-guided needle injection and extraction; (4) microcirculatory and cardiovascular blood flow assessment; (5) high throughput via user-friendly equipment and research-driven interface; and (6) open architecture allowing comprehensive measurement and annotations and offline data analysis. The ability to assess microcirculatory and cardiovascular blood flow will assist in determining the viability of the cells, e.g. $O_2$ flow and delivery. In comparison, low-frequency ultrasound (about 7-10 mHz) has been shown to detect microstructural tissue changes that correlated with histological cell death in acute myeloid leukemia cells exposed to chemotherapy. See Azrif et al., Conventional low-frequency ultrasound detection in apoptosis, *Proceedings of the American Institute of Ultrasound in Medicine, New York, N.Y.* 2007 (AIUM Laura M.D., 2007) p.S185.

In another embodiment, magnetic resonance imaging (MRI) can be utilized to distinguish between healthy and diseased tissue using a contrast agent. Yet, in another embodiment, computerized tomography (CT) or CT scans can be used to create a detailed picture of the body's tissues and structure. Again here, a contrast agent is utilized and makes it easy to visualize abnormal tissue due to specific absorption rates. One use of a contrast agent such as Indium-111 (I-111) oxine is for tracking stem cells although it does have a short half-life. Still, in another embodiment, Positron Emission Tomography (PET) scans can be used to measure emissions from positron-emitting molecules e.g., carbon, nitrogen, and oxygen to name a few, and provide valuable functional information. In yet another embodiment, optical coherence tomography (OCT) or photoacoustic tomography (PAT) may also be used to examine cells and tissues inside and outside the device. OCT detects differences in the reflectivity of various tissues while PAT detects ultrasonic waves created when tissues are heated by exposure to low energy laser light.

Having generally described this invention, a further understanding can be obtained by reference to certain specific examples which are provided herein for purposes of illustration only, and are not intended to be limiting.

EXAMPLES

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

It is understood that an important feature of the cryopreservation techniques below is that all involve the cryopreservation of PEC aggregates, not single cells.

It will be appreciated that the methods and compositions described below cryopreservation of PEC aggregates derived from hES cells. However, the above-described cryopreservation techniques can be utilized with other cell types including, pluripotent stem cells (including hES), definitive endoderm, primitive gut tube or foregut endoderm, posterior foregut, Pdx1-positive endoderm, or endocrine cells, or immature endocrine cells, specifically, immature beta cells. The above described cryopreservation techniques can be utilized with PEC derived from other cell types such as iPEC (PEC aggregates derived from induced pluripotent stem cells), or PEC made from other pluripotent stem cells which do not involve the destruction of a human embryo or non-embryonic pluripotent cells such as ICM/epiblast cells, primitive ectoderm cells, primordial germ cells, and teratocarcinoma cells. The above-described cryopreservation techniques can be utilized with other cell lineages including mesoderm (bone muscle, blood), ectoderm (neural, skin).

It is understood that the treatments described below limit spontaneous differentiation and ideally promote survival of cell types of interest such as non-endocrine cells compared to endocrine and residual cell types.

Example 1

Cryopreserving and Thawing PEC Aggregates

Because cell transplantation is hindered by the lack of available cell sources and operational and logistical problems, there is a need to provide an unlimited pancreatic cell source for transplantation at times convenient to the patient.

Here, Applicant explored various cryopreservation conditions to optimize cell survival following cryopreservation. Cryopreservation conditions analyzed include, but are not limited to dimethyl sulfoxide (DMSO) equilibration time (e.g., 30 vs. 60 minutes), base medium composition (DMEM/XF/DMSO/Hepes vs. Cryostor 5 and cryostor 10), transition temperature to rapid cool (−35° C., −40° C., −65° C.), DMSO equilibration temp (room temperature vs. 4° C.), Equilibration time and temp (4° C. for 1 hr, RT for 45 min, RT for 15 min to 4° C. for 45 min), Thaw media temp (room temperature, 4° C.), slow cool rate (0.5° C./min, 0.2° C./min, 0.1° C./min). These many iterative experiments were tested alone, or in combination, to determine how cell survival following cryopreservation could be optimized. Such optimized cryopreservation and thawing protocols produce PEC aggregates with optimized cell survival following cryopreservation.

As a specific example, cell incubation time in the cryopreservation solution was tested. It is well known that extended periods of time in DMSO is detrimental to cell survival and viability, for example, time periods greater than 20 minutes. However, a certain time period of incubation in DMSO is necessary for equilibration of DMSO intracellularly. Hence, Applicants elucidated the optimal time period for DMSO incubation of PEC.

Pancreatic progenitor cells (or PEC) were differentiated to day 13 substantially as described in U.S. Pat. Nos. 8,008,075, 8,278,106, 7,510,876, 7,534,608, 7,993,920, 7,695,965; U.S. application Ser. Nos. 12/618,659 and 13/205,511; Schulz et al. supra, (2012); Kroon et al. (2008) supra, D'Amour et al. (2006) supra, and in Table 5 below. The PEC aggregates were centrifuged and then resuspended in cryopreservation solution containing DMEM with 30% Xeno-free Knockout Serum Replacement, 25 mM HEPES and 10% DMSO solution. Cells were aliquoted into freezing vials and equilibrated in cryopreservation solution for about 30 or 60 minutes at ambient temperature. Although cells were equilibrated in cryopreservation solution for about 30 or 60 minutes, it is expected that the cells could be equilibrated for longer for example 90 minutes, 120 minutes, 2 hours, 3 hours, 5 hours, 8 hours, 24 hours or even longer without deleteriously affecting the viability or later in vivo function of the cells.

TABLE 5

Manufacturing Method for Making Pancreatic Endoderm Cells (PEC) and Endocrine Cell Populations

| Days | Stage | Protocol #1: Standard PEC Production | Protocol #2: Production of PEC with Higher Non-Endocrine Sub-Populations | Days | Protocol #3: Production of Endocrine Cell Population (Composite) |
|---|---|---|---|---|---|
| −1 |   | XF HA; SP | XF HA; SP | −1 | XF HA; SP |
| 0 | 1 | r0.2FBS-ITS1:5000 A100 W50 | r0.2FBS-ITS1:5000 A100 W50 | 0 | r0.2FBS-ITS1:5000 A100 W50 |
| 1 |   | r0.2FBS-ITS1:5000 A100 | r0.2FBS-ITS1:5000 A100 | 1 | r0.2FBS-ITS1:5000 A100 |
| 2 | 2 | r0.2FBS-ITS1:1000 K25 IV | r0.2FBS-ITS1:1000 K25 IV | 2 | r0.2FBS-ITS1:1000 K25 IV |
| 3 |   | r0.2FBS-ITS1:1000 K25 | r0.2FBS-ITS1:1000 K25 | 3 | r0.2FBS-ITS1:1000 K25 |
| 4 |   | r0.2FBS-ITS1:1000 K25 | r0.2FBS-ITS1:1000 K25 | 4 | r0.2FBS-ITS1:1000 K25 |
| 5 | 3 | db-CTT3 N50 | db-CTT3 N50 A50 H5 W50 | 5 | db-CTT3 N50 A50 H5 W50 |
| 6 |   | db-CTT3 N50 | db-CTT3 N50 A50 H5 W50 | 6 | db-CTT3 N50 A50 H5 W50 |
| 7 |   | db-CTT3 N50 | db-CTT3 N50 A50 H5 W50 |   |   |
| 8 | 4 | db-N50 K50 E50 | db-N50 K50 E50 A5 H5 | 7 | db-N50 K50 E50 A5 H5 |
| 9 |   | db-N50 K50 E50 | db-N50 K50 E50 A5 H5 | 8 | db-N50 K50 E50 A5 H5 |
| 10 |   | db-N50 K50 E50 | db-N50 K50 E50 A5 H5 | 9 | db-N50 K50 E50 A5 H5 |
| 11 |   | db-N50 K50 E50 | db-N50 K50 E50 A5 H5 | 10 | db-N50 K50 E50 A5 H5 |
| 12 |   | db-N50 K50 E50 | db-N50 K50 E50 | 11 | db-N50 K50 E50 |
| 13 |   | db-N50 K50 E50 (optional) | db-N50 K50 E50 | 12 | db-N50 K50 E50 |
| 14 | 5 | Transplanted | Transplanted | 13 | db-N50 K50 E50 R01 NC10 |
| 14 |   |   |   | 14 | db-N50 K50 E50 R01 NC10 |
| 15 | 6 |   |   | 15 | db-Y10 MG0.05 SHH100 NC10 IGF50 BMP10 |
| 16 |   |   |   | 16 | db-Y10 MG0.05 SHH100 NC10 IGF50 BMP10 |
| 17 |   |   |   | 17 | db-Y10 MG0.05 SHH100 NC10 IGF50 BMP10 |
| 18 |   |   |   | 18 | db-Y10 MG0.05 SHH100 NC10 IGF50 BMP10 |
| 19 |   |   |   | 19 | db-Y10 MG0.05 SHH100 NC10 IGF50 BMP10 |
| 20 | 7 |   |   | 20 | db- MG0.05 SHH100 NC10 IGF50 BMP10 |
| 21 |   |   |   | 21 | db-FBS BMP10 TTNPB1 IGF50 |
| 22 |   |   |   | 22 | db-Y10 MG0.05 BMP10 TTNPB1 IGF50 |
| 23 |   |   |   | 23 | db-Y10 MG0.05 BMP10 TTNPB1 IGF50 |
| 24 |   |   |   | 24 | db-Y10 MG0.05 BMP10 TTNPB1 IGF50 |
| 25 |   |   |   | 25 | db-Y10 MG0.05 BMP10 TTNPB1 IGF250 |
| 26 |   |   |   | 26 | db-Y10 MG0.05 BMP10 TTNPB1 IGF250 |
| 27 |   |   |   | 27 | db-Y10 MG0.05 BMP10 TTNPB1 IGF250 |

TABLE 5-continued

Manufacturing Method for Making Pancreatic Endoderm Cells (PEC) and Endocrine Cell Populations

| Days | Stage | Protocol #1: Standard PEC Production | Protocol #2: Production of PEC with Higher Non-Endocrine Sub-Populations | Days | Protocol #3: Production of Endocrine Cell Population (Composite) |
|---|---|---|---|---|---|
| 28 | | | | 28 | db-Y10 MG0.05 BMP10 TTNPB1 IGF250 |
| 29 | | | | 29 | db-Y10 MG0.05 BMP10 TTNPB1 IGF250 |
| 30 | | | | 30 | db-Y10 MG0.05 BMP10 TTNPB1 IGF250 | hESC Agg.: hESC aggregates; XF HA: DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin (all from Life Technologies), 10 ng/mL heregulin-1b (Peprotech) and 10 ng/mL Activin A (R&D Systems); SP: StemPro® hESC SFM (Life Technologies); r0.2FBS: RPMI 1640 (Mediatech); 0.2% FBS (HyClone), 1x GlutaMAX-1 (Life Technologies), 1% v/v penicillin/streptomycin; cb: CMRL: CMRL 1066, 1x Glutamax, 1% v/v penicillin/streptomycin, 2% B-27; db: DMEM Hi Glucose (HyClone) supplemented with 0.5xB-27 Supplement (Life Technologies), 1x GlutaMAX, and 1% v/v penicillin/streptomycin; A100, A50, A5: 100 ng/mL, 50 ng/mL, 5 ng/mL recombinant human Activin A (R&D Systems); BMP20, BMP10: 20 ng/mL, 10 ng/mL BMP4 (Peprotech); CTT3: 0.25 mM KAAD-Cyclopamine (Toronto Research Chemicals) and 3 nM TTNPB (Sigma-Aldrich); E50: 50 ng/mL recombinant human EGF (R&D Systems); H10, H5: 10 ng/mL, 5 ng/mL Heregulin 1b; IGF25: 25 ng/mL Insulin-like Growth Factor (Peprotech); ITS: Insulin-Transferrin-Selenium (Life Technologies) diluted 1:5000 or 1:1000; IV: 2.5 mM TGF-b RI Kinase inhibitor IV (EMD Bioscience); K50, K25: 50 ng/mL, 25 ng/mL recombinant human KGF (R&D Systems, or Peprotech); MG0.05: 0.05% MATRIGEL (BD Biosciences); N50: 50 ng/mL recombinant human Noggin (R&D Systems); NC10: 10 mM Nicotinamide; PDGF10: 10 ng/mL Platelet-derived growth factor (PDGF, R&D Systems); R01: gamma-secretase inhibitor, R04929097, 1 mM; SHH100: 100 ng/mL sonic hedgehog; TTNPB1: 1 nM TTNPB (Sigma-Aldrich); W50: 50 ng/mL recombinant mouse Wnt3A (R&D Systems); Y10: 10 mM Y-27632 (Tocris Bioscience).

After four days cryopreservation, the PEC aggregates (which were incubated in the cryopreservation solution for 30 or 60 minutes) were thawed and analyzed for cell survival. Percentage of cell survival was quantitated by measuring cell pellet volume (μL) or calculating the area covered by cell aggregates in tissue culture plates, e.g. 6-well tissue culture plates.

Measurements were taken at two time points, the first time point, at thaw, before any significant cell loss occurs (i.e. 100% cell survival); and the second time point, 1 day (or 24 hours) post-thaw after which the majority of cell loss has occurred. The percentage of cell survival at 1 day (24 hours) post-thaw was calculated by comparing time point 1 to time point 2 Table 6 below summarizes the percentage cell survival for two samples at 30 and 60 minutes.

TABLE 6

Percent Cell Survival Following Extended Incubation in Cryopreservation Solution and Cryopreservation

| Sample Equilibration Time (min) | Percent Survival 24 hrs Post-Thaw | |
|---|---|---|
| | Replicate 1 | Replicate 2 |
| 30 | 28% | 25% |
| 60 | 38% | 33% |

The morphology of cultured PEC aggregates (which were incubated in the cryopreservation solution for 30 or 60 minutes) after cryopreservation and thawing was identical to that of fresh cells. The results in Table 6 above indicate that cell survival following prolonged incubation in cryopreservation solution results in better cell survival (60 min equilibration time, 38% and 33% (avg. 35%) vs. 30 min, 28% and 25% (avg. 26%)). This result is surprising because it was previously thought that DMSO or other cryopreservative treatments for extended periods of time decreased cell survival and/or function after thawing. Thus, it was unexpected that PEC would survive well after 30 or even 60 minutes of DMSO treatment.

In another study, prolonged incubation of PEC in the cryopreservation solution was further optimized. At day 12 of differentiation as substantially described in Schulz et al. (2012) supra, the PEC aggregates were centrifuged and then resuspended in cryopreservation solution containing DMEM with 30% Xeno-free Knockout Serum Replacement, 25 mM HEPES and 10% DMSO solution. Cells were aliquoted into freezing vials and equilibrated in cryopreservation solution for about 15 minutes at ambient temperature, for 45 minutes at 4° C., then placed on ice and put in a programmed freezer at 0° C. Incubation at 4° C. is known to lessen toxicity associated with cryoprotective agents but also slows the rate of diffusion of the cryopreservation solution into the cells.

The freezing chamber containing the cells was brought to −9° C. at a rate of 2° C./min. The chamber was held at this temperature for about 10 minutes, and the vials were seeded manually (formation of ice crystals). The sample was held at −9° C. for about 10 minutes and then cooled at a rate of 0.2° C./minute until the vials reached −40° C. The freezing chamber was subsequently cooled at a rate of 25° C./minute until the vials reached about −150° C. The vialed cells were then moved to the vapor phase of a liquid nitrogen storage freezer.

At desired times, the vials were rapidly thawed by transferring the vials to a 37° C. water bath. The cells were transferred to a 15 mL sterile tube, containing DMEM with B-27 (1:100) mixed gently and spun briefly at 50xg. Supernatant was removed and cells were resuspended in the same buffer plus Noggin, KGF+EGF (each at 50 ng/mL), and DNAse at 25 µg/mL (incubation medium) and placed in rotation culture for 3 or 4 days PEC aggregates (Stage 4—Day 12) samples were either (1) immediately analyzed (PEC no cryo), (2) incubated for 3 days without cryopreservation in the above described incubation medium (PEC, 3 day incubation, no cryo) or cryopreserved, thawed and incubated for 3 or 4 days in the above described incubation medium (PEC, 3/4 day incubation after cryo). Cell composition of PEC cultures was analyzed using flow cytometry as shown in Table 7 below: Column A represents CHGA(+)(Endocrine cells); Column B represents CHGA−, NKX6-1+, PDX1+ (non-endocrine cells) and Column C represents CHGA− cells which are a) PDX1+ and NKX6.1− b) PDX1− and NKX6.1+ or c) PDX1− and NKX6.1− (residual cells).

The above data also indicates that the incubation period (whether cryopreserved or not) increases the total percentage of endocrine cells plus non-endocrine cells increases whereas the "residual" cells decrease. The above results are surprising because previously it has been shown that cryopreservation of hESCs causes extensive cell death, and a proportion of those that survive differentiate spontaneously. See Reubinoff et al. (Human Reproduction, 2001, 16, 2187-2194. Thus, increased cell survival of PEC without substantially changing the overall cellular composition or population is an important feature of the above protocol.

It will be appreciated that the methods and compositions described above relate to cells cultured in vitro. However, the above-described in vitro differentiated cell compositions may be used for in vivo applications. Use of the compositions described herein have been described detail in at least

TABLE 7

Flow Cytometry Analysis of Cryopreserved and Non-Cryopreserved PEC

| PEC Treatment | PEC | | |
|---|---|---|---|
| | CHGA+ (Endocrine) | CHGA−, NKX6.1+, PDX1+ (Non-endocrine) | CHGA− NKX6.1+/− PDX1+/− (Residual Cells) |
| No cryo (n = 8) | 50 | 27 | 23 |
| No cryo, 3 days incubation (n = 1) | 57 | 33 | 10 |
| 3 days incubation after cryopreservation and thaw (n = 6) | 43 | 50 | 7 |
| 4 days incubation after cryopreservation and thaw (n = 7) | 40 | 51 | 9 |
| >4 days incubation after cryopreservation and thaw (n = 2) | 42 | 50 | 8 |

According to Table 7, results of the flow cytometry show that the populations of cells before and after cryopreservation are similar, i.e., a substantial proportion of both the cryopreserved and non-cryopreserved population consists of CHGA+ (endocrine cells) and CHGA−/NKX6-1+/PDX1+ (non-endocrine). Thus, cryopreservation of PEC cultures does not compromise the overall cell population (since the percentages of CHGA+/NKX6-1−/PDX1− (endocrine cells) and CHGA−/NKX6-1+/PDX1+ (non-endocrine cells) are similar. Survival of the endocrine and non-endocrine cell populations is an important feature of the above protocol.

While the cell compositions are similar overall for cryopreserved and non-cryopreserved samples, according to Table 7, there are some small changes in the overall cell composition. For example, cryopreservation increases the percentage of non-endocrine cells as compared to endocrine cells. Specifically, in Table 7, 57% of CHGA+ and 33% CHGA−/NKX6-1+/PDX1+ in stage 4, no cryo, 3 day incubation sample versus 43% CHGA+ and 50% CHGA−/NKX6-1+/PDX1+ in the stage 4, cryopreserved, 3 day incubation sample. This increase in CHGA−/NKX6-1+/PDX1+ (non-endocrine cells) as compared to CHGA+ (endocrine cells) is also seen in those cultures which had longer post-thaw incubation periods, e.g. cryopreserved, 4 day incubation post-thaw. An increase in the non-endocrine as compared to endocrine cells is an important feature of the above protocol.

Additionally, it is noted that the cell aggregates are large compared to single cells and may leave a large liquid headspace upon cryopreservation in vials. Cell yield may increase post thaw if this head space is reduced by using smaller vials or cryopreserving the tubes in a horizontal vs vertical orientation.

Applicant's U.S. Pat. Nos. 7,534,608; 7,695,965; and 7,993,920; entitled METHODS FOR PRODUCING PANCREATIC HORMONES, which issued May 19, 2009, Apr. 13, 2010 and Aug. 9, 2011, respectively; and U.S. Pat. No. 8,278,106, entitled ENCAPSULATION OF PANCREATIC CELLS DERIVED FROM PLURIPOTENT STEM CELLS. Use and function of the compositions described herein have also been reported by Applicant in prior non-patent publications including Kroon et al. 2008 supra and Schulz et al. 2012, supra.

Example 2

Cryopreserving and Thawing Encapsulation Devices

To determine whether implantable semi-permeable encapsulation devices as described herein can maintain their integrity, devices were cryopreserved, thawed and subsequently tested for quality assurance as described below.

It will be appreciated that cryopreservation of encapsulation devices can be carried out using different techniques and equipment including but not limited to in liquid nitrogen (−196° C.), in liquid nitrogen vapor phase, in a cryogenic freezer, or via a slow rate freezing or vitrification.

Five empty single ported encapsulation devices with no internal weld(s) were sterilized with ethylene oxide gas and the port trimmed to approximately 1 cm see FIGS. 1A and 1B. The empty encapsulation devices were then placed in 10 mL cryotubes (VWR Product # SIMPT 310-10A) with the port facing the lid or cap. Approximately 5.5 mL of cryopreservation solution (stock solution comprised of 13.75 mL DMEM, 5.0 mL DMSO, 30.0 mL Xeno-free Knockout Serum Replacement and 1.25 mL HEPES for a total volume of 50 mL) was added to the cryotube to cover the device and port. The cryotube with the empty encapsulation device was then centrifuged at 1500 rpm for about 3 minutes to remove any residual air from the lumen and port inside the device.

Because the tubes holding the encapsulation device did not fit into the controlled rate freezer, the cryotubes were placed in a test tube rack fashioned from foam material. Each tube was fully covered by the foam material and then placed in −80° C. freezer overnight. This system mimics a controlled rate freezer because the insulation provided by the foam slows the freezing rate as air trapped in the foam slows heat transfer. Controlled freezing can also be achieved using a Mr. Frosty (NALGENE) vessel. The cryotubes were then removed from the −80° C. freezer and transferred to the vapor phase compartment of a liquid nitrogen tank in order to bring the temperature lower. One of skill in the art will recognize that the frozen cryotubes can be stored in liquid nitrogen (−196° C.), liquid nitrogen vapor, or in a cryogenic freezer (−150° C.). After at least 24 hours of storage, devices were retrieved from the liquid nitrogen tank and rapidly thawed in 37° C. water bath for approximately 2 minutes. The devices were then transferred to 50 mL conical tubes with 50 mL of PBS (phosphate buffered saline) to wash off the cryopreservation solution. After approximately 15 minutes the PBS was decanted off and replaced with fresh 50 mL PBS.

In order to be useful for cryopreserving the encapsulated cells (or cell-device combination product), the device needs to maintain its integrity. To determine whether the cryopreserved devices maintained their integrity, pressure decay and burst pressure testing was performed. Pressure decay is tested by submerging the device in 100% isopropyl alcohol to saturate the pores of the membrane. The device is then connected to a Sprint iQ Leak Tester (USON) that fills the device with clean air until the target pressure (about 5 psi+/−0.1 psi) is reached. Once pressurized, the flow of air stops, the device sealed and the amount of pressure loss over 20 seconds is recorded. A cryopreserved device passes the pressure decay test if the amount of pressure loss over 20 seconds is ≤0.010 psi. If the integrity of the device was compromised by cryopreservation, the pressure decay would be higher than 0.010 psi. Burst pressure is tested by connecting the device to the Sprint iQ Leak Tester which generates a pressure ramp of approximately 1 psi/sec. A cryopreserved device passes the burst pressure test if the device can withstand ≥5 psi without bursting. A target pressure of 5 psi is used for the burst pressure and pressure decay tests because it is estimated that cells grown in the device for 6 months have a pressure of 2.5 psi. Hence, by testing for 5 psi, there is a 2.5 safety threshold; and measuring 5 psi allows detection of holes in the device down in the 1-3 μM range. Ensuring the devices can withstand 5 psi without bursting ensures the devices will be intact. Later detection of device integrity (or device expansion) can be imaged in vivo with standard clinical ultrasound for example.

Table 8 shows the leak test results of 10 devices tested substantially as described above.

TABLE 8

Integrity of Cell Encapsulation Devices: Cryopreserved vs. Non-Cryopreserved

| Sample No. | Status | Pressure Decay (PSI) | Pressure Decay Pass/Fail | Burst Pressure (PSI) | Burst Pressure Pass/Fail |
|---|---|---|---|---|---|
| 1 | Cryopreserved | 0.001 | Pass | 18.84 | Pass |
| 2 | Cryopreserved | 0.000 | Pass | 21.29 | Pass |
| 3 | Cryopreserved | 0.001 | Pass | 21.20 | Pass |
| 4 | Cryopreserved | 0.001 | Pass | 20.35 | Pass |
| 5 | Cryopreserved | 0.000 | Pass | 17.46 | Pass |
| 6 | Non-Cryopreserved | 0.001 | Pass | 18.894 | Pass |
| 7 | Non-Cryopreserved | −0.001 | Pass | 22.612 | Pass |
| 8 | Non-Cryopreserved | 0 | Pass | 21.033 | Pass |
| 9 | Non-Cryopreserved | 0.001 | Pass | 22.156 | Pass |
| 10 | Non-Cryopreserved | −0.001 | Pass | 21.046 | Pass |

As indicated above in Table 8, the encapsulation devices after cryopreservation had an average burse pressure of 19.28 psi. The non-cryopreserved encapsulation devices had an average burse pressure of 21.15 psi. While the non-cryopreserved encapsulation devices had a higher average burse pressure, both cryopreserved and non-cryopreserved encapsulation devices had burst pressures much greater than what is expected for cell expansion in vivo (2.5 psi). The pressure decay and burst pressure of cryopreserved devices was comparable to devices which had not been cryopreserved. The results of both the pressure decay and burst testing demonstrate that, short term cryopreservation as described herein does not compromise the general integrity of the devices. Specifically, DMSO exposure during freeze and thaw did not impact device membrane integrity or weld burst strength. Additionally, rapid thawing from vapor phase Liquid nitrogen temps (−135 C to −190 C) did not stress the device weld or materials to cause rupture or measurable change in its integrity.

It will be appreciated by those of skill in the art that after the devices are thawed, cells may be loaded into the cryopreserved device and surgically implanted in a mammalian host. PEC aggregates loaded into a previously cryopreserved device are capable of post-engraftment function in vivo, as defined by long-term glucose-responsive human C-peptide secretion or protection against STZ-induced hyperglycemia. Hence, cryopreservation of empty implantable, semipermeable devices is expected to have little or no effect on, cell survival upon implantation, maturation of the cells or the physiological function of the cells once they have matured. Thus, cryopreservation proves to be a reliable method of storing empty implantable, semipermeable devices.

Example 3

Cryopreserved PEC Mature and Function In Vivo

To determine whether cryopreservation of PEC aggregates affects in vivo function, PEC cell aggregates that had been previously cryopreserved and the thawed were loaded into an implantable, semipermeable, cell-encapsulation device, transplanted, allowed to mature and levels of human c-peptide in sera of implanted mice measured following intraperitoneal glucose administration. One of skill in the art will recognize that any appropriate implantable, semipermeable encapsulation device can work for this study as described herein and FIGS. 1A-1I, 2A-2B, 3A-3B, 4A-4B and 5A-5C, and in Applicant's other patent and non-patent publications, including Schulz et al. (2012) and Kroon et al (2008), supra and U.S. Pat. Nos. 7,534,608; 7,695,965; 7,993,920 and 8,278,106, supra.

PEC aggregates cryopreserved for about 1 hour, 4 days, 6 weeks (data combined since no differences were observed for these time periods) or 2 years were transplanted into mice substantially as previously described herein and in Applicant's other patent and non-patent publications, including Schulz et al. (2012) and Kroon et al (2008), supra and U.S. Pat. Nos. 7,534,608; 7,695,965; 7,993,920 and 8,278,106, supra. Briefly, PEC populations were wholly encapsulated with a biodegradable semi-permeable cell encapsulation device. The devices were manufactured by Applicant and are described in detail in U.S. Pat. No. 8,278,106, entitled ENCAPSULATION OF PANCREATIC CELLS FROM HUMAN PLURIPOTENT STEM CELLS, filed Nov. 13, 2009. Glucose stimulated insulin secretion (GSIS) assays were performed starting from about 8-9 weeks and 11-13 weeks post-implant. Blood was collected prior to (fasting) and at 60 minutes after glucose administration. Graft function was assessed by measuring human C-peptide concentrations in the serum in response to glucose administration.

The amount of human C-peptide released into the serum is indicative of the amount of insulin released. C-peptide is a short 31 amino acid peptide connecting or linking A and B-chains of proinsulin and preproinsulin, which is secreted by functioning beta or insulin secreting cells. As discussed previously by Kroon et al. (2008) supra and others, human C-peptide measurements are appropriate for assessing the release of de novo-generated insulin by the implanted cells. Hence, levels of human C-peptide in the serum of these animals is a measure of the in vivo function of the mature PEC grafts. Human C-peptide was detected in the serum by 8-9 weeks post-implant.

Figure 7:
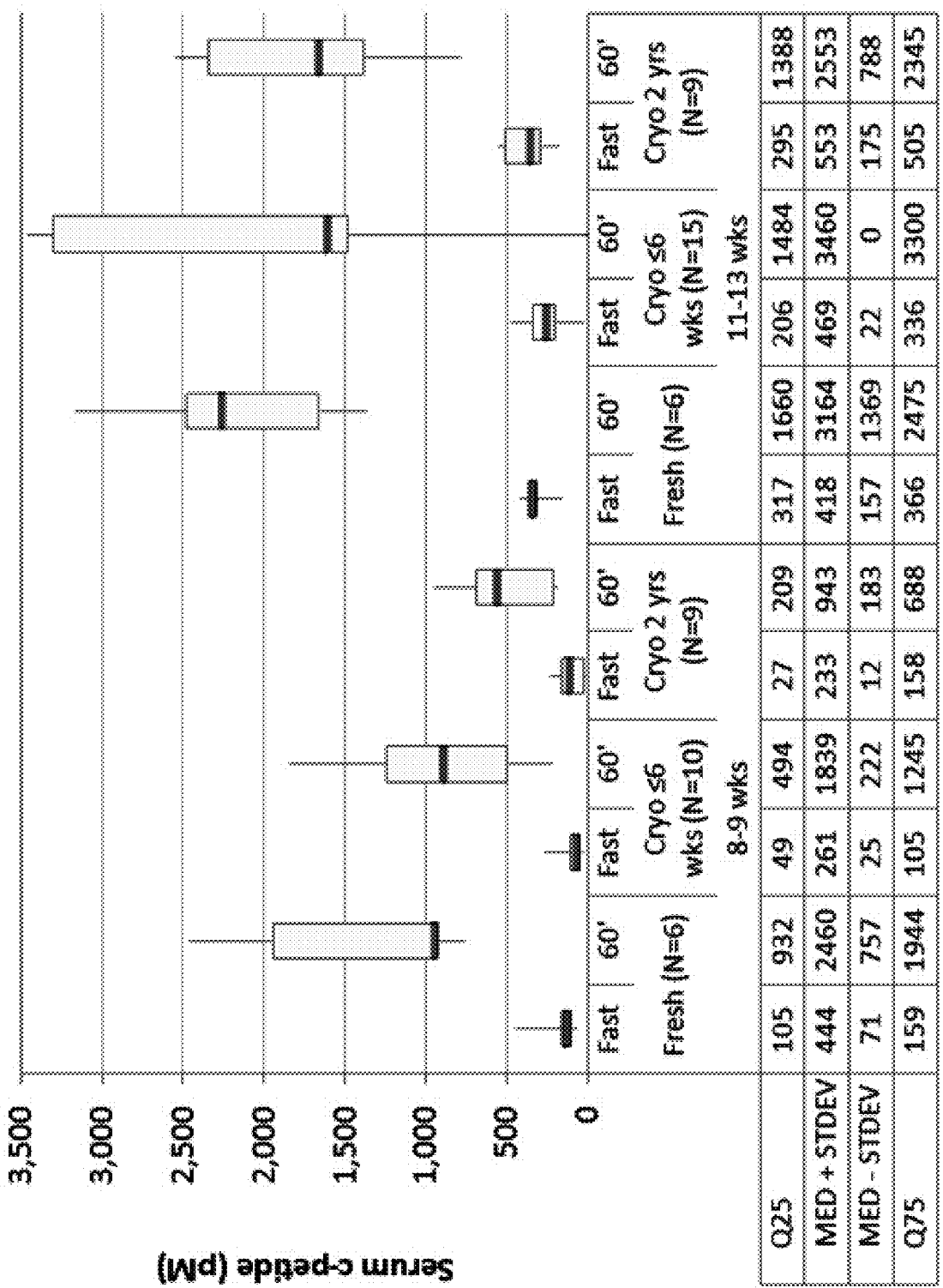
FIG. 7 is a graph showing concentration of human c-peptide in sera of mice implanted with a cell-device combination product. Expression levels were analyzed at 8-9 weeks or 11-12 weeks post-engraftment at fasting and 60 min after 3 g/kg intraperitoneal glucose administration. N identifies the total numbers of GSIS (glucose stimulated insulin secretion) tests performed on mice within the indicated post-implant intervals. The box identifies the middle 50% of the values, the median is represented by the horizontal line within the box and the standard deviations are represented by the vertical lines extending from the box.

FIG. 7 is a box plot showing levels of human C-peptide in sera of implanted mice. Mice implanted with the cell-device combination product (PEC loaded in an implantable semipermeable cell encapsulation device) were analyzed at 8-9 weeks or 11-13 weeks post-engraftment for serum levels of human C-peptide at fasting and 60 min after intraperitoneal glucose administration. The encapsulation device was loaded with fresh (not cryopreserved) or cryopreserved PEC aggregates. The cryopreserved PEC aggregates were either cryopreserved for 6 weeks or less or for 2 years. N identifies the total numbers of GSIS (glucose stimulated insulin secretion) tests performed on mice within the indicated post-implant intervals. At 8-9 weeks and 11-13 weeks the cryopreserved PEC for ≤6 weeks and 2 years had largely overlapping levels of serum human C-peptide at 60 minutes following glucose administration compared to fresh PEC samples. At 8-9 weeks the PEC samples cryopreserved for 2 years had slightly lower serum C-peptide levels as compared to the fresh PEC and those PEC cryopreserved for ≤6 weeks but the values are still overlapping. At 11-13 weeks the serum C-peptide levels are overlapping for all three PEC samples (fresh, ≤6 weeks and 2 years cryopreservation). Additionally, graft function improves with time in both the PEC cryopreserved for ≤6 week cryopreservation and 2 years cryopreservation and non-cryopreserved PEC samples, e.g., serum C-peptide levels are higher than at 11-12 weeks compared to 8-9 weeks. As such, mature PEC grafts made from cryopreserved PEC loaded into an encapsulation device are as robust as fresh PEC grafts; and cryopreservation did not reduce the capacity of the PEC aggregates to mature and function in vivo, i.e., long-term glucose-responsive human C-peptide secretion. Thus, cryopreservation of PEC aggregates prior to implantation in an implantable semipermeable cell-encapsulation device proves to be a reliable method of storing PEC aggregates.

Figure 8:
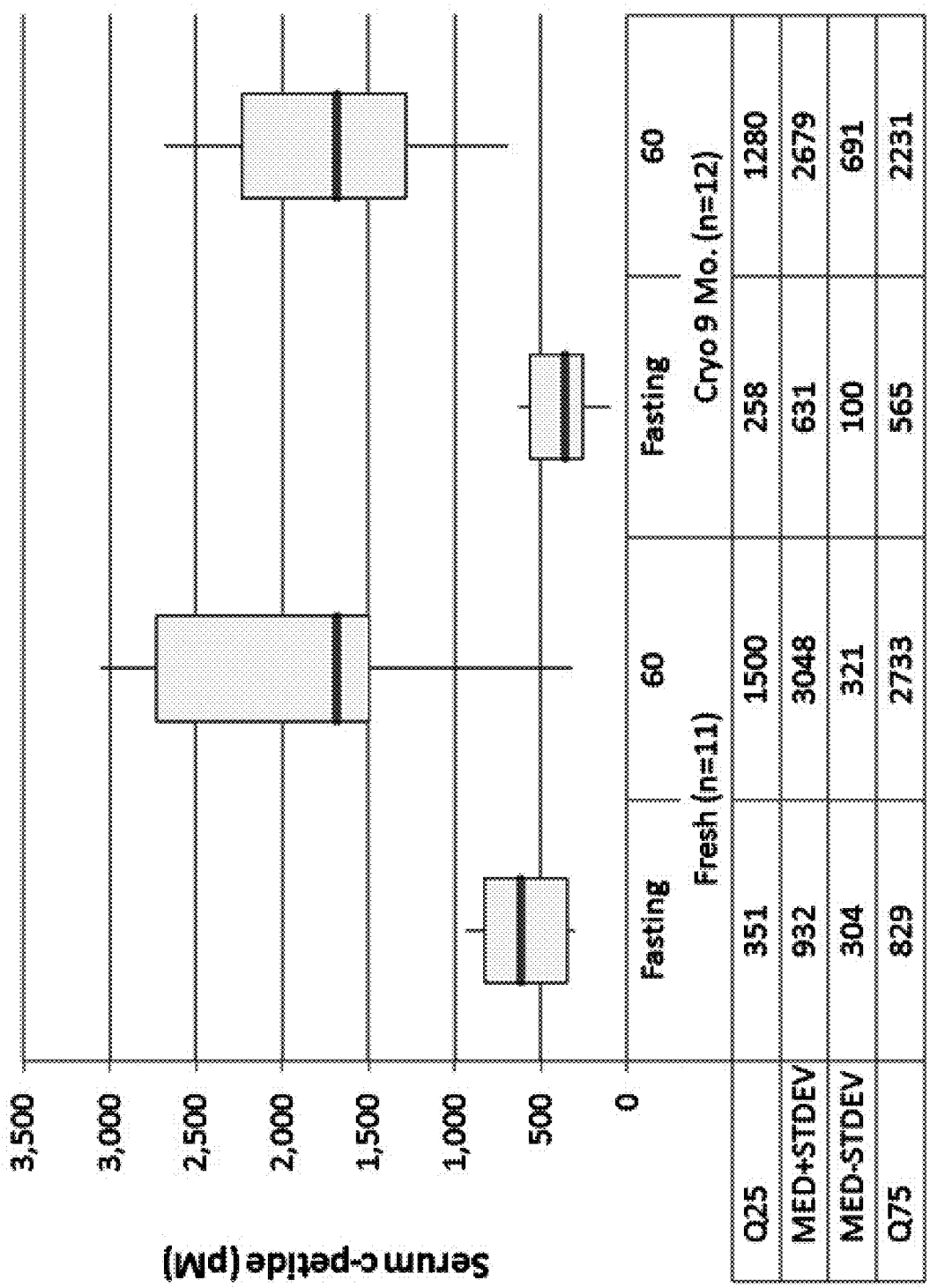
FIG. 8 is a graph showing concentration of human c-peptide in sera of mice implanted with un-encapsulated PEC aggregates (no device) in the epididymal fat pad. Expression levels were analyzed 12 weeks post-engraftment at fasting and 60 min after 3 g/kg intraperitoneal glucose administration. N identifies the total numbers of GSIS (glucose stimulated insulin secretion) tests performed on mice within the indicated post-implant intervals. The box identifies the middle 50% of the values, the median is represented by the horizontal line within the box and the standard deviations are represented by the vertical lines extending from the box.
Figure 9:
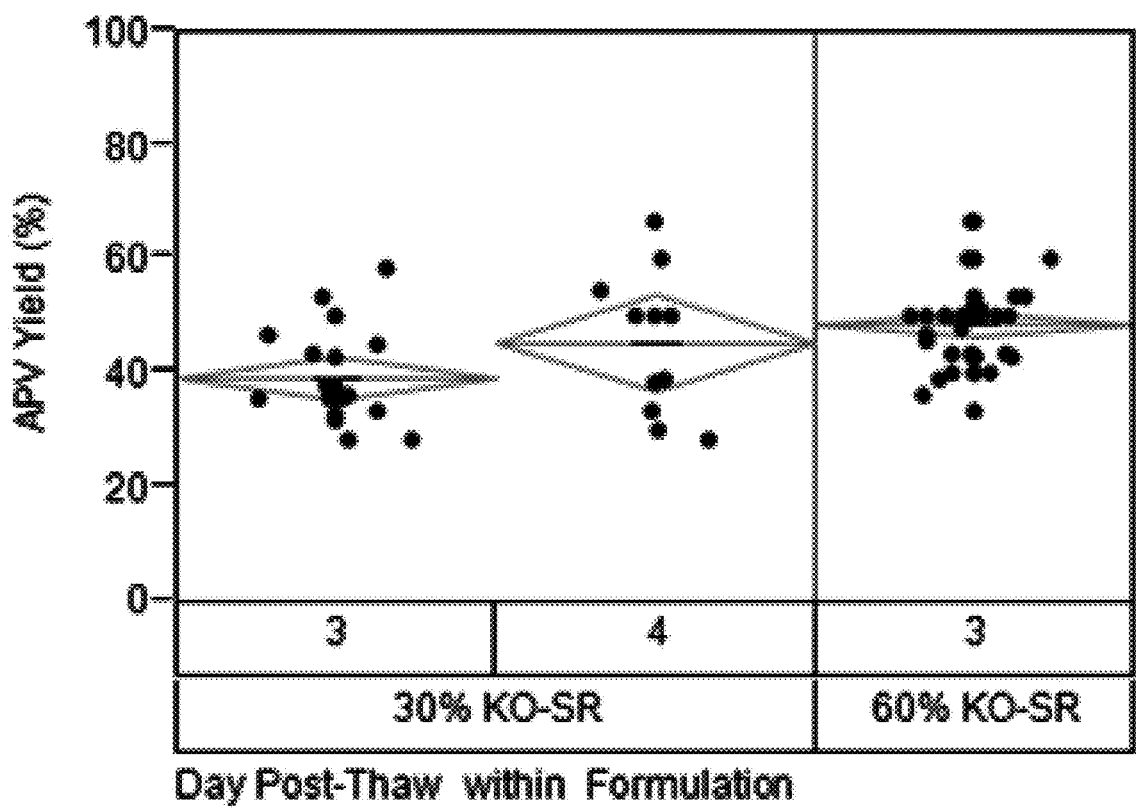
FIG. 9 is a graph showing the aggregate pellet volume (APV) yield for cryopreserved PEC aggregates in 30% or 60% KnockOut Serum Replacement 3 or 4 days post thaw. The X-axis shows the percentage of knockout serum used to culture the post thawed cells. The Y axis shows the aggregate pellet volume (APV) yield, i.e., the percentage of the output (pellet volume 3 or 4 days post thaw) over the input (pellet volume immediately post thaw). The 90% confidence window is represented by the line in the middle of the diamond and the lines forming the diamond.
Figure 10:
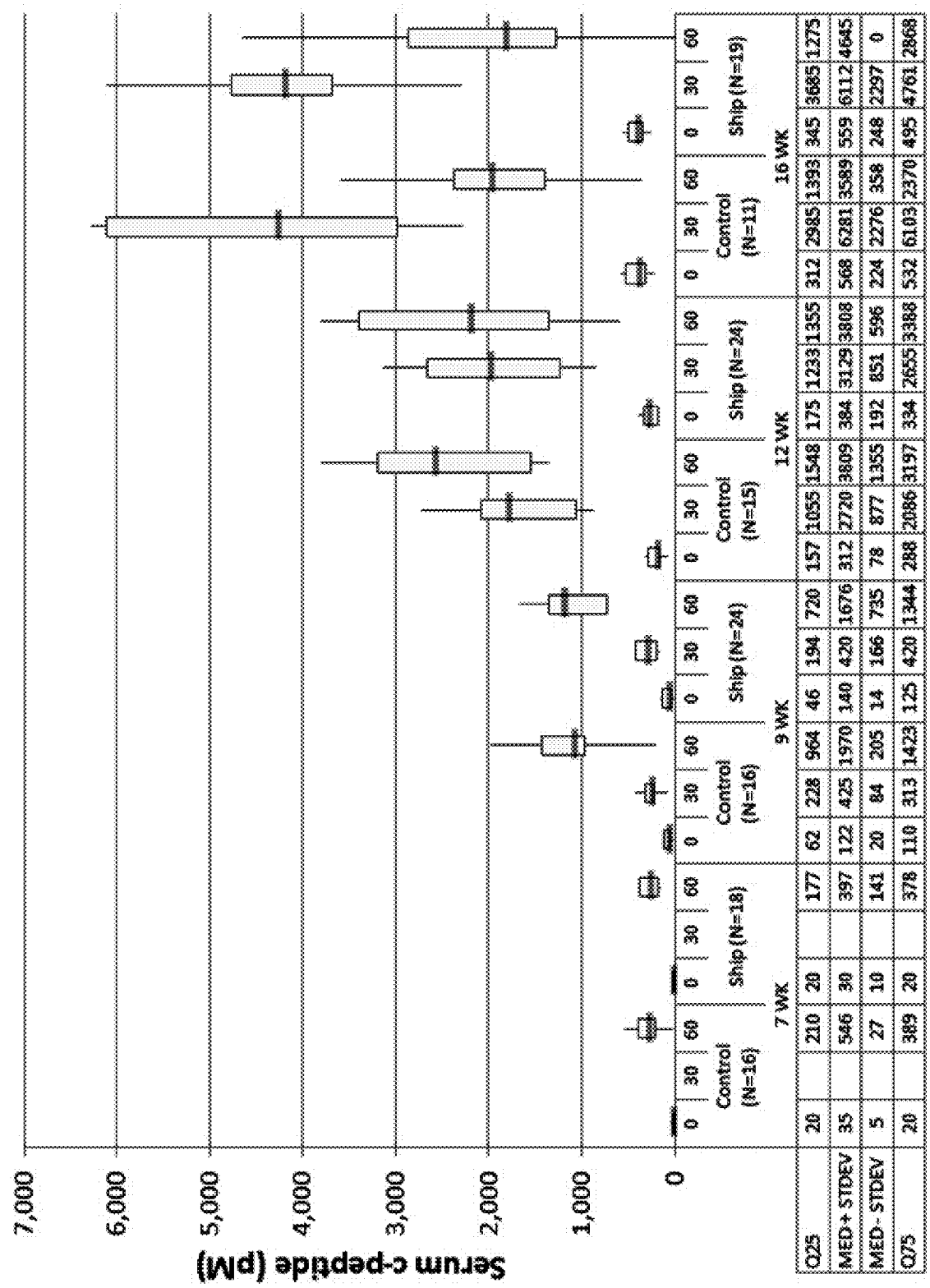
FIG. 10 is a graph showing concentration of human c-peptide in sera of mice implanted with a VC combination product. Expression levels were analyzed 9, 12, 16 and 24 weeks post-engraftment (data combined) at fasting, 30 min, and 60 min after intraperitoneal glucose administration. The controls are cell-device combination products loaded with day 4 post thawed cells and implanted the same day. Shipped samples are cell-device combination products loaded like the controls but then shipped to an off-site location (Sunnyvale), returned to San Diego, and implanted 24 hours later than the non-shipped controls.

To determine what affect the device had on PEC in vivo function, Applicants compared the in vivo function of unencapsulated cryopreserved PEC vs. encapsulated non-cryopreserved (or Fresh) PEC. FIG. 8 is a box plot showing levels of human C-peptide in sera of implanted mice. Mice implanted with un-encapsulated PEC aggregates (no device) in the epididymal fat pad were analyzed 12 weeks post-engraftment for serum levels of human C-peptide at fasting and 60 min after intraperitoneal glucose administration. Devices were loaded with fresh PEC (not cryopreserved) or 9 month cryopreserved PEC aggregates. N identifies the total numbers of GSIS (glucose stimulated insulin secretion) tests performed on mice within the indicated post-implant intervals. As such, mature grafts from un-encapsulated cryopreserved PEC implanted in the epididymal fat pad was as robust as fresh unencapsulated PEC grafts; and cryopreservation did not reduce the capacity of the PEC aggregates to mature and function in vivo. Thus, cryopreservation of PEC aggregates prior to implantation in the epididymal fat pad proves to be a reliable method of storing PEC aggregates.

The above results are surprising because previously it has been shown that cryopreservation of human embryonic stem cells causes extensive cell death, and a proportion of those that survive differentiate spontaneously. One would expect a similar outcome for PEC. Thus, the survival, ability for the cells to mature in vivo and demonstrate substantial post-engraftment function in vivo demonstrates that PEC is well suited for cryopreservation methods.

Example 4

Cell Survival Following Incubation with 30% Vs. 60% Knockout Serum Replacement (KO-SR)

As discussed above, Applicant explored various cryopreservation conditions to optimize cell survival following cryopreservation. Applicant also explored various thawing and incubation conditions to optimize cell survival following cryopreservation. Thawing and incubation conditions analyzed include, but are not limited to optimization of the concentrations, time of use and duration of the thawing and incubation media, and treatment with other factors in the thawing and incubation media for improving cell survival. These many iterative experiments were tested alone, or in combination, to determine how cell survival following cryopreservation could be optimized. Such optimized thawing and incubation protocols produce PEC aggregates with optimized cell survival following cryopreservation.

As a specific example, PEC aggregate populations were produced and cryopreserved substantially as described in Example 1 above. Cryopreserved PEC aggregates were then thawed and cultured for 3 or 4 days on either 30% or 60% knockout serum replacement. Cell viability in Example 1 was described by calculating the percentage of cell aggregates at two time points in a cell culture dish. Here, cell viability was measured using a similar measurement except using aggregate pellet volume (APV or cell mass). The APV yield is the APV post thaw divided by the APV immediately after thaw in different levels of KO-SR, which is used to affect cell survival. Standard thaw conditions were used to thaw cryopreserved PEC plus 30% KOSR for 3 days post thaw, 30% KOSR for 4 days post thaw and 60% KO-SR for 3 days post thaw. Table 9 shows the APV yields of this study. Because the mean APV yields overlap (when considering the standard deviation), there is no statistical difference in APV yield when aggregates were cultured post thaw in 30% or 60% KO-SR. See also FIG. 9.

TABLE 9

| Variability Summary for APV Yield (%) | | | | | |
|---|---|---|---|---|---|
| | Mean | Std Dev | Lower 95% | Upper 95% | Number of Thawed Samples Tested |
| APV Yield (%) [all samples 30% and 60%] | 45.77496 | 9.051004 | 43.72064 | 47.82929 | 77 |
| APV Yield Formulation [30% KO-SR] | 41.48125 | 10.12904 | 37.76589 | 45.19661 | 31 |
| APV Yield Formulation [60% KO-SR] | 48.66855 | 6.978349 | 46.59624 | 50.74087 | 46 |
| APV Yield Formulation [30% KO-SR] Day Post-Thaw[3] | 39.29089 | 8.056655 | 35.52026 | 43.06152 | 20 |
| APV Yield Formulation [30% KO-SR] Day Post-Thaw[4] | 45.46373 | 12.54681 | 37.03466 | 53.89279 | 11 |
| APV Yield Formulation [60% KO-SR] Day Post-Thaw[3] | 48.66855 | 6.978349 | 46.59624 | 50.74087 | 46 |

Example 5

Shipping Cell Loaded Encapsulation Devices

To determine the viability of the cell-device combination product, the product was shipped and assayed as described below.

Implantable semi-permeable devices were loaded with PEC aggregates substantially as described above. The loaded devices were then packed into a biological shipping container surrounded by gel packs to keep the cells at about 37° C. The container was shipped using a private courier and transported approximately 400 miles. The shipment was unloaded at the destination center, stored at room temperature overnight and then returned again using gel packs to maintain constant room temperature. In total, the shipment was in transit for approximately 24 hours.

Cells shipped approximately 400 miles at 37° C., stored at room temperature overnight, returned approximately 400 miles at room temperature to San Diego and implanted had comparable serum human C-peptide levels 9, 12, 16 and 24 weeks post-transplant (data combined) as compared to implantable semi-permeable devices loaded with day 4 post thaw cells and implanted at 4 days post-thaw. See FIG. 10.

One of skill in the art recognizes that this protocol represents a standard protocol which could be used to ship kits consisting of product cells, product devices, alone or in combination to the clinical site, e.g. doctor's office, hospital, and the like. Additionally, one of skill in the art will recognize that on site locations such as doctor's offices typically have 4° C. cold storage units. Cells are expected to mature and function (glucose-responsive human c-peptide secretion or protection against STZ-induced hyperglycemia) when encapsulated cells are shipped to facilities and stored at 4° C. in an organ/tissue preservation solution described below.

It is understood that the shipping protocol described above limit spontaneous differentiation and ideally promote survival of cell types of interest such as non-endocrine cells compared to endocrine and residual cell types.

Example 6

Extending Shelf Life of PEC Aggregates

While cryopreservation is a useful long term storage approach, there is a need for short-term storage at room temperature or refrigerator temperature (0° C.–8° C.) ("hibernation"). Therefore, Applicant evaluated the viability and yield of PEC following short-term storage at 4° C. or room temperature in three organ/tissue preservation solutions. Unlike, cryopreservation techniques which use intracellular cryopreservatives such as DMSO, these hibernation studies utilize tissue preservation solutions which reduced the need for substantial processing of the cell therapy product in order to remove the toxic cryoprotectants prior to administration to a patient. Specifically, these hibernation media compositions do not include DMSO.

PEC aggregate populations were produced and cryopreserved substantially as described in Example 1 above. Except, here, differentiation was carried out in a bioreactor substantially as described in U.S. Patent Publication no. 2012/0045830. After 3 days of recovery at 37° C. in rotation (about 95 rpm), all cell aggregates were collected in a 50 mL conical tube and allowed to settle. The supernatant was removed then the aggregates were washed once in 40 mL DPBS (Dulbecco's phosphate buffer solution)+0.2% BSA. With the aggregates evenly suspended, aliquots of 10 mL were transferred into 4×50 mL conical tubes. After the aggregates settled, the supernatant was removed and 24 mL of the various test/control solutions (organ/tissue preservation solution) was added to each of the tubes. The preservation solutions tested (defined as both room temperature preservation solutions and hibernation preservation solutions) include: DB—DMEM Hi Glucose (Gibco, 11960-044), 1% B27 Supplement (Gibco, 17504-044), 1% Penicillin/Streptomycin (Gibco, 15070-063) and 1% Glutamax (Gibco, 35050-061) or "DB", KPS-1—Kidney Perfusion Solution (Organ Recovery Systems, KPS-1, Lot PBR-0048-006) and 1% Penicillin/Streptomycin (Gibco, 15070-063) or "KPS", S3—Static Preservation Solution, no additives (Organ Recovery Systems, SPS-1, Lot PBR-0060-001) and 1% Penicillin/Streptomycin (Gibco, 15070-063) or "S3", and Unisol-I-Base—(Cell and Tissue Systems, Inc., Lot UHK092110) and 1% Penicillin/Streptomycin (Gibco, 15070-063) or "Unisol". Refer also to FIGS. 12A-12B and 13A-13B.

For each of the test/control solutions (organ/tissue preservation solution), 3 mL was added to each well in 2×6-well trays for a total of 12 wells. With the aggregates evenly distributed in the conical tubes, 2 mL of aggregate suspension was added to each well of the various 6-well trays containing the appropriate corresponding media for a total of 5 mL in each well. Within each group of medias, the number of aggregates per well was adjusted such that the aggregates were evenly distributed (based on visual assessment).

The aggregates were stored in the solutions at 4° C. and room temperature for a period of 2 weeks, with pictures taken at 3, 5, 7, 12 and 14 days, and Live/Dead staining done at 7 and 14 days. Live/Dead staining was performed using a Viability/Cytotoxicity Kit by Life Technologies, L3224. LDH-based cytotoxicity was assessed at 7 and 14 days. Lactate dehydrogenase is a soluble cytosolic enzyme that is released into the culture medium following loss of membrane integrity resulting from either apoptosis or necrosis. LDH activity, therefore, can be used as an indicator of cell membrane integrity and serves as a general means to assess cytotoxicity resulting from chemical compounds or environmental toxic factors. Here LDH-based cytotoxicity was tested using CytoTox 96 LDH Assay (Promega, G1780), and the results are shown in FIGS. 12A-12B and 13A-13B.

FIGS. 12A-12B and 13A-13B and Tables 10 and 11 show that in general cell viability in the various preservation solutions is higher when the aggregates are stored at 4° C. as compared to room temperature storage; Compare FIGS. 12A and 12B and FIGS. 13A and 13B. Moreover, cell viability at 4° C. is significantly greater in the preservation solutions compared to the DMEM+1% B27 (DB) control media, with no significant difference in viability between 7 and 14 days of storage at 4° C. See FIGS. 12B and 13B.

After 7 days at 4° C., cell aggregates in the control DMEM+1% B27 (DB) media exhibited greater than ~2-fold increase in cytotoxicity as compared to aggregates in the preservation solutions by LDH release. In contrast, cell aggregates in the preservation solutions at 4° C. exhibited ~3-fold less cytotoxicity after 7 days compared to the same storage solutions at room temperature.

Figure 12A:
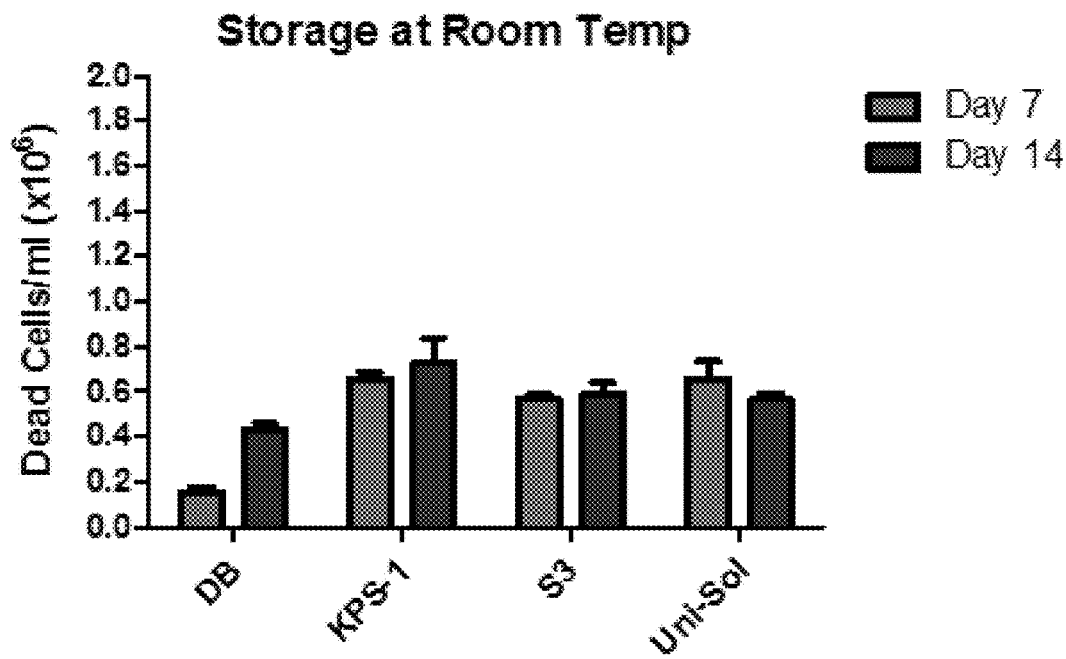
FIGS. 12A-12B are graphs showing the Lactate Dehydrogenase (LDH) Cytotoxicity results for PEC aggregates stored at room temperature (FIG. 12A) or 4 degrees Celsius (FIG. 12B) for 7 or 14 days and based on data shown in Table 10.
Figure 12B:
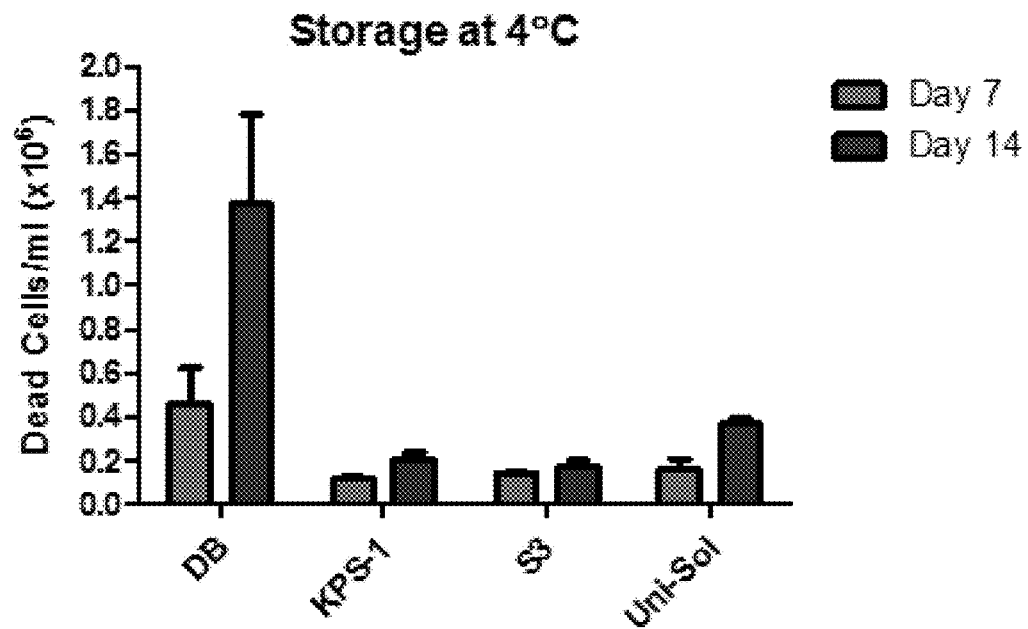
Figure 13A:
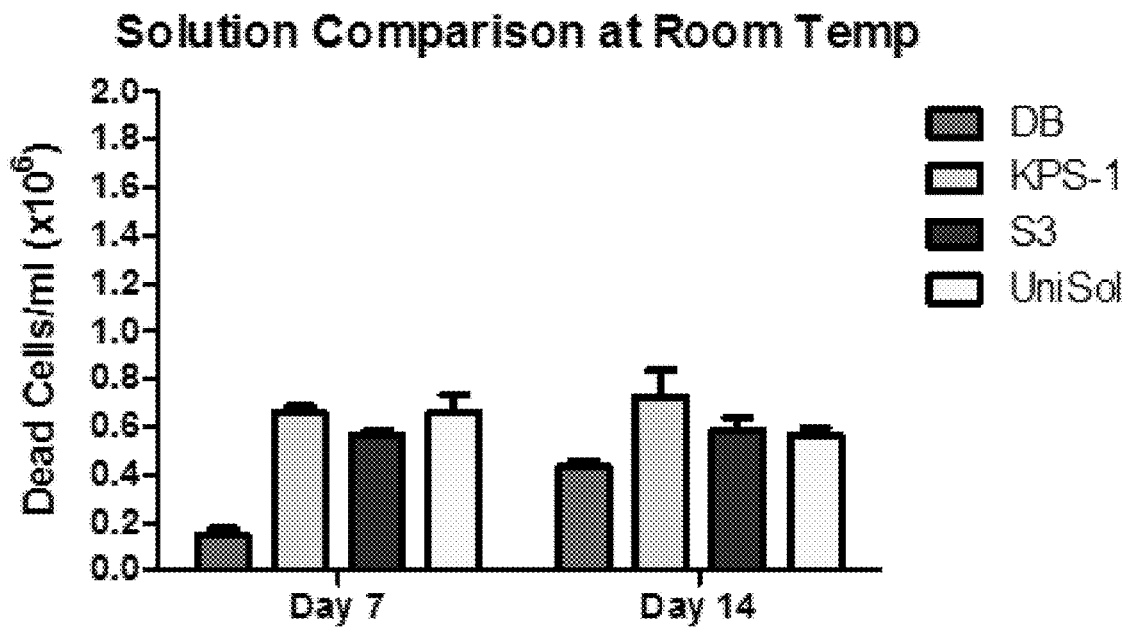
FIGS. 13A-13B are graphs showing the LDH Cytotoxicity results for PEC aggregates stored at room temperature (FIG. 13A) or 4 degrees Celsius (FIG. 13B) for 7 or 14 days and based on data shown in Table 10.
Figure 13B:
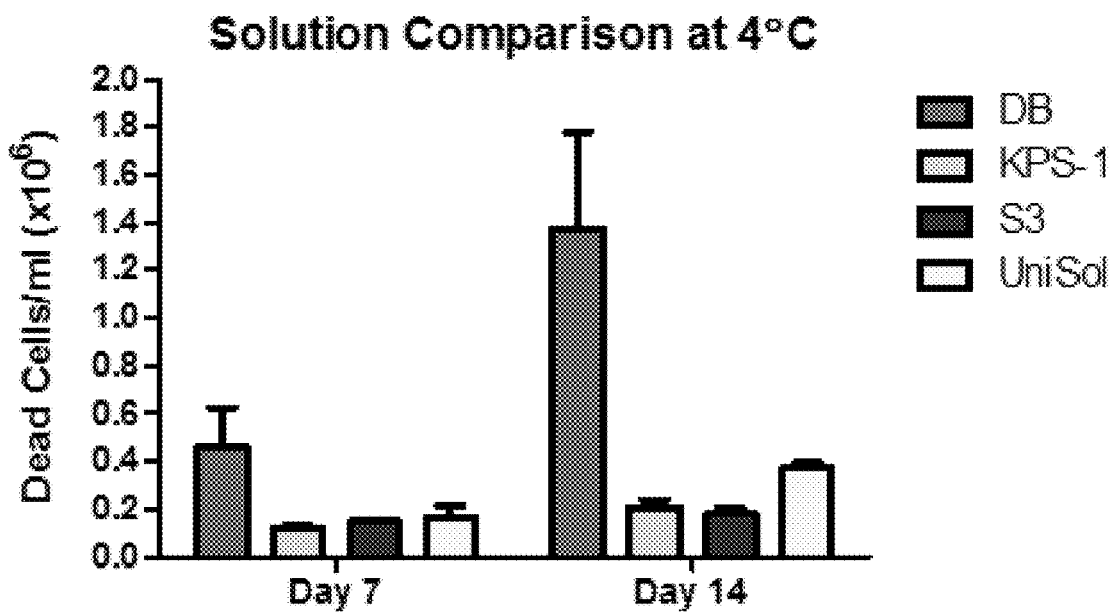

See FIGS. 12B and 13B.

TABLE 10

Raw Data For Cell Viability (Dead cells/mL ($\times 10^6$) at room temperature/ambient conditions

| | Sample 1 | | Sample 2 | | Sample 3 | |
|---|---|---|---|---|---|---|
| | Day 7 | Day 14 | Day 7 | Day 14 | Day 7 | Day 14 |
| DB | 0.139 | 0.417 | 0.182 | 0.463 | 0.134 | 0.421 |
| KPS-1 | 0.623 | 0.645 | 0.664 | 0.682 | 0.683 | 0.854 |
| S3 | 0.857 | 0.550 | 0.553 | 0.566 | 0.564 | 0.649 |
| Uni-Sol | 0.622 | 0.535 | 0.603 | 0.559 | 0.748 | 0.597 |

TABLE 11

Raw Data For Cell Viability (Dead cells/mL ($\times 10^6$) at 4° C. conditions:

| | Sample 1 | | Sample 2 | | Sample 3 | |
|---|---|---|---|---|---|---|
| | Day 7 | Day 14 | Day 7 | Day 14 | Day 7 | Day 14 |
| DB | 0.368 | 1.113 | 0.363 | 1.171 | 0.65 | 1.84 |
| KPS-1 | 0.112 | 0.187 | 0.127 | 0.195 | 0.123 | 0.246 |
| S3 | 0.152 | 0.161 | 0.151 | 0.168 | 0.138 | 0.207 |
| Uni-Sol | 0.144 | 0.383 | 0.22 | 0.349 | 0.134 | 0.384 |

To determine whether there was a real statistical significance between the results shown in Tables 10 and 11 and graphed in FIGS. 12A-12B and 13A-13B, analysis of variance (ANOVA) was used to test for significant differences between two or more means. ANOVA on the full factorial experimental design indicates that the media type, storage temperature and storage time are all statistically significant factors impacting the release of LDH in this experiment. Moreover, all secondary interactions between these factors are significant. This means when two factors are changed there is a significant impact on the release of LDH in this experiment. This test showed that the results observed in Tables 10 and 11 are significant.

TABLE 12

ANOVA (DOE) on LDH Cytotoxicity results:

| Source | Sum of Squares | df | Mean Square | F Value | p-value Prob > F | Significance? |
|---|---|---|---|---|---|---|
| Model | 44.46 | 12 | 3.71 | 28.09 | <0.0001 | significant |
| A-Media | 2.95 | 3 | 0.98 | 7.45 | 0.0006 | significant |
| B-Temp | 5.41 | 1 | 5.41 | 41.03 | <0.0001 | significant |
| C-Time | 5.07 | 1 | 5.07 | 38.45 | <0.0001 | significant |
| AB | 24.73 | 3 | 8.24 | 62.49 | <0.0001 | significant |
| AC | 4.83 | 3 | 1.61 | 12.21 | <0.0001 | significant |
| BC | 1.46 | 1 | 1.46 | 11.09 | 0.0021 | significant |
| Residual | 4.62 | 35 | 0.13 | | | |
| Lack of Fit | 0.51 | 3 | 0.17 | 1.33 | 0.2818 | not significant |
| Pure Error | 4.11 | 32 | 0.13 | | | |
| Cor Total | 49.08 | 47 | | | | |

To determine whether encapsulated PEC aggregates stored under similar above described conditions would function in vivo after transplantation, PEC aggregates were loaded into an implantable semi-permeable cell encapsulation device were stored for 4 or 7 days at room temperature in DB media, or for 4, 7 or 14 days at 4° C. in SPS-1 ("SPS") media and then washed in 10 mL HBSS (Hanks Balanced Salt Solution)+0.2% HSA+pen/strep. One of skill in the art will recognize that any of the other preservation solutions described above could be used for short term storage at room temperature or 4° C. including HEPES (4-(2-hydroxyethyl)-1-piperazineethanesulfonic acid) (Life Technologies).

Figure 14:
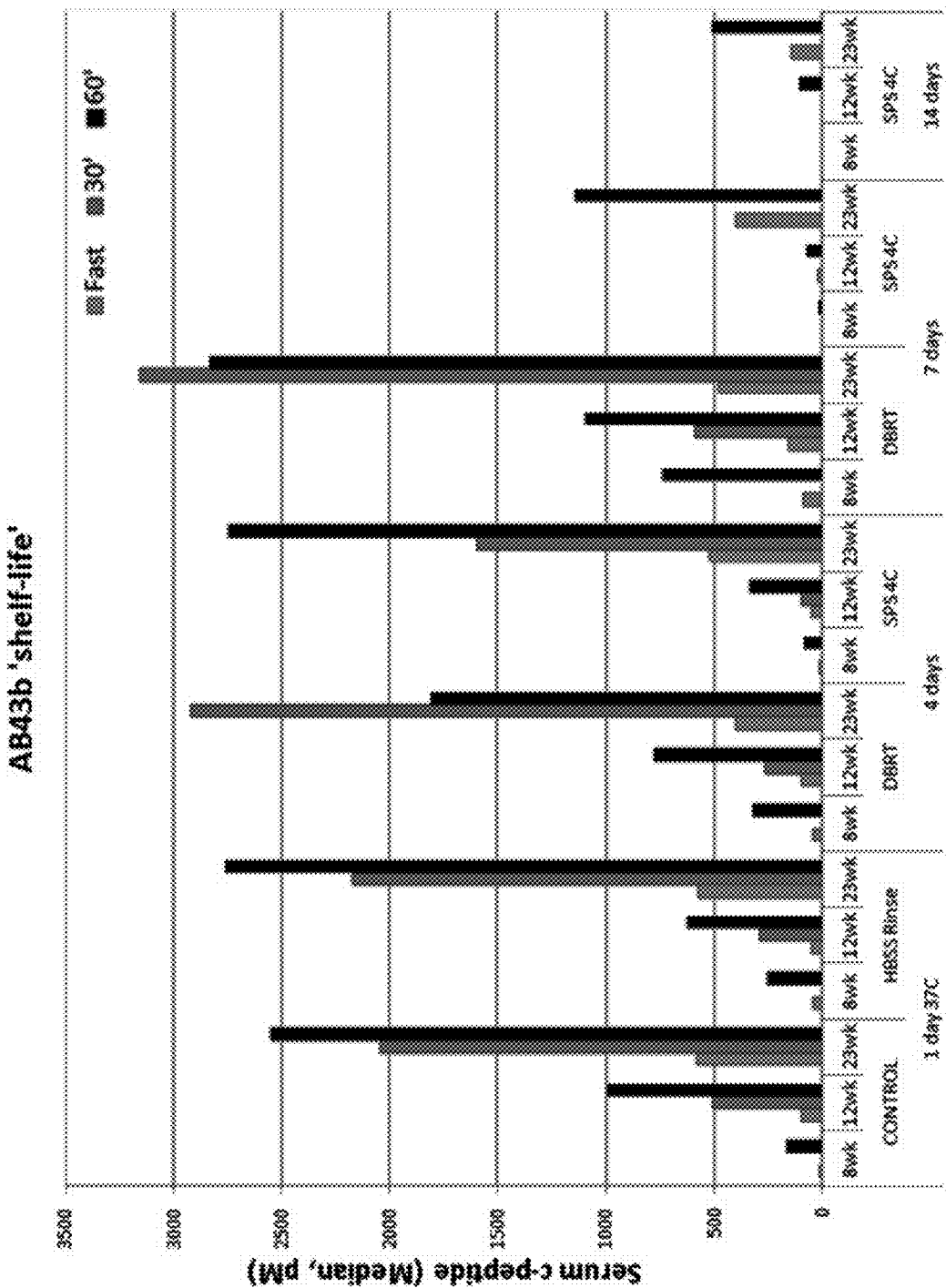
FIG. 14 is a graph showing concentration of human c-peptide in sera of mice implanted with a cell-device combination product. Expression levels were analyzed at 8, 12 and 23 weeks post-engraftment at fasting, 30 min and 60 min after 3 g/kg intraperitoneal glucose administration. N identifies the total numbers of GSIS (glucose stimulated insulin secretion) tests performed on mice within the indicated post-implant intervals. The box identifies the middle 50% of the values, the median is represented by the horizontal line within the box and the standard deviations are represented by the vertical lines extending from the box.

Mice were implanted with a cell-device combination product, whereby the device was loaded with fresh (not stored) or PEC aggregates stored for 4 or 7 days at room temperature in either DB media ("DBRT"), or stored for 4, 7 or 14 days at 4° C. in SPS-1 media ("SPS4C"). See FIG. 14. Serum C-peptide levels were analyzed at 8, 12 and 23 weeks post-engraftment at fasting, 30 minutes and 60 min after intraperitoneal glucose administration. FIG. 14 shows that storage of PEC cell aggregates for 4 or 7 days at room temperature in DB media (DBRT) had largely overlapping levels of C-peptide at 30 and 60 minutes following glucose administration as compared to fresh PEC samples ("Control") 8, 12 and 23 weeks after transplantation. Similarly, PEC cell aggregates stored for 4 days at 4° C. in SPS-1 media (SPS4C) had largely overlapping levels of C-peptide at 30 and 60 minutes following glucose administration as compared to fresh PEC samples (Control) 8, 12 and 23 weeks after transplantation. Interestingly, PEC cell aggregates stored for longer than 4 days (or 7 or 14 days) at 4° C. in SPS-1 media (SPS4C) did not have robust levels of C-peptide at 30 and 60 minutes following glucose administration as compared to the Control 8 over the same period. So, although there was increased cell death observed when PEC aggregates were stored at room temperature as compared to 4° C. (FIGS. 12A-12B and 13A-13B), storage at room temperature in DB media (DBRT) for up to 7 days did not affect in vivo function as shown in FIG. 14. In contrast, in vivo function of cell aggregates stored in SPS-1 media in 4° C. (SPS4C) was not affected up to 4 days, however, over 7 days cell aggregates incubated under the same conditions does appear to affect in vivo function Thus, storage of encapsulated PEC aggregates which were held in tissue preservation solution in at either room temperature or 4° C. prior to implantation is best when incubated in the preservation solution for less than 7 days (but possibly more than 4 days) in SPS media at 4° C., and at least up to 7 days in DB media at room temperature.

The above results are surprising because although there was increased cell death observed when PEC aggregates were stored at room temperature as compared to 4° C. (FIGS. 12A-12B and 13A-13B), the viable cells were still able to mature in vivo.

It is understood that cryopreservation of the PEC aggregates prior to treatment with the tissue preservation media is not a requirement and that cells treated with tissue preservation media without prior cryopreservation are expected to survive, mature and function as described above.

The compositions described above are suitable for use in therapy, including the treatment of insulin dependent diabetes. Cells preserved as described above do not need to be further processed to remove DMSO, DMEM or other toxic compounds from the storage or preparation medium, as the product is compatible with cell delivery devices and is not toxic by clinical administration.

Example 7

Cryopreserving the Cell-Device Combination Product

To date, reasonably robust methods for cryopreservation of encapsulated insulin producing cells has been limited to microencapsulation devices. While Itkin-Ansari describes cryopreservation of human insulin producing cells in a macro-encapsulation device, cell yield following cryopreservation is less than 10%. Itkin-Ansari et al., *Cryopreservation of human insulin expressing cells macro-encapsulated in a durable therapeutic immunoisolating device theracyte*, Cryo Letters. 2012 November-December; 33(6): 518-31. Therefore, it is desirable to cryopreserve the cell-device combination product described herein with greater than 10% cell yield post-thaw. Cryopreserving the cell-device combination product is advantageous because it allows for sterility testing to be performed before shipping the product to the clinical site, as well as improving storage and logistical flexibility.

PEC aggregates will be loaded into the implantable semipermeable device as described above and the port sealed without first being exposed to the cryopreservation solution. The combination product is placed inside a cryopreservation container. Although, cryopreservation of combination product can be performed in any type of container (e.g., vial, cryotube, bag, Daikyo Crystal Zenith® plastic vials (Aseptic Technologies.), made of cyclic olefin polymers,), cryopreserving the combination product in a collapsible cryopreservation bag considerably improves cell viability, and therefore in vivo maturation and function. This is because using a bag to hold the combination product reduces the total cryopreservation solution needed, and thickness of the packaged combination product which in turn makes it easier to control temperature changes.

In one embodiment the cryopreservation bag contains less that 100 mL, less than 50 mL, less than 25 mL, less than 10 mL, preferably less than 5 mL, preferably less than 3 mL cryopreservation solution. Before sealing the bag, air and excess cryopreservation solution is removed from the bag. Further a bag can be a closed system which reduces the risk of loss of sterility. In one embodiment the cryopreservation bag has 1 loading port, 2 loading ports, 3 loading ports, 4 loading ports or more. The loading ports are made with a material that can be cryopreserved without breaking or cracking. In one embodiment the cryopreservation solution is loaded into the cryopreservation bag through a loading port and is removed from the bag via a loading port. Multiple flushing cycles with cryopreservation medium may be performed to accelerate the diffusion of medium into the PEC cell aggregates, and thereby minimize the exposure to such solution prior to initiation of freezing. See FIG. 6.

In one preferred embodiment, the cryopreservation solution contains DMEM with about 30%-60% Xeno-free KO-SR, 25 mM HEPES and 10% DMSO solution. It is understood that if the DMSO concentration outside the device is higher, then the active time to equilibrate the cryopreservation solution to 10% DMSO inside the device is reduced. It is also understood that the equilibration time is reduced if the cryopreservation solution is flowed across the device. The combination product is equilibrated in cryopreservation solution at ambient temperature, and then equilibrated in cryopreservation solution at 4° C., and then the cryopreservation system (combination product and bag) is placed on ice and put in a programmed freezer which was equilibrated to 0° C. The packaged combination product is brought to −9° C. at a controlled rate. The packaged cell-device combination product is held at this temperature for about 10 minutes, or until the internal temperature of the device reaches −9° C. and the cells packages are seeded to initiate ice crystal formation. The packaged product is then slowly cooled at a controlled rate until the product reaches −40° C. The packaged combination product is subsequently cooled at a controlled rate until the sample reaches about −150° C. The packaged combination product is then moved to the vapor phase of a liquid nitrogen storage freezer.

Once the packaged combination product has reached its target cryopreservation temperature, it may be stored frozen for extended periods of time and distributed to clinical centers. At desired times the cryopreserved packaged combination product is thawed. Rapid thawing is achieved by placing the product in a bath of warm water, at a temperature of maximum 40° C., preferably between 10° C. and 40° C. and for instance about 37° C. Once thawed, the cryopreservative is removed from the cryopreservation system by flushing the system using the cryopreservation bag port with dilution medium. For example, one port is used to fill up the cryopreservation bag and another port is used to draw out the dilution medium. This can be performed simultaneously and continuously by utilizing an intravenous bag containing dilution medium connected to the inflow port. Such a system allows for a large dilution volume and diffusion gradient. If flushed via discrete boluses, the packaged combination product may be flushed more than once, optimally twice or three times or four. The dilution medium may be any dilution medium known in the art, for example, any of the media listed above for use in hibernating cells such as tissue/organ preservation solutions, or for growth and differentiation of cells. Once flushed, the combination product is ready for implantation into a mammalian host. Or, alternatively may be incubated in incubation medium (described above) for up to 1 hour, 2 hours, 3 hours, 4 hours, 5 hours, 10 hours, 24 hours, 48 hours, 72 hours, 4 days, 5 days, 6 days, 7 days, 8 days, 9 days, 10 days or longer.

One drawback to the above described approach is that the cryopreservation solution is slightly viscous and it may take some time to equilibrate across the device membrane. Therefore, in another embodiment, the PEC aggregates are placed in cryopreservation solution prior to loading into the implantable, semipermeable device. In another embodiment, the PEC aggregates are loaded into the implantable, semipermeable device and the cryopreservation solution is loaded into the device via the port.

It is understood that any cryopreservative known in the art can be used in a cryopreservative solution. Further, it is understood that DMSO can be used at a wide range of concentrations, e.g., about 1%, about 2%, about 3%, about 4%, about 5%, about 6%, about 7%, about 8%, about 9%, about 10%, about 11%, about 12%, about 13%, about 14%, about 15% or more.

In one embodiment the combination product can be cryopreserved using a vitrification procedure. After the combination product is equilibrated with cryopreservation solution in either a cryotube or bag, it is immediately transferred into the liquid phase of liquid nitrogen at −196° C. to induce rapid freezing. The product can be left in the liquid phase or moved to the vapor phase for long term storage. The cryopreservation solution for vitrification can include any cryopreservation solution known in the art and may include vitrification solution comprising a mixture of 0.5M DMSO, 0.5M propylene glycol, 0.25M 2,3-butanediol, 1.0M proline, 2.5% raffinose, 15% PVP (Ave. M.W.≈40,000), and 15% dextran (Ave. M.W.≈40,000-70,000); or a mixture of 0.5M DMSO, 0.5M propylene glycol, 0.25M 2,3-butanediol, 10% raffinose, 6% trehalose, 6% sucrose, 12% PVP (Ave. M.W.≈40,000), and 12% dextran (Ave. M.W.≈40,000-70,000); or a mixture of 0.5M DMSO, 0.5M propylene glycol, 0.25M 2,3-butanediol, 2.5% raffinose, 12% sucrose, 15% PVP (Ave. M.W.≈40,000), and 15% dextran (Ave. M.W.≈40,000-70,000).

In one embodiment the combination product can be cryopreserved using a Cells Alive System (ABI Corporation) which uses electromagnetic fields and mechanical vibrations to prevent ice crystal formation.

In one embodiment the combination product is pretreated prior to cryopreservation. Prior to addition of the cryopreservation solution the combination product is incubated in a nutrient medium at a temperature of from 27° C. to 42° C. and for a period of time from five minutes to twenty four hours. In some cases the nutrient medium contains an antibiotic. PEC aggregates can also be pretreated by heat shock before loading into the device as disclosed in EP0830059 incorporated by reference in its entirety. Heat shock induces tolerance to the abruptly increasing concentration of osmotics in cells that result from freezing by the formation of heat-shock proteins that stabilize proteins and membranes. Heat shock is performed by culturing the cells in a water bath at between about 31° C. to about 45° C., preferably between about 33° C. to about 42° C. and more preferably above about 37° C. Culturing is performed from a few minutes to a few hours, preferably from about one hour to about six hours, and more preferably from about two hours to about four hours. After this treatment, cells are transferred to room temperature (23° C. to 25° C.) for up to four hours before cryopreservation.

In one embodiment the cells are mixed with compounds prior to freezing, during freezing (cryopreservation solution) or during thawing or during flushing (dilution media), or during a post thaw incubation period (incubation media), at sufficient concentrations to stabilize and protect cell membranes from damage post-thaw. For example, Hank's balanced salt solution (preferably without $Ca^{++}$), DMEM containing media with no glucose or minimal to low amounts of glucose, buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2-3 mM), sorbitol (e.g., to an osmolarity of about 300 mM) or others additives as are well known in the art. Another suitable additive includes DNase (e.g., commercially available from Genentech, Incorporated as PULMOZYME®). Added proteins such as mammalian serum (preferably heat inactivated) or a serum protein such as albumin. Antifreeze proteins such as glycoproteins can be added to the cells. In one embodiment, a Rho-kinase inhibitor such as Y27632 can be added to the cells. Additionally, large stable molecules such as Dextran and/or D-glucose, PBS, L-glutamine, an antibiotic, at least one mitotic inhibitor such as fluorodeoxyuridine, cytosine arabinoside, uridine triphosphate or a combination thereof can be added to the cells. Additionally, anti-apoptotic agents, a composition that inhibits apoptosis and/or necrosis triggered by cryopreservation can be added to the cells. Cellular targets involved in the promotion of apoptosis which can be inhibited to improve cryopreservation include but are not limited to, Caspases (Cystine Proteases), ROCK, CAD (Caspase Activated DNAse) ASK1, Fas, JNK (Jun Kinase Family), FADD (Fas Activated Death Domain), TNF (Tumor Necrosis Factor), TRADD (TNF Receptor Activated Death Domain), RIP (receptor Interacting Protein), DAXX, Granzyme B, Bad (Mitochondrial Pro-apoptotic protein), Bax, Bid, Cytochrome C (Mitochondrial Pro-apoptotic protein), AIF (Apoptosis Initiation, Factor), MAPK (Mitogen Activated Protein Kinase Family) Calpain (Serine Proteases) Caspathin, Nitric Oxide, PARP (Poly-ADP Robose Polymerase) DFF (DNA Fragmentation Factor). Cellular targets involved in the prevention of apoptosis which can be activated to improve preservation efficacy include but are not limited to Bcl-2 (Mitochondrial Anti-apoptotic protein), Bcl-x (Mitochondrial Anti-apoptotic protein), IAP (Inhibitor of Apoptosis Protein), RAS (Receptor mediated pro-survival signal), AKT (Anti-apoptosis signal Initiation), TRAF2 (TNF Receptor Associated Factor 2) or a combination thereof can be added to the cells. Free radical scavengers and other anti-apoptotic agents include but are not limited to flavonoids vitamin e vitamin c vitamin d beta carotene (vitamin a) pycnogenol super oxidedismutase n-acetyl cysteine selenium catechins alpha lipoic acid melatonin glutathione zinc chelators calcium chelators 1-arginine or a combination thereof can be added to the cells. Additionally, anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS or a combination thereof can be added to the cells. It is understood that the addition of additional compounds does not cause spontaneous differentiation or affect the cell population percentages (endocrine, non-endocrine, residual) post thaw.

It is understood that the addition of any compound including the cryopreservation solution does not negatively affect aggregate distribution within the device.

In one embodiment, the combination product is not thawed in a single step. A two stage method of thawing cells from a cryopreserved state includes first warming the cells from a cryopreservation temperature to a transition temperature of at least −30° C. in a first, slow-warming stage by exposing the cells to a first environment having a temperature of less than −30° C., preferably −80° C. as described in EP 1274301 herein incorporated by reference. Once the cells have reached the transition temperature, they are subsequently further warmed the cells from the transition temperature by exposing the cells to a second environment having a temperature of at least 32° C. in a second, rapid-warming stage.

In one embodiment, the combination product is not flushed following thawing, i.e., DMSO is not removed prior to implantation.

It is understood that the combination product may be cryopreserved the same day or up to 1 day, 2 days, 3 days, 4 days, 5 days, 6 days, 7 days, 8 days, 9 days 10 days, 14 days, 3 weeks, 1 month, 2, months, 3, months, 4 months, 5 months, 6 months or more post encapsulation.

Figure 11:
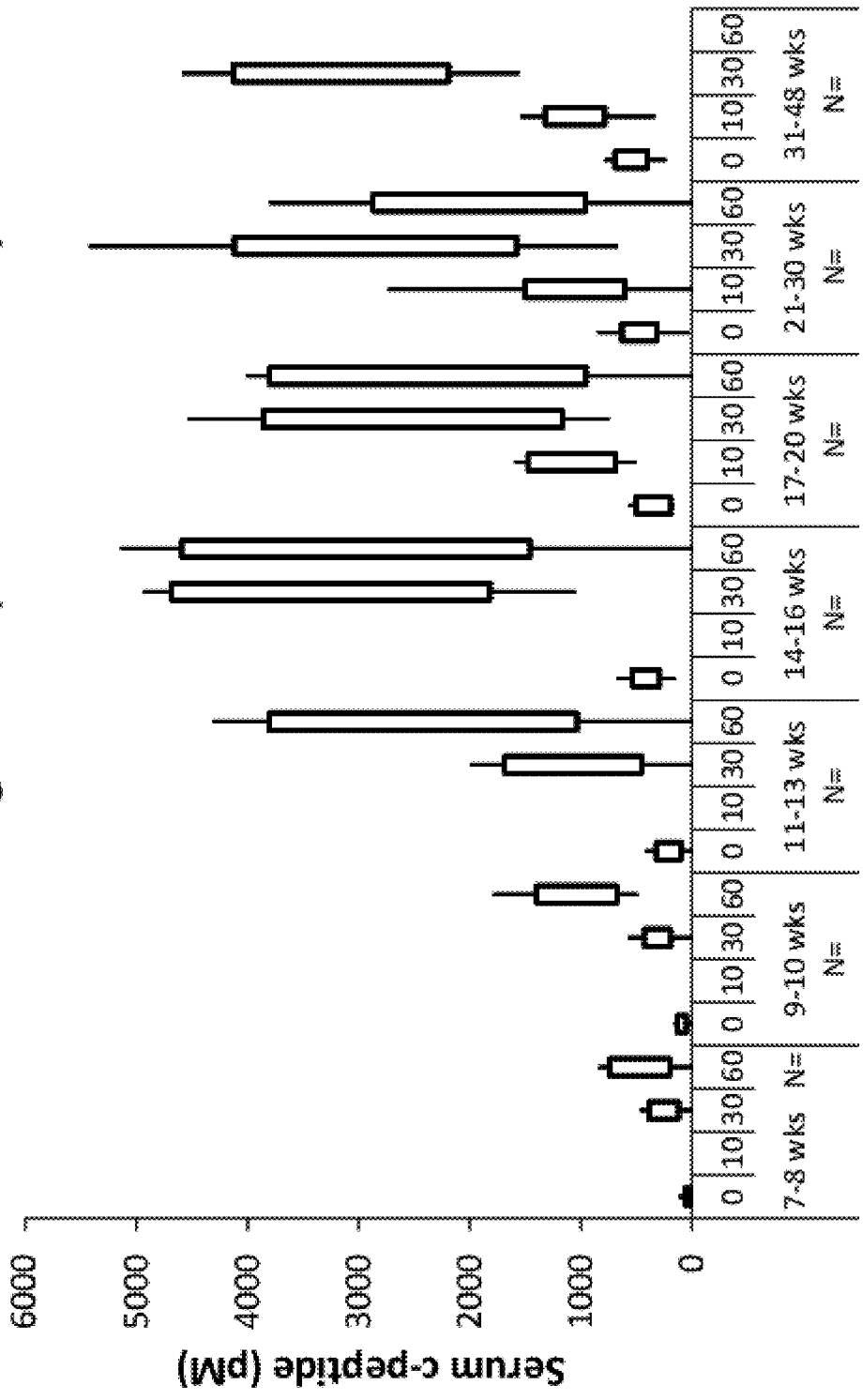
FIG. 11 is a graph showing concentration of human c-peptide in sera of implanted mice. Mice implanted with a cell-device combination product (PEC loaded in an implantable, semipermeable encapsulation device) were analyzed post-engraftment for serum levels of human C-peptide at fasting, 30 min, and 60 min after intraperitoneal glucose administration.

It is understood that the cells cryopreserved within the device mature and function in vivo to the same extent as cells which had not been cryopreserved. See. FIG. 11.

It is understood that cryopreserved combination product have comparable post-engraftment function in vivo, as defined by long-term glucose-responsive human c-peptide secretion or protection against STZ-induced hyperglycemia compared to combination products which are not cryopreserved.

It is understood that histological analysis shows cell content in both the cryopreserved and non-cryopreserved combination product to be not statistically different 12 weeks post engraftment.

It is understood that the methods disclosed herein for cryopreserving the combination product provides cell viability after thawing of preferably more than 10%, 20%, 30%, 40%, 50% preferably more than 70%, preferably more than 80%, and for instance 80%, 81%, 82%, 83%, 84%, 85%, 86%, 87%, 88%, 89%, 90%, 91%, 92%, 93%, 94%, 95%, 96%, 97%, 98%, 99% or 100%.

It will be apparent to one skilled in the art that varying substitutions, modifications or optimization, or combinations may be made to the embodiments disclosed herein without departing from the scope and spirit of the invention. The methods, compositions, and devices described herein are presently representative of preferred embodiments and are exemplary and are not intended as limitations on the scope of the patent. Changes, alternatives, modifications and variations therein and other uses will occur to those skilled in the art which are encompassed within the spirit of the invention and are defined by the scope of the disclosure.

All publications and patents mentioned in this specification are herein incorporated in their entireties by reference.

As used in the claims below and throughout this disclosure, by the phrase "consisting essentially of" is meant to include any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

EMBODIMENTS

Embodiment 1

A method for preserving encapsulated cell, said method comprising: a. obtaining cells to be cryopreserved; b. loading the cells into an implantable semi-permeable encapsulation device to create encapsulated cells to create a combination product; c. contacting the combination product with a cryopreservative; and d. cryopreserving the combination product.

Embodiment 2

A method for producing insulin in vivo in a mammal, said method comprising: a. obtaining an in vitro human PEC aggregate population; b. loading the PEC aggregate population into an implantable semi-permeable encapsulation device to create a combination product; c. contacting the combination product with a cryopreservative; d. cryopreserving the combination product; e. thawing the cryopreserved combination product; f. implanting the combination product into a mammalian host; and g. maturing the encapsulated PEC aggregates in said device in vivo such that the mature cell population comprises endocrine and acinar cells, wherein at least some of the endocrine cells are insulin secreting cells that produce insulin in response to glucose stimulation in vivo, thereby producing insulin in vivo to the mammal.

Embodiment 3

The method of embodiment 1, wherein the cells are pancreatic endoderm cell (PEC) aggregates.

Embodiment 4

The method of embodiment 1, wherein a cryopreservative is added to the cells to be cryopreserved prior to loading into the implantable semi-permeable device.

Embodiment 5

The method of embodiment 3, wherein a cryopreservative is added to the PEC aggregates prior to loading into the implantable semi-permeable device.

Embodiment 6

The method of embodiment 1, wherein the combination product is shipped to the implantation site in a cryopreserved state.

Embodiment 7

The method of embodiment 1, wherein the combination product is at a temperature range of negative 90 to negative 260 degrees Celsius.

Embodiment 8

The method of embodiment 1, wherein the combination product is at a temperature of negative 190 degrees Celsius.

Embodiment 9

The method of embodiment 1, wherein the cells to be cryopreserved when thawed do not leak from the implantable semi-impermeable device.

Embodiment 10

The method of embodiment 1, wherein the cell survival rate is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95%.

Embodiment 11

The method of embodiment 1, wherein the cell survival rate is greater than about 50%.

Embodiment 12

The method of embodiment 1, wherein the cell survival rate is greater than about 60%.

Embodiment 13

The method of embodiment 1, wherein the cell survival rate is greater than about 95%.

Embodiment 14

The method of embodiment 1, wherein the device comprises at least one loading port.

Embodiment 15

The method of embodiment 1, wherein the device comprises at least two loading ports.

Embodiment 16

A cryopreserved human PEC aggregate population, wherein the cell population is suitable for transplantation into a mammal.

Embodiment 17

The cell population of embodiment 16, wherein the PEC aggregate population is capable of maturing into islet or acinar cells in the mammal.

Embodiment 18

The cell population of embodiment 16, wherein the PEC aggregate population is capable of maturing into beta cells which are capable of secreting insulin in response to glucose stimulation.

Embodiment 19

The cell population of embodiment 16, wherein the PEC aggregate population comprises PDX1 positive PEC aggregates.

Embodiment 20

Cryopreserved PEC aggregates.

Embodiment 21

Cryopreserved PEC aggregates wherein greater than 50% of the cells survive thawing.

Embodiment 22

Cryopreserved VC combination product.

Embodiment 23

Cryopreserved VC combination product wherein greater than 50% of the cells survive thawing.

Embodiment 24

Cells stored at room temperature in media comprising DMEM Hi-Glucose.

Embodiment 25

Cells stored at 4° C. in a media comprising static preservation solution.

Embodiment 26

The media of embodiment 24 further comprising 1% B27 Supplement, 1% Penicillin/Streptomycin or 1% Glutamax.

Embodiment 27

The media of embodiment 24 or 25 wherein the cells are PEC.

Embodiment 28

A method for preserving encapsulated cell, said method comprising: a. obtaining cells to be preserved; b. loading the cells into an implantable semi-permeable encapsulation device to create encapsulated cells to create a combination product; c. contacting the combination product with a preservation solution; and d. storing the cells at room temperature.

Embodiment 29

A method for producing insulin in vivo in a mammal, said method comprising: a. obtaining an in vitro human PEC aggregate population; b. loading the PEC aggregate population into an implantable semi-permeable encapsulation device to create a combination product; c. contacting the combination product with a preservation solution; d. storing the combination product at room temperature; e. implanting the combination product into a mammalian host; and f. maturing the encapsulated PEC aggregates in said device in vivo such that the mature cell population comprises endocrine and acinar cells, wherein at least some of the endocrine cells are insulin secreting cells that produce insulin in response to glucose stimulation in vivo, thereby producing insulin in vivo to the mammal.

Embodiment 30

The method of embodiment 28 and 29 wherein the preservation solution comprises DMEM Hi-Glucose.

Embodiment 31

The method of embodiment 28 and 29 wherein the preservation solution is removed from the VC combination product prior to implantation.

Embodiment 32

The method of embodiment 28, wherein the cells are pancreatic endoderm cell (PEC) aggregates.

Embodiment 33

A method for preserving encapsulated cell, said method comprising: a. obtaining cells to be preserved; b. loading the cells into an implantable semi-permeable encapsulation device to create encapsulated cells to create a combination product; c. contacting the combination product with a preservation solution; and d. storing the cells at 4° C.

Embodiment 34

A method for producing insulin in vivo in a mammal, said method comprising: a. obtaining an in vitro human PEC aggregate population; b. loading the PEC aggregate population into an implantable semi-permeable encapsulation device to create a combination product; c. contacting the combination product with a preservation solution; d. storing the combination product at 4° C.; e. implanting the combination product into a mammalian host; and maturing the encapsulated PEC aggregates in said device in vivo such that the mature cell population comprises endocrine and acinar cells, wherein at least some of the endocrine cells are insulin secreting cells that produce insulin in response to glucose stimulation in vivo, thereby producing insulin in vivo to the mammal.

Embodiment 35

The method of embodiments 33 and 34 wherein the preservation solution is removed from the VC combination product prior to implantation.

Embodiment 36

The method of embodiment 33, wherein the cells are pancreatic endoderm cell (PEC) aggregates.

Embodiment 37

A method for cryopreserving an encapsulated cell population, said method comprising: obtaining a cell population to be cryopreserved; loading the cell population into an implantable semi-permeable encapsulation device thereby making an encapsulated cell population; contacting the encapsulated cell population with a cryopreservative for at least 20 minutes thereby cryopreserving the encapsulated cell population.

Embodiment 38

A method for producing insulin in vivo in a mammal, said method comprising: obtaining an in vitro human pancreatic cell aggregate population; loading the pancreatic cell aggregate population into an implantable semi-permeable encapsulation device thereby making an encapsulated pancreatic cell population; contacting the pancreatic cell population with a cryopreservative for at least 20 minutes thereby; cryopreserving the encapsulated pancreatic cell population; thawing the encapsulated pancreatic cell population; implanting the encapsulated pancreatic cell population into a mammalian host; and maturing the encapsulated pancreatic cell population in vivo to form a mature cell population comprising of endocrine and acinar cells, wherein at least some of the endocrine cells are insulin secreting cells that produce insulin in response to glucose stimulation in vivo, thereby producing insulin in vivo to the mammal.

Embodiment 39

The method of embodiment 37, wherein the cell population to be cryopreserved are PDX1 positive pancreatic endoderm cells.

Embodiment 40

The method of embodiment 39, wherein the PDX1 positive pancreatic endoderm cells are pancreatic endoderm cells.

Embodiment 41

The method of embodiment 37, wherein the cell population be cryopreserved are contacted with a cryopreservative prior to loading into the device.

Embodiment 42

The method of embodiment 37, wherein the encapsulated cell population is shipped to the implantation site in a cryopreserved state.

Embodiment 43

The method of embodiment 37, wherein the encapsulated cell population is at a temperature range of negative 90 to negative 260 degrees Celsius.

Embodiment 44

The method of embodiment 37, wherein the encapsulated cell population is at a temperature of negative 190 degrees Celsius.

Embodiment 45

The method of embodiment 37, wherein the encapsulated cell population does not leak from the device.

Embodiment 46

The method of embodiment 137, wherein the cell survival rate is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95%.

Embodiment 47

The method of embodiment 37, further comprising thawing the encapsulated cell population, wherein the survival rate for the thawed encapsulated cell population is greater than about 50%.

Embodiment 48

The method of embodiment 37, further comprising thawing the encapsulated cell population, wherein the survival rate for the thawed encapsulated cell population is greater than about 60%.

Embodiment 49

The method of embodiment 37, further comprising thawing the encapsulated cell population, wherein the survival rate for the thawed encapsulated cell population is greater than about 95%.

Embodiment 50

The method of embodiment 37, wherein the device comprises at least one loading port.

Embodiment 51

The method of embodiment 37, wherein the device comprises at least two loading ports.

Embodiment 52

A cryopreserved human PDX1 positive pancreatic endoderm population.

Embodiment 53

The cell population of embodiment 52, wherein the PDX1 positive pancreatic endoderm population is capable of maturing into endocrine and acinar cells in the mammalian host.

Embodiment 54

The cell population of embodiment 52, wherein the PDX1 positive pancreatic endoderm population is capable of maturing into beta cells which are capable of secreting insulin in response to glucose stimulation.

Embodiment 55

A cryopreserved PDX1 positive pancreatic endoderm population.

Embodiment 56

A cryopreserved PDX1 positive pancreatic endoderm population wherein greater than 50% of the cells survive thawing.

Embodiment 57

A method for cryopreserving an encapsulated cell population, said method comprising: obtaining cells to be cryopreserved; loading the cells into an implantable device thereby making encapsulated cell population; contacting the encapsulated cell population with a cryopreservation solution; and storing the encapsulated cell population at room temperature.

Embodiment 58

A method for producing insulin in vivo in a mammal, said method comprising: obtaining an in vitro human PDX1 positive pancreatic endoderm population; loading the PDX1 positive pancreatic endoderm population into an encapsulation device thereby making an encapsulated cell population; contacting the encapsulated cell population with a cryopreservation solution; storing the encapsulated cell population at room temperature; implanting the encapsulated cell population into a mammalian host; and maturing the encapsulated cell population in said device in vivo to become at least endocrine and acinar cells, wherein at least some of the endocrine cells are insulin secreting cells that produce insulin in response to glucose stimulation in vivo, thereby producing insulin in vivo to the mammal.

Embodiment 59

A method for cryopreserving encapsulated cell, said method comprising: obtaining cells to be cryopreserved; loading the cells into an encapsulation device thereby making encapsulated cells; contacting the encapsulated cells with a cryopreservation solution; and storing the encapsulated cells at 4° C.

Embodiment 60

A method for producing insulin in vivo in a mammal, said method comprising: obtaining an in vitro human PDX1 positive pancreatic endoderm population; loading the PDX1 positive pancreatic endoderm population into an encapsulation device to create an encapsulated cell population; contacting the encapsulated cell population with a cryopreservation solution; storing the encapsulated cell population at 4° C.; implanting the encapsulated cell population into a mammalian host; and maturing the encapsulated cell population in vivo such that the mature cell population comprises endocrine and acinar cells, wherein at least some of the endocrine cells are insulin secreting cells that produce insulin in response to glucose stimulation in vivo, thereby producing insulin in vivo to the mammal.

Embodiment 61

A method for producing insulin in vivo in a mammal, said method comprising: a. obtaining an in vitro human PDX1 positive pancreatic endoderm population; b. loading the PDX1 positive pancreatic endoderm population into an encapsulation device to create an encapsulated cell population; c. contacting the encapsulated cell population with a cryopreservation solution; d. storing the encapsulated cell population at 4° C.; e. implanting the encapsulated cell population into a mammalian host; and maturing the encapsulated cell population in vivo such that the mature cell population comprises endocrine and acinar cells, wherein at least some of the endocrine cells are insulin secreting cells that produce insulin in response to glucose stimulation in vivo, thereby producing insulin in vivo to the mammal.

Embodiment 62

The method of embodiments 60 and 61 wherein the cryopreservation solution is removed from the encapsulated cell population prior to implantation.

Embodiment 63

The method of embodiment 61, wherein the encapsulated cell population are pancreatic endoderm cell (PEC) aggregates.

We claim:

1. A cryopreservation container comprising: a cryopreserved combination product and a cryopreservation solution, wherein the cryopreserved-combination product comprises a human pancreatic and duodenal homeobox 1 (PDX1)-positive pancreatic endoderm cell population loaded into an implantable semi-permeable encapsulation device, wherein the human PDX1-positive pancreatic endoderm cell population comprises endocrine, non-endocrine, and residual cells, and the endocrine cells are chromogranin A (CHGA)+/homeobox protein Nkx-6.1 (NKX6.1)-/PDX1- and the non-endocrine cells are CHGA-/NKX6.1+/PDX1+, and wherein the cryopreservation container comprises at least one loading port for the cryopreservation solution, and wherein the cryopreservation solution comprises about 5% to about 15% dimethyl sulfoxide (DMSO), and wherein the human PDX1-positive pancreatic endoderm cell population upon thawing and transplantation into a mammal matures in vivo into an endocrine precursor population, and the expression of neurogenin-3 (NGN3) in the PDX1-positive pancreatic endoderm cell population is lower than the expression of NGN3 in the endocrine precursor population.

2. The cryopreservation container of claim 1, wherein the cryopreservation container is a vial, cryotube, or bag.

3. The cryopreservation container of claim 1, wherein the container comprises less than 100 mL, less than 50 mL, less than 25 mL, less than 10 mL, less than 5 mL, or less than 3 mL of the cryopreservation solution.

4. The cryopreservation container of claim 1, wherein the human PDX1-positive pancreatic endoderm cell population is contacted with cryopreservation solution prior to loading into the implantable semi-permeable encapsulation device.

5. The cryopreservation container of claim 1, wherein the cryopreservation solution is equilibrated inside the implantable semi-permeable encapsulation device to about 5% to about 15% DMSO.

6. The cryopreservation container of claim 1, wherein the combination product is pretreated prior to cryopreservation.

7. The cryopreservation container of claim 1, wherein the human PDX1-positive pancreatic endoderm cell population is mixed with a compound, a solution, or a protein prior to cryopreservation.

8. The cryopreservation container of claim 1, wherein the human PDX1-positive pancreatic endoderm cell population comprises human PDX1-positive pancreatic endoderm cell aggregates.

9. The cryopreservation container of claim 1, wherein greater than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% of the human PDX1-positive pancreatic endoderm cell population can survive thawing.

10. The cryopreservation container of claim 1, wherein the implantable semi-permeable encapsulation device comprises at least one loading port.

11. The cryopreservation container of claim 1, wherein the cryopreserved combination product is at a temperature of about negative 90 to about negative 260 degrees Celsius.

12. The cryopreservation container of claim 1, wherein the human PDX1-positive pancreatic endoderm cell population encapsulated in the device was contacted with a cryopreservative for at least 20 minutes prior to cryopreservation, or about 30 minutes prior to cryopreservation, or about 60 minutes prior to cryopreservation.

13. The cryopreservation container of claim 1, wherein there is a decrease in the residual cells following thawing of the human PDX1-positive pancreatic endoderm cell population.

14. The cryopreservation container of claim 1, wherein there is an increase in the non-endocrine cells as compared to endocrine cells following thawing of the human PDX1-positive pancreatic endoderm cell population.

15. The cryopreservation container of claim 1, wherein there is a decrease in the residual cells compared to the non-endocrine cells following thawing of the human PDX1-positive pancreatic endoderm cell population.

16. The cryopreservation container of claim 1, wherein there is an increase in the non-endocrine cells as compared to endocrine cells following thawing of the human PDX1-positive pancreatic endoderm cell population.

17. The cryopreservation container of claim 16, wherein greater than 40% of the human PDX1-positive pancreatic endoderm cell population that survive thawing are endocrine cells and greater than 50% of the human PDX1-positive pancreatic endoderm cell population that survive thawing are non-endocrine cells.

18. The cryopreservation container of claim 1, wherein the at least one loading port is sealed.

* * * * *